(12) United States Patent
Tsaklakidis et al.

(10) Patent No.: US 10,077,288 B2
(45) Date of Patent: Sep. 18, 2018

(54) HYDROXYSTATIN DERIVATIVES FOR THE TREATMENT OF ARTHROSIS

(71) Applicant: Merck Patent GmbH, Darmstadt (DE)

(72) Inventors: Christos Tsaklakidis, Weinheim (DE); Markus Klein, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/364,598

(22) Filed: Nov. 30, 2016

(65) Prior Publication Data
US 2017/0081361 A1    Mar. 23, 2017

Related U.S. Application Data

(62) Division of application No. 14/415,793, filed as application No. PCT/EP2013/001879 on Jun. 26, 2013, now Pat. No. 9,624,264.

(30) Foreign Application Priority Data

Jul. 24, 2012   (EP) ..................................... 12005379

(51) Int. Cl.
| | |
|---|---|
| *A61K 38/05* | (2006.01) |
| *C07K 5/08* | (2006.01) |
| *C07K 5/02* | (2006.01) |
| *A61K 38/06* | (2006.01) |
| *C07K 5/06* | (2006.01) |
| *A61K 38/00* | (2006.01) |

(52) U.S. Cl.
CPC ................ *C07K 5/08* (2013.01); *A61K 38/05* (2013.01); *A61K 38/06* (2013.01); *C07K 5/0205* (2013.01); *C07K 5/06* (2013.01); *A61K 38/00* (2013.01)

(58) Field of Classification Search
CPC ........ A61K 38/06; A61K 31/16; A61K 31/00; A61K 38/55
See application file for complete search history.

(56) References Cited

U.S. PATENT DOCUMENTS

| | | |
|---|---|---|
| 3,971,736 A | 7/1976 | Wagner et al. |
| 4,743,585 A | 5/1988 | Hudspeth et al. |
| 4,818,748 A | 4/1989 | Bender et al. |
| 5,849,691 A | 12/1998 | Majer et al. |
| 2006/0160747 A1 | 7/2006 | Peters et al. |

FOREIGN PATENT DOCUMENTS

| | | |
|---|---|---|
| DE | 3601248 A1 | 7/1987 |
| WO | 8604901 A1 | 8/1986 |
| WO | 97/30072 A1 | 8/1997 |
| WO | 2006050861 A2 | 5/2006 |

OTHER PUBLICATIONS

Lee et al., Pain Physician, 2011; 14:145-161.*
Merck manual, Overview of Pain: Pain: Merck Manual Professional, accessed on Jul. 9, 2012.*
The Philisophy of Combination Chemotherapy, Types of Chemotherapy Agents and Regimens, captured on May 26, 2011, available online at: https://web.archive.org/web/20110526005016/http://chemoth.com/combination.
J. G. Cannon, Chapter Nineteen in Burger's Medicinal Chemistry and Drug Discovery, Fifth Edition, vol. 1: Principles and Practice, Wiley-Interscience 1995, pp. 783-80.
Merriam-Webster dictionary, available on-line at http://www.merriam-webster.com/dictionary/kit, and http://www.merriam-webster.com/dictionary/set, respectively, accessed on Feb. 20, 2016.
International Search Report from PCT Application No. PCT/EP2013/001879 dated Sep. 26, 2013.
Lorena Taboada et al., "Solid-Phase Synthesis of Novel Trimers Containing a Phenylstatine Core and Analysis by High-Resolution Magic Angle Spinning", J. Comb. Chem., [2007], vol. 9, pp. 748-755.

* cited by examiner

*Primary Examiner* — Hasan Syed Ahmed
*Assistant Examiner* — Kaipeen E Yang
(74) *Attorney, Agent, or Firm* — Millen White Zelano and Branigan, PC; John Sopp

(57) ABSTRACT

The present invention relates to compounds of the formula (I) and in particular to medicaments comprising at least one compound of the formula (I) for use in the treatment and/or prophylaxis of physiological and/or pathophysiological conditions in the triggering of which cathepsin D is involved, in particular for use in the treatment and/or prophylaxis of arthrosis, traumatic cartilage injuries arthritis, pain, allodynia or hyperalgesia.

9 Claims, No Drawings

HYDROXYSTATIN DERIVATIVES FOR THE TREATMENT OF ARTHROSIS

The present invention relates to compounds of the formula I and in particular medicaments comprising at least one compound of the formula I for use in the treatment and/or prophylaxis of physiological and/or pathophysiological states in the triggering of which cathepsin D is involved, in particular for use in the treatment and/or prophylaxis of arthrosis, traumatic cartilage injuries, arthritis, pain, allodynia or hyperalgesia.

BACKGROUND OF THE INVENTION

Arthrosis is the most widespread joint disease worldwide, and radiological signs of arthrosis are found in the majority of over-65 year olds. In spite of this significant importance for the health system, the causes of arthrosis remain unclear to date, and effective preventative measures furthermore remain a distant aim. A reduction in the joint gap (caused by destruction of the joint cartilage), together with changes in the subchondral bone and osteophyte formation, are the radiological characteristics of the disease. For the patient, however, pain (load-dependent and nocturnal rest pain) with subsequent function impairments are to the fore. It is also these which force the patient into social isolation with corresponding secondary diseases.

The term arthrosis according to an unofficial definition in Germany denotes "joint wear" which exceeds the usual extent for the age. The causes are regarded as being excessive load (for example increased body weight), connatal or traumatic causes, such as malpositioning of the joints or also bone deformations due to bone diseases, such as osteoporosis. Arthrosis can likewise arise as a consequence of another disease, for example joint inflammation (arthritis) (secondary arthrosis), or accompany overload-induced effusion (secondary inflammation reaction) (activated arthrosis). The Anglo-American specialist literature differentiates between osteoarthrosis (osteoarthritis [OA]), in which the destruction of the joint surfaces can probably be attributed principally to the effects of load, and arthritis (rheumatoid arthritis [RA]), in which joint degeneration due to an inflammatory component is to the fore.

In principle, arthrosis is also differentiated according to its cause. Arthrosis alcaptonurica is based on increased deposition of homogenitic acid in joints in the case of previously existing alcaptonuria. In the case of haemophilic arthrosis, regular intra-articular bleeding occurs in the case of haemophilia (haemophilic joint). Arthrosis urica is caused by the mechanical influence of urate crystals (uric acid) on the healthy cartilage (W. Pschyrembel et al.: Klinisches Wörterbuch mit klinischen Syndromen and einem Anhang Nomina Anatomica [Clinical Dictionary with Clinical Syndromes and a Nomina Anatomica Annex]. Verlag Walter de Gruyter & Co, 253rd Edition, 1977).

The classical cause of arthrosis is dysplasia of joints. Using the example of the hip, it becomes clear that the zone with the greatest mechanical stress in the case of a physiological hip position represents a significantly larger area than in the case of a dysplastic hip. However, the stresses caused by the forces acting on the joint are substantially independent of the joint shape. They are essentially distributed over the main stress zone(s). A greater pressure will thus arise in the case of a relatively small zone than in the case of a larger one. The biomechanical pressure on the joint cartilage is thus greater in the case of a dysplastic hip than in the case of a physiological hip position. This rule is generally regarded as the cause of the increased occurrence of arthrotic changes in supporting joints which differ from the ideal anatomical shape.

If the consequences of an injury are responsible for premature wear, the term post-traumatic arthrosis is used. Further causes of secondary arthrosis that are being discussed are mechanical, inflammatory, metabolic, chemical (quinolones), trophic, hormonal, neurological and genetic reasons. In most cases, however, the diagnosis given is idiopathic arthrosis, by which the doctor means an apparent absence of a causal disease (H. I. Roach and S. Tilley, Bone and Osteoarthritis F. Bronner and M. C. Farach-Carson (Editors), Verlag Springer, Volume 4, 2007).

Medicinal causes of arthrosis can be, for example, antibiotics of the gyrase inhibitor type (fluoroquinolones, such as ciprofloxacin, levofloxacin). These medicaments result in complexing of magnesium ions in poorly vascularised tissues (hyaline joint cartilage, tendon tissue), which has the consequence that irreversible damage occurs to connective tissue. This damage is generally more pronounced in the growth phase in children and juveniles. Tendinopathies and arthropathies are known side effects of this class of medicaments. In adults, these antibiotics result in accelerated physiological degradation of the hyaline joint cartilage according to information from independent pharmacologists and rheumatologists (M. Menschik et al., Antimicrob. Agents Chemother. 41, 1997, pp. 2562-2565; M. Egerbacher et al., Arch. Toxicol. 73, 2000, pp. 557-563; H. Chang et al., Scand. J. Infect. Dis. 28, 1996, pp. 641-643; A. Chaslerie et al., Therapie 47, 1992, p. 80). Extended treatment with phenprocoumone can also favour arthrosis by decreasing bone density in the case of stresses of the joint internal structure.

Besides age, known risk factors for osteoarthrosis are mechanical overload, (micro)traumas, joint destabilisation caused by loss of the securing mechanisms, and genetic factors. However, neither the occurrence nor possible interventions have been fully explained (H. I. Roach and S. Tilley, Bone and Osteoarthritis F. Bronner and M. C. Farach-Carson (Editors), Verlag Springer, Volume 4, 2007).

In a joint affected by arthrosis, the content of nitrogen monoxide is increased in some cases. A similar situation has been observed due to high mechanical irritation of cartilage tissue (P. Das et al., Journal of Orthopaedic Research 15, 1997, pp. 87-93. A. J. Farrell et al. Annals of the Rheumatic Diseases 51, 1992, pp. 1219-1222; B. Fermor et al., Journal of Orthopaedic Research 19, 2001, pp. 729-737), whereas moderate mechanical stimulation tends to have a positive effect. The action of mechanical forces is thus causally involved in the progress of osteoarthrosis (X. Liu et al., Biorheology 43, 2006, pp. 183-190).

In principle, arthrosis therapy follows two aims: firstly freedom from pain under normal load and secondly the prevention of mechanical restrictions or changes in a joint. These aims cannot be achieved in the long term by pain treatment as a purely symptomatic therapy approach, since this cannot halt the progress of the disease. If the latter is to be achieved, the cartilage destruction must be stopped. Since the joint cartilage in adult patients cannot regenerate, the elimination of pathogenetic factors, such as joint dysplasia or malpositions, which result in increased point pressure on the joint cartilage, is in addition enormously important.

Finally, it is attempted to prevent or stop the degeneration processes in the cartilage tissue with the aid of medicaments.

An essential factor for the functioning state of the joint cartilage and thus the resistance thereof to stress is the extracellular matrix, which primarily consists of collagens, proteoglycans and water. The enzymes involved in degradation of the extracellular matrix include, in particular, the metalloproteases, aggrecanases and cathepsin enzymes. However, further enzymes can in principle also degrade cartilage matrix, for example plasmin, kallikrein, neutrophilelastase, tryptase and chymase.

Cathepsins belong to the papain superfamily of lysosomal proteases. Cathepsins are involved in normal proteolysis and the conversion of target proteins and tissues and in the initiation of proteolytic cascades and proenzyme activations. In addition, they are involved in MHC class II expression (Baldwin (1993) Proc. Natl. Acad. Sci., 90: 6796-6800; Mixuochi (1994) Immunol. Lett., 43:189-193). However, abnormal cathepsin expression can result in severe diseases. Thus, increased cathepsin expression has been detected in cancer cells, for example in breast, lung, prostate, glioblastoma and head and neck cancer, and it has been shown that cathepsins are associated with inadequate therapy success in breast, lung, head and neck cancer, and in brain tumours (Kos et al. (1998) Oncol. Rep., 5:1349-1361; Yan et al. (1998) Biol. Chem., 379:113-123; Mort et al.; (1997) Int. J. Biochem. Cell Biol., 29: 715-720; Friedrick et al. (1999) Eur. J Cancer, 35:138-144). In addition, abnormal cathepsin expression is apparently involved in the development of inflammatory and non-inflammatory diseases, such as, for example, rheumatoid arthritis and osteoarthrosis (Keyszer (1995) Arthritis Rheum., 38:976-984).

The molecular mechanism of cathepsin activity has not been fully explained. On the one hand, it has been found that, for example, induced cathepsin expression protects B cells from which serum is taken against apoptosis, and that treatment of the cells with antisense oligonucleotides of cathepsin B induces apoptosis (Shibata et al. (1998) Biochem. Biophys. Res. Commun., 251: 199-20; Isahara et al. (1999) Neuroscience, 91:233-249). These reports suggest an anti-apoptotic role of cathepsins. However, they are in complete contrast to earlier reports, which describe cathepsins as apoptosis mediators (Roberts et al (1997) Gastroenterology, 113: 1714-1726; Jones et al. (1998) Am. J. Physiol., 275: G723-730).

Cathepsins are synthesised as inactive zymogens on ribosomes and transferred into the lysosomal system. After proteolytic cleaving-off of the N-terminal propeptide, the cathepsin concentration in the acidic environment of the lysosomes increases to 1 mM, and the cathepsins are released into the extracellular medium by the lysosomes.

In the case of cathepsins, a differentiation is made between the cysteine cathepsins B, C, H, F, K, L, O, S, V and W, the aspartyl cathepsins D and E, and the serine cathepsin G.

Examples of cathepsin inhibitors in clinical development are cathepsin K inhibitors for the treatment of arthrosis and cathepsin S inhibitors for the treatment of arthritis, neuropathic pain and psoriasis.

Besides cathepsin D, the aspartyl proteases also include the HIV aspartyl protease (HIV-1 protease), renin, pepsin A and C, BACE (Asp2, memapsin), plasmepsins and the aspartyl haemoglobinases (Takahashi, T. et al., Ed. Aspartic Proteinases Structure, Function, Biology and Biomedical Implications (Plenum Press, New York, 1995), Adams, J. et al., Ann. Rep. Med. Chem. 31, 279-288, 1996; Edmunds J. et al., Ann. Rep. Med. Chem. 31, 51-60, 1996; Miller, D. K. et al., Ann. Rep. Med. Chem 31, 249-268, 1996). Cathepsin D is normally involved in the degradation of intracellular or phagocytised proteins and thus plays an important role in protein metabolism (Helseth, et al., Proc. Natl. Acad. Sci. USA 81, 3302-3306, 1984), in protein catabolism (Kay, et al., Intracellular Protein Catabolism (eds. Katunuma, et al., 155-162, 1989) and in antigen processing (Guagliardi, et al., Nature, 343, 133-139, 1990; Van Noort, et al., J. Biol. Chem., 264, 14159-14164, 1989).

Increased cathepsin D levels are associated with a number of diseases. Thus, increased cathepsin D levels correlate with a poor prognosis in breast cancer and with increased cell invasion and an increased risk of metastases, and shorter relapse-free survival time after therapy and a lower survival rate overall (Westley B. R. et al., Eur. J. Cancer 32, 15-24, 1996; Rochefort, H., Semin. Cancer Biol. 1:153, 1990; Tandon, A. K. et al., N. Engl. J. Med. 322, 297, 1990). The cathepsin D secretion rate in breast cancer is promoted by overexpression of the gene and by modified processing of the protein. Increased levels of cathepsin D and other proteases, such as, for example, collagenase, produced in the immediate vicinity of a growing tumour, could degrade the extracellular matrix in the environment of the tumour and thus promote the detachment of tumour cells and invasion into new tissue via the lymph and circulation system (Liotta L. A., Scientific American February:54, 1992; Liotta L. A. and Stetler-Stevenson W. G., Cancer Biol. 1:99, 1990; Liaudet E., Cell Growth Differ. 6:1045-1052, 1995; Ross J. S., Am. J. Clin. Pathol. 104:36-41, 1995; Dickinson A. J., J. Urol. 154:237-241, 1995).

Cathepsin D is in addition associated with degenerative changes in the brain, such as, for example, Alzheimer's disease. Thus, catepsin D is associated with cleavage of the amyloid-β precursor protein or of a mutant precursor which increases the expression of the amyloid protein in transfected cells (Cataldo, A. M. et al., Proc. Natl. Acad. Sci. 87:3861, 1990; Ladror, U. S. et al., J. Biol. Chem. 269: 18422, 1994, Evin G., Biochemistry 34:14185-14192, 1995). The amyloid-β protein, which is formed by proteolysis of the amyloid-β precursor protein, results in the formation of plaques in the brain and appears to be responsible for the development of Alzheimer's disease. Increased cathepsin D levels have also been found in the cerebrospinal fluid of Alzheimer's patients, and a high proteolytic activity of cathepsin D compared with the mutant amyloid-β precursor protein has been found (Schwager, A. L., et al. J. Neurochem. 64:443, 1995). In addition, a significant increase in cathepsin D activity is measured in biopsies from Huntington's disease patients (Mantle D., J. Neurol. Sci. 131:65-70, 1995).

Cathepsin D is thought to play an essential role at various levels in the development of arthrosis. Thus, increased mRNA levels of cathepsin D are measured in the joint cartilage of the hip joint head in dogs with spontaneous arthrosis compared with healthy dogs (Clements D. N. et al., Arthritis Res. Ther. 2006; 8(6):R158; Ritchlin C. et al., Scand. J. Immunnol. 40:292-298, 1994). Devauchelle V. et al. (Genes Immun. 2004, 5(8):597-608) also show different expression rates of cathepsin D in human patients in the case of arthrosis compared with rheumatoid arthritis (see also Keyszer G. M., Arthritis Rheum. 38:976-984, 1995). Cathepsin D also appears to play a role in mucolipidosis (Kopitz J., Biochem. J. 295, 2:577-580, 1993).

The lysosomal endopeptidase cathepsin D is the most widespread pro-teinase in the chondrocytes (Ruiz-Romero C. et al., Proteomics. 2005, 5(12): 3048-59). In addition, the proteolytic activity of cathepsin D has been detected in the cultivated synovium from osteoarthrosis patients (Bo G. P. et al., Clin. Rheumatol. 2009, 28(2):191-9), and increased proteolytic activity is also found in synovectomy tissue of patients with rheumatoid arthritis (Taubert H. et al., Autoimmunity. 2002, 35(3):221-4). Lorenz et al. (Proteomics.

2003, 3(6):991-1002) thus also write that, although the lysosomal and secreted aspartyl protease cathepsin D has not yet been studied in detail with respect to arthritis and arthrosis, in contrast to cathepsins B and L, Lorenz et al. found, however, higher protein levels of cathepsin D in the synovial tissue of patients with arthrosis compared with patients with rheumatoid arthritis.

Gedikoglu et al. (Ann. Rheum. Dis. 1986, 45(4):289-92) have likewise detected an increased proteolytic activity of cathepsin D in synovial tissue and Byliss and Ali (Biochem. J. 1978, 171(1):149-54) in the cartilage of patients with arthrosis.

In the case of arthrosis, a reduction in the pH occurs in regions of the cartilage. This reduction in the pH is of crucial importance for the understanding of catabolic processes in the cartilage.

In the case of arthrosis, a direct correlation is thus also found between a low pH in the joint tissue and the severity and progress of the disease. At a pH of 5.5, autodigestion of the cartilage occurs. This can be inhibited virtually completely by pepstatin or ritonavir in explant cultures (for example from mouse, cow or human). This suggests an essential role, or even a key role, of cathepsin D in arthrosis, since pepstatin inhibits aspartyl proteases with one exception—BACE 1—and only these two aspartyl proteases have hitherto been identified in the cartilage tissue. Thus, Bo G. P. et al. (Clin. Rheumatol. 2009, 28(2):191-9) also describe the important role of cathepsin D in pathological changes in joints.

The best-known aspartyl protease inhibitor is pepstatin, a peptide which was originally isolated from a *Streptomyces* culture. Pepstatin is effective against pepsin, cathepsin and renin. Many aspartyl protease inhibitors have therefore been modelled on the example of the structure of pepstatin (U.S. Pat. No. 4,746,648; Umezawa, H, et al., J Antibiot (Tokyo) 23:259-62, 1970; Morishima, H., et al., J. Antibiot. (Tokyo) 23:263-5, 1970; Lin, Ty and Williams, H R., J. Biol. Chem. 254: 11875-83, 1979; Jupp, R A, et al., Biochem. J. 265: 871-8, 1990; Agarwal, N S and Rich, D H, J. Med. Chem. 29:2519-24, 1986; Baldwin, E T, et al., Proc. Natl. Acad. Sci., USA 90: 6796-800, 1993; Francis, S E et al., EMBO J 13: 306-17, 1994).

Aspartyl proteases and cathepsin D are frequently described as target proteins for active compounds for the treatment of neurodegenerative diseases, cognitive disorders, dementia, Alzheimer's, cancer, malaria, HIV infection and diseases of the cardiovascular system, and inhibitors of aspartyl proteases or cathepsin D are disclosed for the treatment of these diseases, such as, for example, in WO 2009013293, EP 1987834, EP 1872780, EP 1867329, EP 1745778, EP 1745777, EP 1745776, WO 1999002153, WO 1999055687, U.S. Pat. No. 6,150,416, WO 2003106405, WO 2005087751, WO 2005087215, WO 2005016876, US 2006281729, WO 2008119772, WO 2006074950, WO 2007077004, WO 2005049585, U.S. Pat. No. 6,251,928 and U.S. Pat. No. 6,150,416.

Peptidic aspartyl protease inhibitors, in particular renin inhibitors or modulators of the renin-angiotensin system, are known, for example, from EP 77028, EP 161588, EP 337334 and EP 198271.

Peptidic cathepsin D inhibitors for the treatment of inflammatory diseases, arthritis, in particular rheumatoid arthritis, are known from U.S. Pat. No. 3,971,736. Peptidic cathepsin D and plasmepsin inhibitors for the treatment of malaria and Alzheimer's and prevention of the invasion and metastasisation of cancer cells are known, for example, from U.S. Pat. No. 5,849,691.

Although the known cathepsin D inhibitors and the two model compounds pepstatin and ritonavir effectively inhibit cathepsin D activity, they have, however, quite low selectivity for other aspartyl proteases. The role of the renin-angiotensin system (RAS) in the regulation of blood pressure and the fluid and electrolyte balance (Oparil, S. et al., N. Engl. J. Med. 1974; 291:381-401/446-57) and the efficacy of renin and pepsin inhibitors in diseases of the cardiovascular system is adequately known, and thus numerous side effects can be expected, in particular on oral or systemic administration of these low-selectivity cathepsin D inhibitors, and systemic complications can also be expected on local application due to diffusion of the compounds. In addition, the peptidic compounds in particular have low stability and are therefore not suitable for oral or systemic administration.

The invention was based on the object of finding novel compounds having valuable properties, in particular those which can be used for the preparation of medicaments.

The object of the present invention was, in particular, to find novel active compounds and particularly preferably novel cathepsin D inhibitors which can be employed for the prevention and treatment of arthrosis and have, in particular, high selectivity for cathepsin D compared with renin and pepsin. In addition, the aim was to find novel cathepsin D inhibitors which are sufficiently stable, at least on local or intra-articular administration.

SUMMARY OF THE INVENTION

Surprisingly, it has been found that the hydroxystatin derivatives according to the invention inhibit cathepsin D highly effectively and at the same time have high selectivity for cathepsin D compared with renin and pepsin, and thus few side effects can be expected on use thereof for the treatment of arthrosis. In addition, the compounds according to the invention have adequately good stability in synovial fluid, meaning that they are suitable for intra-articular administration and thus for the treatment of arthrosis. It has likewise surprisingly been found that the hydroxystatin derivatives according to the invention are able to reduce inflammation-induced thermal hyperalgesia depending on the dose.

The invention relates to hydroxystatin derivatives of the general formula I,

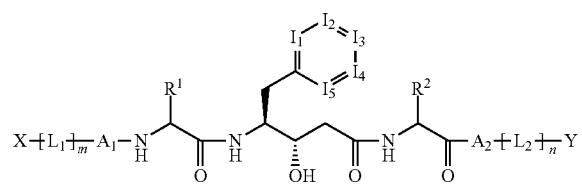

in which
$I_1$, $I_2$, $I_3$, $I_4$, $I_5$, independently of one another, are N or CR',
T is a phenyl, biphenyl or naphthyl which is unsubstituted or mono-, di- tri- or tetrasubstituted by R, or a mono- or bicyclic saturated, unsaturated or aromatic heterocycle having 1 to 4 N, O and/or S atoms, which may be mono-, di- or trisubstituted by R, $=S$, $=NR'$ and/or $=O$,
$R^1$ is ethyl, n-propyl, isopropyl, cyclopropyl, butyl, isobutyl, sec-butyl, cyclobutyl, tert-butyl, phenyl, benzyl, 2-oxetanyl, 3-oxetanyl, tetrahydrofuran-3-yl, tetrahydrofuran-2- yl, cyclopentyl, pentyl, methylsulfanylmethyl, ethylsulfanylmethyl, 2-methylsulfanylethyl, or 1-methylsulfanylethyl, $R^2$ is ethyl, n-propyl, isopropyl, cyclopropyl, butyl, isobutyl, sec-butyl, cyclobutyl, tert-butyl, phenyl, benzyl, 2-oxetanyl, 3-oxetanyl, tetrahydrofuran-3-yl, tetrahydrofuran-2-yl, cyclopentyl, pentyl, methylsulfanylmethyl, ethylsulfanylmethyl, 2-methylsulfanylethyl, or 1-methylsulfanylethyl, $A_1$ is a single bond or 1 to 3 amino acid radicals connected to one another in a peptide-like manner, or —CO—, —OCO—, —NRCO—, —SO$_2$— or —NRSO$_2$—, $A_2$ is a single bond or 1 to 3 amino acid radicals connected to one another in a peptide-like manner, $L_1$ is a single bond, a linear or branched alkyl linker having 1-10 C atoms, in which 1-5 CH$_2$ groups may be replaced, independently of one another, by O, S, SO, SO$_2$, NR, —(C═O)—, —CRR—, —OCO—, —NRCONR'—, —NRCO—, —NRSO$_2$R'—, —COO—, —CONR—, —C≡C— groups and/or by —CH═CH— groups and/or, in addition, 1-20 H atoms may be replaced by F and/or Cl, or —CRR'—, $L_2$ is a single bond, —CRR'—, —NR—, —NRCR'R— or —NRCRR'CRR', X, Y are H, T, linear or branched alkyl having 1-10 C atoms which is unsubstituted or mono-, di- or trisubstituted by ═S, ═NR, ═O, R, T, OR, NRR', SOR, SO$_2$R, SO$_2$NRR', CN, COOR, CONRR', NRCOR', NRCONR'R'', NRSO$_2$R' and/or NRCOR' and in which one, two or three CH$_2$ groups may be replaced, independently of one another, by O, S, SO, SO$_2$, NR, —OCO—, —NRCONR'—, —NRCO—, —NRSO$_2$R'—, —COO—, —CONR—, —C≡C— groups and/or by —CH═CH— groups and/or, in addition, 1-20 H atoms may be replaced by F and/or Cl, or cyclic alkyl having 3-7 C atoms which is unsubstituted or mono-, di- or tri- by ═S, ═NR, ═O, R, T, OR, NRR', SOR, SO$_2$R, SO$_2$NRR', CN, COOR, CONRR', NRCOR', NRCONR'R'', NRSO$_2$R' and/or NRCOR' and in which one, two or three CH$_2$ groups may be replaced, independently of one another, by O, S, SO, SO$_2$, NR, —OCO—, —NRCONR'—, —NRCO—, —NRSO$_2$R'—, —COO—, —CONR—, —C≡C— groups and/or by —CH═CH— groups and/or, in addition, 1-11 H atoms may be replaced by F and/or Cl, R,R', independently of one another, are H, linear or branched alkyl having 1-10 C atoms which is unsubstituted or mono-, di- or trisubstituted by ═S, ═NR, ═O, Hal, OH, NH$_2$, SO$_2$CH$_3$, SO$_2$NH$_2$, CN, CONH$_2$, NHCOCH$_3$, and/or NHCONH$_2$ and in which one, two or three CH$_2$ groups may be replaced, independently of one another, by O, S, SO, SO$_2$, NH, NCH$_3$, —OCO—, —NHCONH—, —NHCO—, —NRSO$_2$A-, —COO—, —CONH—, —NCH$_3$CO—, —CONCH$_3$—, —C≡C— groups and/or by —CH═CH— groups and/or, in addition, 1-20 H atoms may be replaced by F and/or Cl, or cyclic alkyl having 3-7 C atoms which is unsubstituted or mono-, di- or trisubstituted by ═S, ═NR, ═O, OH, NH$_2$, SO$_2$CH$_3$, SO$_2$NH$_2$, CN, CONH$_2$, NHCOCH$_3$, and/or NHCONH$_2$ and in which one, two or three CH$_2$ groups may be replaced, independently of one another, by O, S, SO, SO$_2$, NH, NCH$_3$, —OCO—, —NHCONH—, —NHCO—, —NRSO$_2$A-, —COO—, —CONH—, —NCH$_3$CO—, —CONCH$_3$— and/or by —CH═CH— groups and/or, in addition, 1-11 H atoms may be replaced by F and/or Cl, m is 0-4, n is 0-2, and Hal is F, Cl, Br or I, and physiologically acceptable salts, derivatives, solvates, prodrugs and stereoisomers thereof, including mixtures thereof in all ratios.

The invention preferably relates to all above-mentioned compounds of the formula I in which $R^1$ is isopropyl, 2-butyl or isobutyl, and physiologically acceptable salts, derivatives, solvates, prodrugs and stereoisomers thereof, including mixtures thereof in all ratios.

The invention furthermore preferably relates to all above-mentioned compounds of the formula I in which $R^2$ is n-propyl, isopropyl, 2-butyl or isobutyl, and physiologically acceptable salts, derivatives, solvates, prodrugs and stereoisomers thereof, including mixtures thereof in all ratios.

The invention particularly preferably relates to all above-mentioned compounds of the formula I in which $R^1$ is isopropyl, 2-butyl or isobutyl and $R^2$ is n-propyl, isopropyl, 2-butyl or isobutyl, and physiologically acceptable salts, derivatives, solvates, prodrugs and stereoisomers thereof, including mixtures thereof in all ratios.

The invention furthermore particularly preferably relates to all above-mentioned compounds of the formula I in which $R^1$ is isopropyl and $R^2$ is n-propyl, isopropyl or 2-butyl, and physiologically acceptable salts, derivatives, solvates, prodrugs and stereoisomers thereof, including mixtures thereof in all ratios.

The invention very particularly preferably relates to all above-mentioned compounds of the formula I in which $R^1$ is isopropyl having an S configuration of the chiral centre to which the isopropyl group is bonded, and $R^2$ is n-propyl, isopropyl or 2-butyl having an S configuration of the chiral centre to which the n-propyl, isopropyl or 2-butyl group is bonded, and physiologically acceptable salts, derivatives, solvates, prodrugs and stereoisomers thereof, including mixtures thereof in all ratios.

The invention preferably relates to all above-mentioned compounds of the formula I in which $A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine, O-ethylserine, —CO—, —OCO—, —NRCO—, —SO$_2$— and —NRSO$_2$—, and physiologically acceptable salts, derivatives, solvates, prodrugs and stereoisomers thereof, including mixtures thereof in all ratios.

The invention furthermore preferably relates to all above-mentioned compounds of the formula I in which $A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention particularly preferably relates to all above-mentioned compounds of the formula I in which $A_1$ is leucine or a single bond and $A_2$ is valine, and physiologically acceptable salts, derivatives, solvates, prodrugs and stereoisomers thereof, including mixtures thereof in all ratios.

The invention very particularly preferably relates to all above-mentioned compounds of the formula I in which $A_1$ is S-leucine or a single bond and $A_2$ is S-valine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl, 2-butyl or isobutyl, $A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine, O-ethylserine, —CO—, —OCO—, —NRCO—, —SO$_2$— and —NRSO$_2$—, and $A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl, $A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine, O-ethylserine, —CO—, —OCO—, —NRCO—, —SO$_2$— and —NRSO$_2$—, and $A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^2$ is n-propyl, isopropyl, 2-butyl or isobutyl, $A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tea-leucine, norleucine, methionine, phenylalanine, naphthylalanine, O-methylserine, O-ethylserine, —CO—, —OCO—, —NRCO—, —SO$_2$— and —NRSO$_2$—, and $A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^2$ is n-propyl, isopropyl or 2-butyl, $A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine, O-ethylserine, —CO—, —OCO—, —NRCO—, —SO$_2$— and —NRSO$_2$—, and $A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl,
$R^2$ is n-propyl, isopropyl or 2-butyl,
$A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine, O-ethylserine, —CO—, —OCO—, —NRCO—, —SO$_2$— and —NRSO$_2$—, and
$A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl having an S configuration of the chiral centre to which the isopropyl group is bonded,
$R^2$ is n-propyl, isopropyl or 2-butyl having an S configuration of the chiral centre to which the n-propyl, isopropyl or 2-butyl group is bonded,
$A_1$ is a single bond or an amino acid radical connected in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine, O-ethylserine, —CO—, —OCO—, —NRCO—, —SO$_2$— and —NRSO$_2$—, and
$A_2$ is a single bond or 1 to 2 amino acid radicals connected to one another in a peptide-like manner, selected from the group consisting of alanine, glycine, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, valine, norvaline, aminobutyric acid, leucine, isoleucine, proline, tert-leucine, norleucine, methionine, phenylalanine, naphthylalanine, O-methylserine and O-ethylserine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl, 2-butyl or isobutyl,
$A_1$ is leucine, in particular S-leucine or a single bond and
$A_2$ is valine, in particular S-valine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^2$ is n-propyl, isopropyl, 2-butyl or isobutyl,
$A_1$ is leucine, in particular S-leucine or a single bond and
$A_2$ is valine, in particular S-valine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl,
$R^2$ is n-propyl, isopropyl or 2-butyl,
$A_1$ is leucine, in particular S-leucine or a single bond and
$A_2$ is valine, in particular S-valine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl having an S configuration of the chiral centre to which the isopropyl group is bonded,
$R^2$ is n-propyl, isopropyl or 2-butyl having an S configuration of the chiral centre to which the n-propyl, isopropyl or 2-butyl group is bonded,
$A_1$ is leucine or a single bond and
$A_2$ is valine, and physiologically acceptable salts, derivatives, solvates, prodrugs and stereoisomers thereof, including mixtures thereof in all ratios.

The invention furthermore very particularly preferably relates to all above-mentioned compounds of the formula I in which $R^1$ is isopropyl having an S configuration of the chiral centre to which the isopropyl group is bonded,
$R^2$ is n-propyl, isopropyl or 2-butyl having an S configuration of the chiral centre to which the n-propyl, isopropyl or 2-butyl group is bonded,
$A_1$ is S-leucine or a single bond and
$A_2$ is S-valine, and physiologically acceptable salts, derivatives, solvates, prodrugs and stereoisomers thereof, including mixtures thereof in all ratios.

Very particular preference is also given to compounds of the formula I in which n is 0,
Y is OH, O-benzyl, a linear or branched alkyl having 1-10 C atoms or cyclic alkyl having 3-10 C atoms, in which one, two or three CH₂ groups may be replaced, independently of one another, by O, S, SO, SO₂, NR, —OCO—, —NRCONR'—, —NRCO—, —NRSO₂R'—, —COO—, —CONR—, —C≡C— groups and/or by —CH=CH— groups and/or, in addition, 1-20 H atoms may be replaced by F and/or Cl and which is unsubstituted or mono-, di- or trisubstituted by OR, NRR', SOR, SO₂R, SO₂NRR', CN, COOR, CONRR', NRCOR', NRCONR'R'', NRSO₂R' and/or NRCOR', m is 1, L₁ is —(C=O)—, X is a linear or branched alkyl having 1-10 C atoms or cyclic alkyl having 3-10 C atoms, in which one, two or three CH₂ groups may be replaced, independently of one another, by O, S, SO, SO₂, NR, —OCO—, —NRCONR'—, —NRCO—, —NRSO₂R'—, —COO—, —CONR—, —C≡C— groups and/or by —CH=CH— groups and/or, in addition, 1-20 H atoms may be replaced by F and/or Cl and which is unsubstituted or mono-, di- or trisubstituted by T, OR, NRR', SOR, SO₂R, SO₂NRR', CN, COOR, CONRR', NRCOR', NRCONR'R'', NRSO₂R' and/or, and physiologically acceptable salts, derivatives, solvates, prodrugs and stereoisomers thereof, including mixtures thereof in all ratios.

The invention furthermore very particularly preferably also relates to compounds of the formula I in which n is 0, Y is OH, O-benzyl, a linear or branched alkyl having 1-10 C atoms or cyclic alkyl having 3-10 C atoms which is unsubstituted or monosubstituted by COOH, COOR or OH, m is 1, L₁ is —(C=O)—, X is a linear or branched alkyl having 1-10 C atoms or cyclic alkyl having 3-10 C atoms, in which one, two or three CH₂ groups may be replaced, independently of one another, by 0 and which is unsubstituted or mono- or disubstituted by T, and physiologically acceptable salts, derivatives, solvates, prodrugs and stereoisomers thereof, including mixtures thereof in all ratios.

Very particular preference is also given to all above-mentioned compounds of the formula I in which L2 and Y together are 3-methylbutyric acid or benzyl 3-methylbutyrate.

All above-mentioned preferred, particularly preferred and very particularly preferred meanings of the above radicals of the compounds of the formula I should be understood in such a way that these preferred particularly preferred and very particularly preferred meanings or embodiments can be combined with one another in any possible combination to give compounds of the formula I and preferred compounds of the formula I of this type are likewise explicitly disclosed hereby.

Very particular preference is thus also given, for example, to compounds of the formula 1 in which R¹ is isopropyl having an S configuration of the chiral centre to which the isopropyl group is bonded, R² is n-propyl, isopropyl or 2-butyl having an S configuration of the chiral centre to which the n-propyl, isopropyl or 2-butyl group is bonded, A₁ is S-leucine or a single bond A₂ is S-valine, n is 0, Y is OH, O-benzyl, a linear or branched alkyl having 1-10 C atoms or cyclic alkyl having 3-10 C atoms which is unsubstituted or monosubstituted by COOH, COOR or OH, m is 1, L₁ is —(C=O)—, X is a linear or branched alkyl having 1-10 C atoms or cyclic alkyl having 3-10 C atoms, in which one, two or three CH₂ groups may be replaced, independently of one another, by 0 and which is unsubstituted or mono- or disubstituted by T, and physiologically acceptable salts, derivatives, solvates, prodrugs and stereoisomers thereof, including mixtures thereof in all ratios.

Very particular preference is given to the following compounds of the formula I:

a) benzly (S)-2-((2S,3S)-2-{(3S,4S)-3-hydroxy-4-[(S)-3-methyl-2-(3-phenylpropionylamino)butyrylamino]-5-phenylpentanoylamino}-3-methylpentanoylamino)-3-methylbutyrate b) benzly (S)-2-((2S,3S)-2-{(3S,4S)-3-hydroxy-4-[(S)-3-methyl-2-(4-phenylbutyrylamino)butyrylamino]-5-phenylpentanoylamino}-3-methylpentanoylamino)-3-methylbutyrate c) benzly (S)-2-[(2S,3S)-2-((3S,4S)-3-hydroxy-4-{(S)-3-methyl-2-[2-methyl-2-(naphthalen-2-yloxy)propionylamino]butyrylamino}-5-phenylpentanoylamino)-3-methylpentanoylamino]-3-methylbutyrate d) (S)-2-((2S,3S)-2-{(3S,4S)-3-hydroxy-4-[(S)-3-methyl-2-(3-phenyl-propionylamino)butyrylamino]-5-phenylpentanoylamino}-3-methylpentanoylamino)-3-methylbutyric acid e) (S)-2-((2S,3S)-2-{(3S,4S)-3-hydroxy-4-[(S)-3-methyl-2-(4-phenyl-butyrylamino)butyrylamino]-5-phenylpentanoylamino}-3-methylpentanoylamino)-3-methylbutyric acid f) (S)-2-[(2S,3S)-2-((3S,4S)-3-hydroxy-4-{(S)-3-methyl-2-[2-methyl-2-(naphthalen-2-yloxy)propionylamino]butyrylamino}-5-phenylpentanoylamino)-3-methylpentanoylamino]-3-methylbutyric acid g) (S)-2-[(2S,3S)-2-((3S,4S)-3-hydroxy-4-{(S)-3-methyl-2-[2-(naphthalen-2-yloxy)acetylamino]butyrylamino}-5-phenylpentanoylamino)-3-methylpentanoylamino]-3-methylbutyric acid h) (S)-2-[(2S,3S)-2-((3S,4S)-3-hydroxy-4-{(S)-3-methyl-2-[(S)-4-methyl-2-(3-methylbutyrylamino)pentanoylamino]butyrylamino}-5-phenylpentanoylamino)-3-methylpentanoylamino]-3-methylbutyric acid i) (S)-2-[(2S,3S)-2-((3S,4S)-3-hydroxy-4-{(R)-3-methyl-2-[(S)-4-methyl-2-(3-methylbutyrylamino)pentanoylamino]butyrylamino}-5-phenylpentanoylamino)-3-methylpentanoylamino]-3-methylbutyric acid j) benzly (S)-2-[(2S,3S)-2-((3S,4S)-4-{(S)-2-[2-(3,4-dimethoxyphenyl)-acetylamino]-3-methylbutyrylamino}-3-hydroxy-5-phenylpentanoylamino)-3-methylpentanoylamino]-3-methylbutyrate k) benzly (S)-2-[(2S,3S)-2-((3S,4S)-3-hydroxy-4-{(S)-2-[2-(4-methoxy-phenyl)acetylamino]-3-methylbutyrylamino}-5-phenylpentanoylamino)-3-methylpentanoylamino]-3-methylbutyrate l) benzly (S)-2-[(2S,3S)-2-((3S,4S)-4-{(S)-2-[2-(3-ethoxyphenyl)-acetylamino]-3-methylbutyrylamino}-3-hydroxy-5-phenylpentanoylamino)-3-methylpentanoylamino]-3-methylbutyrate m) benzly (S)-2-[(2S,3S)-2-((3S,4S)-3-hydroxy-4-{(S)-2-[2-(3-methoxy-phenyl)acetylamino]-3-methylbutyrylamino}-5-phenylpentanoylamino)-3-methylpentanoylamino]-3-methylbutyrate n) (S)-2-[(2S,3S)-2-((3S,4S)-4-{(S)-2-[2-(3,4-dimethoxyphenyl)acetylamino]-3-methylbutyrylamino}-3-hydroxy-5-phenylpentanoylamino)-3-methylpentanoylamino]-3-methylbutyric acid o) (S)-2-[(2S,3S)-2-((3S,4S)-3-hydroxy-4-{(S)-2-[2-(4-methoxyphenyl)-acetylamino]-3-methylbutyrylamino}-5-phenylpentanoylamino)-3-methylpentanoylamino]-3-methylbutyric acid p) benzly (S)-2-((2S,3S)-2-{(3S,4S)-3-hydroxy-4-[(S)-3-methyl-2-(2-naphthalen-2-ylacetylamino)butyrylamino]-5-phenylpentanoylamino}-3-methylpentanoylamino)-3-methylbutyrate q) (S)-2-[(2S,3S)-2-((3S,4S)-4-{(S)-2-[2-(3-ethoxyphenyl)acetylamino]-3-methylbutyrylamino}-3-hydroxy-5-phenylpentanoylamino)-3-methylpentanoylamino]-3-methylbutyric acid r) benzly (S)-2-[(2S,3S)-2-((3S,4S)-3-hydroxy-4-{(S)-2-[2-(2-methoxy-5-trifluoromethoxyphenyl)acetylamino]-3-methylbutyrylamino}-5-phenylpentanoylamino)-3-methylpentanoylamino]-3-methylbutyrate s) benzly (S)-2-[(2S,3S)-2-((3S,4S)-3-hydroxy-4-{(S)-3-methyl-2-[2-(3-phenoxyphenyl)acetylamino]butyrylamino}-5-phenylpentanoylamino)-3-methylpentanoylamino]-3-methylbutyrate t) (S)-2-[(2S,3S)-2-((3S,4S)-3-hydroxy-4-{(S)-2-[2-(3-methoxyphenyl)-acetylamino]-3-methylbutyrylamino}-5-phenylpentanoylamino)-3-methylpentanoylamino]-3-methylbutyric acid u) benzly (S)-2-((2S,3S)-2-{(3S,4S)-3-hydroxy-4-[(S)-3-methyl-2-(2-naphthalen-1-ylacetylamino)butyrylamino]-5-phenylpentanoylamino}-3-methylpentanoylamino)-3-methylbutyrate v) benzly (S)-2-[(2S,3S)-2-((3S,4S)-3-hydroxy-4-{(S)-2-[2-(2-methoxy-phenyl)acetylamino]-3-methylbutyrylamino}-5-phenylpentanoylamino)-3-methylpentanoylamino]-3-methylbutyrate w) benzly (S)-2-[(2S,3S)-2-((3S,4S)-4-{(S)-2-[(biphenyl-3-carbonyl)-amino]-3-methylbutyrylamino}-3-hydroxy-5-phenylpentanoylamino)-3-methylpentanoylamino]-3-methylbutyrate x) (S)-2-[(2S,3S)-2-((3S,4S)-3-hydroxy-4-{(S)-2-[2-(2-methoxy-5-trifluoromethoxyphenyl)acetylamino]-3-methylbutyrylamino}-5-phenylpentanoylamino)-3-methylpentanoylamino]-3-methylbutyric acid y) (S)-2-((2S,3S)-2-{(3S,4S)-3-hydroxy-4-[(S)-3-methyl-2-(2-naphthalen-2-ylacetylamino)butyrylamino]-5-phenylpentanoylamino}-3-methylpentanoylamino)-3-methylbutyric acid z) (S)-2-((2S,3S)-2-{(3S,4S)-4-[(S)-2-(3-tert-butoxybenzoylamino)-3-methylbutyrylamino]-3-hydroxy-5-phenylpentanoylamino}-3-methylpentanoylamino)-3-methylbutyric acid aa) (S)-2-[(2S,3S)-2-((3S,4S)-3-hydroxy-4-{(S)-3-methyl-2-[2-(3-phenoxyphenyl)acetylamino]butyrylamino}-5-phenylpentanoylamino)-3-methylpentanoylamino]-3-methylbutyric acid bb) (S)-2-[(2S,3S)-2-((3S,4S)-3-hydroxy-4-{(S)-2-[2-(2-methoxyphenyl)acetylamino]-3-methylbutyrylamino}-5-phenylpentanoylamino)-3-methylpentanoylamino]-3-methylbutyric acid cc) (S)-2-[(2S,3S)-2-((3S,4S)-4-{(S)-2-[2-(3,4-dimethylphenoxy)acetylamino]-3-methylbutyrylamino}-3-hydroxy-5-phenylpentanoylamino)-3-methylpentanoylamino]-3-methylbutyric acid dd) (S)-2-((2S,3S)-2-{(3S,4S)-3-hydroxy-4-[(S)-3-methyl-2-(2-naphthalen-1-ylacetylamino)butyrylamino]-5-phenylpentanoylamino}-3-methylpentanoylamino)-3-methylbutyric acid ee) (S)-2-[(2S,3S)-2-((3S,4S)-4-{(S)-2-[(biphenyl-3-carbonyl)amino]-3-methylbutyrylamino}-3-hydroxy-5-phenylpentanoylamino)-3-methylpentanoylamino]-3-methylbutyric acid ff) benzyl (S)-2-{(2S,3S)-2-[(3S,4S)-4-((S)-2-diphenylacetylamino-3-methylbutyrylamino)-3-hydroxy-5-phenylpentanoylamino]-3-methylpentanoylamino}-3-methylbutyrate gg) (S)-2-{(2S,3S)-2-[(3S,4S)-4-((S)-2-diphenylacetylamino-3-methyl-butyrylamino)-3-hydroxy-5-phenylpentanoylamino]-3-methylpentanoylamino}-3-methylbutyric acid hh) benzly (S)-2-[(2S,3S)-2-((3S,4S)-4-{(S)-2-[2-(3-ethoxyphenyl)-acetylamino]-3-methyl-1-(S)-oxopentylamino}-3-hydroxy-5-phenylpentanoylamino)-3-methylpentanoylamino]-3-methylbutyrate ii) benzly (S)-2-((2S,3S)-2-{(3S,4S)-3-hydroxy-4-[(S)-2-((S)-2-hydroxy-2-phenylacetylamino)-3-methylbutyrylamino]-5-phenylpentanoylamino}-3-methylpentanoylamino)-3-methylbutyrate jj) (S)-2-[(2S,3S)-2-((3S,4S)-3-hydroxy-4-{(S)-methyl-1-(S)-2-[2-(3-ethoxyphenyl)acetylamino]-3-oxopentylamino}-5-phenylpentanoylamino)-3-methylpentanoylamino]-3-methylbutyric acid kk) (S)-2-((2S,3S)-2-{(3S,4S)-3-hydroxy-4-[(S)-2-((S)-2-hydroxy-2-phenylacetylamino)-3-methylbutyrylamino]-5-phenylpentanoylamino}-3-methylpentanoylamino)-3-methylbutyric acid ll) (S)-2-((2S,3S)-2-{(3S,4S)-4-[(S)-2-(2,2-diethylbutyrylamino)-3-methylbutyrylamino]-3-hydroxy-5-phenylpentanoylamino}-3-methylpentanoylamino)-3-methylbutyric acid mm) (S)-2-{(2S,3S)-2-[(3S,4S)-4-((S)-2-{2-[3-(2-tert-butoxycarbonyl-aminoethoxy)phenyl]acetylamino}-3-methyl-1-(S)-oxopentylamino)-3-hydroxy-5-phenylpentanoylamino]-3-methylpentanoylamino}-3-methylbutyric acid nn) (S)-2-[(2S,3S)-2-((3S,4S)-3-hydroxy-4-{(2S,3S)-3-methyl-2-[2-(3-propoxyphenyl)acetylamino]pentanoylamino}-5-phenylpentanoylamino)-3-methylpentanoylamino]-3-methylbutyric acid oo) (S)-2-{(2S,3S)-2-[(3S,4S)-4-((S)-2-{2-[3-(2-aminoethoxy)phenyl]-acetylamino}-3-methyl-1-(S)-oxopentylamino)-3-hydroxy-5-phenylpentanoylamino]-3-methylpentanoylamino}-3-methylbutyric acid pp) N-[(1S,2S)-1-(1-ethylpropylcarbamoyl)-2-methylbutyl]-(2S,5S)-3-hydroxy-4-{(S)-3-methyl-2-[(S)-4-methyl-2-(3-methylbutyrylamino)-pentanoylamino]butyrylamino}-5-phenylpentanamide qq) N-[(1S,2S)-1-(1-ethylpropylcarbamoyl)-2-methylbutyl]-(2S,5S)-3-hydroxy-4-[(S)-3-methyl-2-((S)-4-methyl-2-phenylacetylaminopentanoylamino)-1-oxobutylamino]-5-phenylpentanamide rr) benzyl (S)-2-((2S,3S)-2-{(3S,4S)-3-hydroxy-4-[(S)-3-methyl-2-((S)-4-methyl-2-phenylacetylaminopentanoylamino)butyrylamino]-5-phenylpentanoylamino}-3-methylpentanoylamino)-3-methylbutyrate ss) (S)-2-((2S,3S)-2-{(3S,4S)-3-hydroxy-4-[(S)-3-methyl-2-((S)-4-methyl-2-phenylacetylaminopentanoylamino)butyrylamino]-5-phenylpentanoylamino}-3-methylpentanoylamino)-3-methylbutyric acid tt) N-((1S,2S)-1-cyclopentylcarbamoyl-2-methylbutyl)-(2S, 5S)-3-hydroxy-4-{(S)-3-methyl-2-[(S)-4-methyl-2-(3-methylbutyrylamino)-pentanoylamino]butyrylamino}-5-phenylpentanamide
uu) N—[(S)-1-(1-ethylpropylcarbamoyl)-2-methylpropyl]-(3S,4S)-3-hydroxy-4-{(S)-3-methyl-2-[(S)-4-methyl-2-(3-methylbutyrylamino)-pentanoylamino]butyrylamino}-5-phenylpentanamide
vv) N—[(S)-1-(1-ethylpropylcarbamoyl)butyl]-(3S,4S)-3-hydroxy-4-{(S)-3-methyl-2-[(S)-4-methyl-2-(3-methylbutyrylamino)pentanoylamino]-butyrylamino}-5-phenylpentanamide
ww) N-[(1S,2S)-1-(3-hydroxy-1,1-dimethylpropylcarbamoyl)-2-methylbutyl]-(3S,4S)-3-hydroxy-4-{(S)-3-methyl-2-[(S)-4-methyl-2-(3-methylbutyrylamino)pentanoylamino]butyrylamino}-5-phenylpentanamide and physiologically acceptable salts, derivatives, solvates, prodrugs and stereoisomers thereof, including mixtures thereof in all ratios.

The amino acid radicals mentioned above and below have the following common basic structure and differ merely in the radical R³.

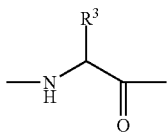

In the case of the amino acid radicals mentioned above and below, R³ stands for the radicals of the following amino acids:
Natural amino acids: alanine, arginine, asparagine, aspartic acid, cysteine, glutamine, glutamic acid, glycine, histidine, isoleucine, leucine, lysine, methionine, ornithine, phenylalanine, proline, serine, threonine, tryptophan, tyrosine and valine
Non-natural amino acids, such as, for example, cyclopropylglycine, cyclobutylglycine, cyclopentylglycine, cyclohexylglycine, 3-oxetanylglycine, 3-oxetanylglycine, tetrahydrofuran-3-ylglycine, tetrahydrofuran-2-ylglycine, ethylsulfanylmethylglycine, 2-methylsulfanylethylglycine, 1-methylsulfanylethylglycine, norvaline, aminobutyric acid, tert-leucine, norleucine, naphthylalanine, O-methylserine, O-ethylserine and the like.

If the above-mentioned amino acids can occur in a plurality of enantiomeric forms, all these forms and also mixtures thereof (for example DL forms) are included above and below.

Furthermore, the abbreviations have the following meanings:
Boc ter-butoxycarbonyl
CBZ benzyloxycarbonyl
DNP 2,4-dinitrophenyl
FMOC 9-fluorenylmethoxycarbonyl
imi-DNP 2,4-dinitrophenyl in the 1-position of the imidazole ring
OMe methyl ester
POA phenoxyacetyl
DCCl dicyclohexylcarbodiimide
HOBt 1-hydroxybenzotriazole
Hal denotes fluorine, chlorine, bromine or iodine, in particular fluorine or chlorine.

—(C=O)— denotes carbonyl oxygen or stands for

Alkyl or A is an unbranched (linear) or branched hydrocarbon chain and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl, further preferably, for example, trifluoro-methyl.

Cyclic alkyl or cycloalkyl is a cyclic hydrocarbon chain and has 3-10, preferably 3-7 C atoms and preferably denotes cyclopropyl, cyclobutyl, cyclopentyl, cyclohexyl or cycloheptyl.

A mono- or bicyclic saturated, unsaturated or aromatic heterocycle preferably denotes unsubstituted or mono-, di- or trisubstituted 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benz-oxadiazol-5-yl.

The heterocyclic radicals may also be partially or fully hydrogenated and also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Heterocycle furthermore denotes, for example, 2-oxopiperidin-1-yl, 2-oxo-pyrrolidin-1-yl, 2-oxo-1H-pyridin-1-yl, 3-oxomorpholin-4-yl, 4-oxo-1H-pyridin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl or 2-azabicyclo[2.2.2]octan-3-on-2-yl.

All physiologically acceptable salts, derivatives, solvates and stereoisomers of these compounds, including mixtures thereof in all ratios, are also in accordance with the invention.

The invention also relates to the optically active forms (stereoisomers), the enantiomers, the racemates, the diastereomers and hydrates and solvates of these compounds.

Compounds of the formula I according to the invention may be chiral owing to their molecular structure and may accordingly occur in various enantiomeric forms. They may therefore be in racemic or optically active form. Since the pharmaceutical efficacy of the racemates or stereoisomers of the compounds according to the invention may differ, it may be desirable to use the enantiomers. In these cases, the end product, but also even the intermediates, may be separated into enantiomeric compounds by chemical or physical measures known to the person skilled in the art or already employed as such in the synthesis.

Pharmaceutically or physiologically acceptable derivatives are taken to mean, for example, salts of the compounds according to the invention and also so-called prodrug compounds. Prodrug compounds are taken to mean compounds of the formula I which have been modified with, for example, alkyl or acyl groups (see also amino- and hydroxyl-protecting groups below), sugars or oligopeptides and which are rapidly cleaved or liberated in the organism to form the effective compounds according to the invention. These also include biodegradable polymer derivatives of the compounds according to the invention, as described, for example, in Int. J. Pharm. 115 (1995), 61-67.

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methyl-sulfonates or p-toluenesulfonates.

Solvates of the compounds of the formula I are taken to mean adductions of inert solvent molecules onto the compounds of the formula I which form owing to their mutual attractive force. Solvates are, for example, hydrates, such as monohydrates or dihydrates, or alcoholates, i.e. addition compounds with alcohols, such as, for example, with methanol or ethanol.

It is furthermore intended that a compound of the formula I includes iso-tope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^{3}H$ or $^{14}C$, has been incorporated is suitable for medicament and/or substrate tissue distribution assays. These radioisotopes, i.e. tritium ($^{3}H$) and carbon-14 ($^{14}C$), are particularly preferred owing to their simple preparation and excellent detectability. Incorporation of heavier isotopes, for example deuterium ($^{2}H$), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

In order to manipulate the oxidative metabolism of the compound by way of the primary kinetic isotope effect, deuterium ($^{2}H$) can also be incorporated into a compound of the formula I. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D=2$-$7$ are typical. If this rate difference is successfully applied to a compound of the formula I that is susceptible to oxidation, the profile of this compound in vivo can thereby be drastically modified and result in improved pharmacokinetic properties.

When discovering and developing therapeutic agents, the person skilled in the art attempts to optimise pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of the compounds of the formula I are thereby obtained and can be expressed quantitatively in terms of increases in the in-vivo half-life (T/2), concentration at maximum therapeutic effect ($C_{max}$), area under the dose response curve (AUC), and F; and in terms of reduced clearance, dose and costs of materials.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

The replacement of hydrogen by deuterium in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of two stereoisomeric compounds. However, preference is also given to mixtures of two or more compounds of the formula I.

The invention additionally relates to a process for the preparation of the compounds of the formula I, characterised in that a) a compound of the formula II, in which $I_1$, $I_2$, $I_3$, $I_4$ and $I_5$ have the meanings indicated above and Q denotes an amino-protecting group, is reacted with a compound of the formula III, in which Y, $L_2$, n, $A_2$ and $R^2$ have the meanings indicated above, with formation of a peptide bond between the carboxyl group of the compound of the formula II and the amino group of the compound of the formula III to give a compound of the formula IV, and, in a second step, the compound of the formula IV is converted into a compound of the formula V by removal of the protecting group Q,

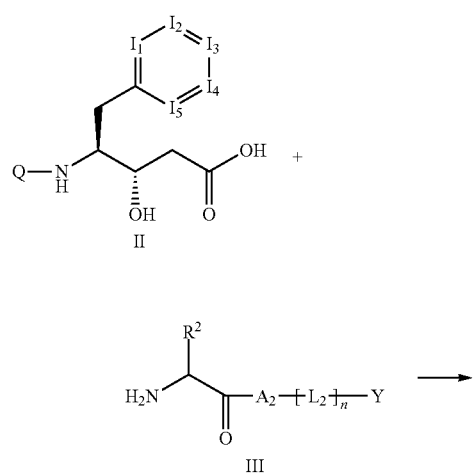

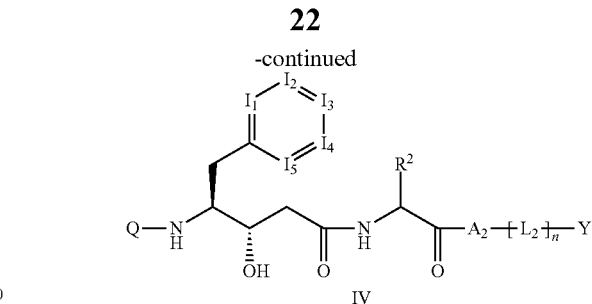

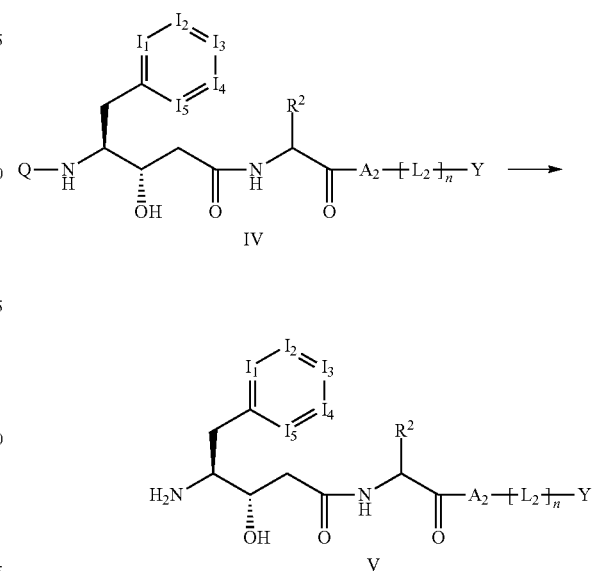

b) and a compound of the formula VI, in which X, $L_1$, m, $A_1$ and $R^1$ have the meanings indicated above and the radical X is optionally protected by a protecting group, is reacted with a compound of the formula V, in which the radical Y is optionally protected by a protecting group, with formation of a peptide bond between the carboxyl group of the compound of the formula VI and the amino group of the compound of the formula V and by removal of any protecting groups present on the radicals X and Y to give a compound of the formula I, in which $I_1$, $I_2$, $I_3$, $I_4$, $I_5$, X, Y, $L_1$, $L_2$, $R^1$, $R^2$, $A_1$, $A_2$, m and n have the meanings indicated in above, or

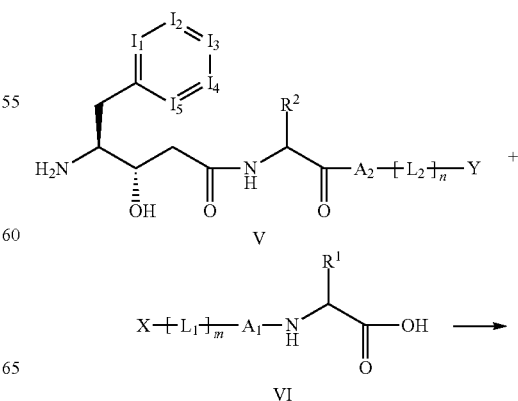

-continued

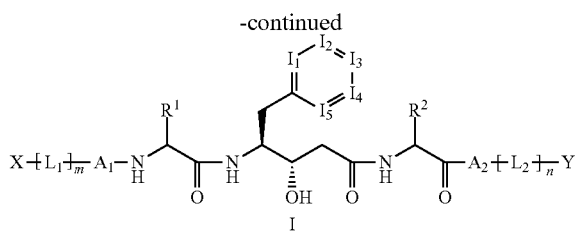

I c) the base of a compound of the formula I is converted into one of its salts by treatment with an acid, or
d) an acid of a compound of the formula I is converted into one of its salts by treatment with a base.

It is also possible to carry out the reactions stepwise in each case and to modify the sequence of the linking reactions of the building blocks with adaptation of the protecting-group concept.

The starting materials or starting compounds are generally known. If they are novel, they can be prepared by methods known per se.

If desired, the starting materials can also be formed in situ by not isolating them from the reaction mixture, but instead immediately converting them further into the compounds of the formula I.

The compounds of the formula I are preferably obtained by liberating them from their functional derivatives by solvolysis, in particular by hydrolysis, or by hydrogenolysis. Preferred starting materials for the solvolysis or hydrogenolysis are those which contain correspondingly protected amino, carboxyl and/or hydroxyl groups instead of one or more free amino, carboxyl and/or hydroxyl groups, preferably those which carry an amino-protecting group instead of an H atom which is connected to an N atom. Preference is furthermore given to starting materials which carry a hydroxyl-protecting group instead of the H atom of a hydroxyl group. Preference is also given to starting materials which carry a protected carboxyl group instead of a free carboxyl group. It is also possible for a plurality of identical or different protected amino, carboxyl and/or hydroxyl groups to be present in the molecule of the starting material. If the protecting groups present are different from one another, they can in many cases be cleaved off selectively.

The term "amino-protecting group" is generally known and relates to groups which are suitable for protecting (blocking) an amino group against chemical reactions, but which can easily be removed after the desired chemical reaction has been carried out elsewhere in the molecule. Typical of such groups are, in particular, unsubstituted or substituted acyl groups, furthermore unsubstituted or substituted aryl (for example 2,4-dinitrophenyl) or aralkyl groups (for example benzyl, 4-nitrobenzyl, triphenylmethyl). Since the amino-protecting groups are removed after the desired reaction or reaction sequence, their type and size is, in addition, not crucial, but preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of such acyl groups are alkanoyl, such as acetyl, propionyl, buturyl, aralkanoyl, such as phenylacetyl, aroyl, such as benzoyl or toluyl, aryoxyaklkanoyl, such as phenoxyacetyl, alkyoxycarbonyyl, such as methoxycarbonyl, ethoxycarbonyl, 2,2,2-trichloroethoxycarbonyl, BOC, 2-iodoethoxycaronyl, aralkoxycarbonyl. such as CBZ, 4-methoxybenzyloxycarbonyl or FMOC. Preferred acyl groups are CBZ, FMOC, benzyl and acetyl.

The term "acid-protecting group" or "carboxyl-protecting group" is likewise generally known and relates to groups which are suitable for protecting a —COOH group against chemical reactions, but which can easily be removed after the desired chemical reaction has been carried out elsewhere in the molecule. The use of esters instead of the free acids, for example of substituted and unsubstituted alkyl esters (such as methyl, ethyl, tert-butyl and substituted derivatives thereof), of substituted and unsubstituted benzyl esters or silyl esters, is typical. The type and size of the acid-protecting groups is not crucial, but preference is given to those having 1-20, in particular 1-10, C atoms.

The term "hydroxyl-protecting group" is likewise generally known and relates to groups which are suitable for protecting a hydroxyl group against chemical reactions, but which can easily be removed after the desired chemical reaction has been carried out elsewhere in the molecule. Typical of such groups are the above-mentioned unsubstituted or substituted aryl, aralkyl or acyl groups, furthermore also alkyl groups. The their type and size of the hydroxyl-protecting groups is not crucial, but preference is given to those having 1-20, in particular 1-10, C atoms. Examples of hydroxyl-protecting groups are, inter alia, benzyl, p-nitrobenzoyl, p-toluenesulfonyl and acetyl, where benzyl and acetyl are preferred.

Further typical examples of amino-, acid- and hydroxyl-protecting groups are found, for example, in "Greene's Protective Groups in Organic Synthesis", fourth edition, Wiley-Interscience, 2007

The functional derivatives of the compounds of the formula I to be used as starting materials can be prepared by known methods of amino-acid and peptide synthesis, as described, for example, in the said standard works and patent applications.

The compounds of the formula I are liberated from their functional derivatives, depending on the protecting group used, for example, with the aid of strong acids, advantageously using trifluoroacetic acid or perchloric acid, but also using other strong inorganic acids, such as hydrochloric acid or sulfuric acid, strong organic acids, such as trichloroacetic acid, or sulfonic acids, such as benzoyl- or p-toluenesulfonic acid. The presence of an additional inert solvent and/or a catalyst is possible, but is not always necessary.

Depending on the respective synthetic route, the starting materials can optionally be reacted in the presence of an inert solvent.

Suitable inert solvents are, for example, heptane, hexane, petroleum ether, DMSO, benzene, toluene, xylene, trichloroethylene-, 1,2-dichloroethanecarbon tetrachloride, chloroform or dichloromethane; alcohols, such as methanol, ethanol, isopropanol, n-propanol, n-butanol or tert-butanol; ethers, such as diethyl ether, diisopropyl ether (preferably for substitution on the indole nitrogen), tetrahydrofuran (THF) or dioxane; glycol ethers, such as ethylene glycol monomethyl or monoethyl ether, ethylene glycol dimethyl-I ether (diglyme); ketones, such as acetone or butanone; amides, such as acetamide, dimethylacetamide, N-methylpyrrolidone (NMP) or dimethylformamide (DMF); nitriles, such as acetonitrile; esters, such as ethyl acetate, carboxylic acids or acid anhydrides, such as, for example, such as acetic acid or acetic anhydride, nitro compounds, such as nitromethane or nitrobenzene, optionally also mixtures of the said solvents with one another or mixtures with water.

The amount of solvent is not crucial; 10 g to 500 g of solvent can preferably be added per g of the compound of the formula I to be reacted.

It may be advantageous to add an acid-binding agent, for example an alkali metal or alkaline-earth metal hydroxide, carbonate or bicarbonate or other alkali or alkaline-earth metal salts of weak acids, preferably a potassium, sodium or calcium salt, or to add an organic base, such as, for example, on triethylamine, dimethylamine, pyridine or quinoline, or an excess of the amine component.

The resultant compounds according to the invention can be separated from the corresponding solution in which they are prepared (for example by centrifugation and washing) and can be stored in another composition after separation, or they can remain directly in the preparation solution. The resultant compounds according to the invention can also be taken up in desired solvents for the particular use.

Suitable reaction temperatures are temperatures from 0 to 40° C., preferably 5 to 25° C.

The reaction duration depends on the reaction conditions selected. In general, the reaction duration is 0.5 hour to 10 days, preferably 1 to 24 hours. On use of a microwave, the reaction time can be reduced to values of 1 to 60 minutes.

The compounds of the formula I and also the starting materials for their preparation are, in addition, prepared by known methods, as described in the literature (for example in standard works, such as Houben-Weyl, Methoden der organischen Chemie [Methods of Organic Chemistry], Georg-Thieme-Verlag, Stuttgart), for example under reaction conditions which are known and suitable for the said reactions. Use can also be made here of variants known per se, which are not described here in greater detail.

Conventional work-up steps, such as, for example, addition of water to the reaction mixture and extraction, enable the compounds to be obtained after removal of the solvent. It may be advantageous, for further purification of the product, to follow this with a distillation or crystallisation or to carry out a chromatographic purification.

An acid of the formula I can be converted into the associated addition salt using a base, for example by reaction of equivalent amounts of the acid and base in an inert solvent, such as ethanol, and inclusive evaporation. Suitable bases for this reaction are, in particular, those which give physiologically acceptable salts. Thus, the acid of the formula I can be converted into the corresponding metal salt, in particular alkali or alkaline-earth metal salt, using a base (for example sodium hydroxide, potassium hydroxide, sodium carbonate or potassium carbonate) or into the corresponding ammonium salt. Organic bases which give physiologically acceptable salts, such as, for example, ethanolamine, are also suitable for this reaction.

On the other hand, a base of the formula I can be converted into the associated acid-addition salt using an acid, for example by reaction of equivalent amounts of the base and acid in an inert solvent, such as ethanol, with subsequent evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic, mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxysulfonic acid, benzenesulfonic acid, p-toluenesulfonic acid, naphthalenemom- and disulfonic acids or laurylsulfuric acid. Salts with physiologically unacceptable acids, for example picrates, can be used for the isolation and/or purification of the compounds of the formula I.

It has been found that the compounds of the formula I are well tolerated and have valuable pharmacological properties, since they selectively inhibit aspartyl proteases and in particular cathepsin D.

The invention therefore furthermore relates to the use of compounds according to the invention for the preparation of a medicament for the treatment and/or prophylaxis of diseases which are caused, promoted and/or propagated by cathepsin D and/or by cathepsin D-promoted signal transduction.

The invention thus also relates, in particular, to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states.

Particular preference is given, in particular, to physiological and/or pathophysiological states which are connected to cathepsin D.

Physiological and/or pathophysiological states are taken to mean physiological and/or pathophysiological states which are medically relevant, such as, for example, diseases or illnesses and medical disorders, complaints, symptoms or complications and the like, in particular diseases.

The invention furthermore relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of arthrosis, traumatic cartilage injuries and arthritis, in particular rheumatoid arthritis.

The invention furthermore relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of Alzheimer's disease, Huntington's disease, mucolipidosis, cancer, in particular breast cancer, contact dermatitis, late-onset hypersensitivity reaction, inflammation, endometriosis, scarring, benign prostate hyperplasia, osteosarcoma, rickets, skin diseases, such as, for example, psoriasis, immunological diseases, autoimmune diseases and immunodeficiency diseases.

In this connection, brain cancer, lung cancer, squamous cell cancer, bladder cancer, stomach cancer, pancreatic cancer, liver cancer, kidney cancer, colorectal cancer, breast cancer, head cancer, neck cancer, oesophageal cancer, gynaecological cancer, thyroid cancer, lymphomas, chronic leukaemia and acute leukaemia are to be regarded as cancerous diseases, all of which usually count amongst the group of hyperproliferative diseases.

Pain is a complex sensory perception which, as an acute event, has the character of a warning and control signal, but as chronic pain has lost this and in this case (as chronic pain syndrome) should be regarded and treated today as an independent syndrome. Hyperalgesia is the term used in medicine for excessive sensitivity to pain and reaction to a stimulus which is usually painful. Stimuli which can trigger pain are, for example, pressure, heat, cold or inflammation. Hyperalgesia is a form of hyperaesthesia, the generic term for excessive sensitivity to a stimulus. Allodynia is the term used in medicine for the sensation of pain which is triggered by stimuli which do not usually cause pain.

The invention thus furthermore relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological conditions, selected from the group consisting of pain, allodynia and hyperalgesia.

The invention thus particularly preferably relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological conditions, selected from the group consisting of arthrosis, traumatic cartilage injuries, arthritis, pain, allodynia and hyperalgesia.

It is intended that the medicaments disclosed above include a corresponding use of the compounds according to the invention for the preparation of a medicament for the treatment and/or prophylaxis of the above physiological and/or pathophysiological states.

It is additionally intended that the medicaments disclosed above include a corresponding method for the treatment and/or prophylaxis of the above physiological and/or pathophysiological states in which at least one compound according to the invention is administered to a patient in need of such a treatment.

The compounds according to the invention preferably exhibit an advantageous biological activity which can easily be demonstrated in enzyme assays and animal experiments, as described in the examples. In such enzyme-based assays, the antibodies according to the invention preferably exhibit and cause an inhibiting effect, which is usually documented by $IC_{50}$ values in a suitable range, preferably in the micromolar range and more preferably in the nanomolar range.

The compounds according to the invention can be administered to humans or animals, in particular mammals, such as apes, dogs, cats, rats or mice, and can be used in the therapeutic treatment of the human or animal body and in the combating of the above-mentioned diseases. They can furthermore be used as diagnostic agents or as reagents.

Furthermore, compounds according to the invention can be used for the isolation and investigation of the activity or expression of cathepsin D. In addition, they are particularly suitable for use in diagnostic methods for diseases in connection with disturbed cathepsin D activity. The invention therefore furthermore relates to the use of the compounds according to the invention for the isolation and investigation of the activity or expression of cathepsin D or as binders and inhibitors of cathepsin D.

For diagnostic purposes, the compounds according to the invention can, for example, be radioactively labelled. Examples of radioactive labels are $^3H$, $^{14}C$, $^{231}I$ and $^{125}I$. A preferred labelling method is the iodogen method (Fraker et al., 1978). In addition, the compounds according to the invention can be labelled by enzymes, fluorophores and chemophores. Examples of enzymes are alkaline phosphatase, β-galactosidase and glucose oxidase, an example of a fluorophore is fluorescein, an example of a chemophore is luminol, and automated detection systems, for example for fluorescent colorations, are described, for example, in U.S. Pat. No. 4,125,828 and U.S. Pat. No. 4,207,554.

The compounds of the formula I can be used for the preparation of pharmaceutical preparations, in particular by non-chemical methods. In this case, they are brought into a suitable dosage form together with at least one solid, liquid and/or semi-liquid excipient or adjuvant and optionally in combination with one or more further active compound(s).

The invention therefore furthermore relates to pharmaceutical preparations comprising at least one compound of the formula I and/or physiologically acceptable salts, derivatives, solvates and stereoisomers thereof, including mixtures thereof in all ratios. In particular, the invention also relates to pharmaceutical preparations which comprise further excipients and/or adjuvants, and also to pharmaceutical preparations which comprise at least one further medicament active compound.

In particular, the invention also relates to a process for the preparation of a pharmaceutical preparation, characterised in that a compound of the formula I and/or one of its physiologically acceptable salts, derivatives, solvates and stereoisomers, including mixtures thereof in all ratios, is brought into a suitable dosage form together with a solid, liquid or semi-liquid excipient or adjuvant and optionally with a further medicament active compound.

The pharmaceutical preparations according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient carriers, it is also possible to use, for example, lubricants, stabilisers and/or wetting agents, emulsifiers, salts for influencing the osmotic pressure, antioxidants, dispersants, antifoams, buffer substances, flavours and/or aromas or flavour correctants, preservatives, solubilisers or dyes. If desired, preparations or medicaments according to the invention may comprise one or more further active compounds, for example one or more vitamins.

If desired, preparations or medicaments according to the invention may comprise one or more further active compounds and/or one or more action enhancers (adjuvants).

The terms "pharmaceutical formulation" and "pharmaceutical preparation" are used as synonyms for the purposes of the present invention.

As used here, "pharmaceutically tolerated" relates to medicaments, precipitation reagents, excipients, adjuvants, stabilisers, solvents and other agents which facilitate the administration of the pharmaceutical preparations obtained therefrom to a mammal without undesired physiological side effects, such as, for example, nausea, dizziness, digestion problems or the like.

In pharmaceutical preparations for parenteral administration, there is a requirement for isotonicity, euhydration and tolerability and safety of the formulation (low toxicity), of the adjuvants employed and of the primary packaging. Surprisingly, the compounds according to the invention preferably have the advantage that direct use is possible and further purification steps for the removal of toxicologically unacceptable agents, such as, for example, high concentrations of organic solvents or other toxicologically unacceptable adjuvants, are thus unnecessary before use of the compounds according to the invention in pharmaceutical formulations.

The invention particularly preferably also relates to pharmaceutical preparations comprising at least one compound according to the invention in precipitated non-crystalline, precipitated crystalline or in dissolved or suspended form, and optionally excipients and/or adjuvants and/or further pharmaceutical active compounds.

The compounds according to the invention preferably enable the preparation of highly concentrated formulations without unfavourable, undesired aggregation of the compounds according to the invention occurring. Thus, ready-to-use solutions having a high active-ingredient content can be prepared with the aid of compounds according to the invention with aqueous solvents or in aqueous media.

The compounds and/or physiologically acceptable salts and solvates thereof can also be lyophilised and the resultant lyophilisates used, for example, for the preparation of injection preparations.

Aqueous preparations can be prepared by dissolving or suspending compounds according to the invention in an aqueous solution and optionally adding adjuvants. To this end, defined volumes of stock solutions comprising the said further adjuvants in defined concentration are advantageously added to a solution or suspension having a defined concentration of compounds according to the invention, and the mixture is optionally diluted with water to the pre-calculated concentration. Alternatively, the adjuvants can be added in solid form. The amounts of stock solutions and/or water which are necessary in each case can subsequently be added to the aqueous solution or suspension obtained. Compounds according to the invention can also advantageously be dissolved or suspended directly in a solution comprising all further adjuvants.

The solutions or suspensions comprising compounds according to the invention and having a pH of 4 to 10, preferably having a pH of 5 to 9, and an osmolality of 250 to 350 mOsmol/kg can advantageously be prepared. The pharmaceutical preparation can thus be administered directly substantially without pain intravenously, intra-arterially, intra-articularly, subcutaneously or percutaneously. In addition, the preparation may also be added to infusion solutions, such as, for example, glucose solution, isotonic saline solution or Ringer's solution, which may also contain further active compounds, thus also enabling relatively large amounts of active compound to be administered.

Pharmaceutical preparations according to the invention may also comprise mixtures of a plurality of compounds according to the invention. The preparations according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.).

For example, the compounds according to the invention can be stored in a stable manner by drying and when necessary converted into a ready-to-use pharmaceutical preparation by dissolution or suspension. Possible drying methods are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a medicament or of a pharmaceutical active compound which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improved treatment, healing, prevention or elimination of a disease, syndrome, disease state, complaint, disorder or prevention of side effects or also a reduction in the progress of a disease, complaint or disorder. The term "therapeutically effective amount" also encompasses the amounts which are effective for increasing normal physiological function.

On use of preparations or medicaments according to the invention, the compounds according to the invention and/or physiologically acceptable salts and solvates thereof are generally used analogously to known, commercially available preparations or preparations, preferably in dosages of between 0.1 and 500 mg, in particular 5 and 300 mg, per use unit. The daily dose is preferably between 0.001 and 250 mg/kg, in particular 0.01 and 100 mg/kg, of body weight. The preparation can be administered one or more times per day, for example two, three or four times per day. However, the individual dose for a patient depends on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active compound in an organism is its bioavailability. If the medicament active compound is delivered to the organism intravenously in the form of an injection solution, its absolute bioavailability, i.e. the proportion of the pharmaceutical which reaches the systemic blood, i.e. the major circulation, in unchanged form, is 100%. In the case of oral administration of a therapeutic active compound, the active compound is generally in the form of a solid in the formulation and must therefore first be dissolved in order that it is able to overcome the entry barriers, for example the gastrointestinal tract, the oral mucous membrane, nasal membranes or the skin, in particular the stratum corneum, or can be absorbed by the body. Data on the pharmacokinetics, i.e. on the bioavailability, can be obtained analogously to the method of J. Shaffer et al., J. Pharm. Sciences, 88 (1999), 313-318.

Furthermore, medicaments of this type can be prepared by means of one of the processes generally known in the pharmaceutical art. Medicaments can be adapted for administration via any desired suitable route, for example by the oral (including buccal or sublingual), rectal, pulmonary, nasal, topical (including buccal, sublingual or transdermal), vaginal or parenteral (including subcutaneous, intramuscular, intravenous, intradermal and in particular intra-articular) routes. Medicaments of this type can be prepared by means of all processes known in the pharmaceutical art by, for example, combining the active compound with the excipient(s) or adjuvant(s).

Parenteral administration is preferably suitable for administration of the medicaments according to the invention. In the case of parenteral administration, intra-articular administration is particularly preferred.

The invention thus preferably also relates to the use of a pharmaceutical preparation according to the invention for intra-articular administration in the treatment and/or prophylaxis of physiological and/or pathophysiological states selected from the group consisting of arthrosis, traumatic cartilage injuries, arthritis, pain, allodynia or hyperalgesia.

Intra-articular administration has the advantage that the compound according to the invention can be administered directly into the synovial fluid in the vicinity of the joint cartilage and is also able to diffuse from there into the cartilage tissue. Pharmaceutical preparations according to the invention can thus also be injected directly into the joint gap and thus develop their action directly at the site of action as intended. The compounds according to the invention are also suitable for the preparation of medicaments to be administered parenterally having slow, sustained and/or controlled release of active compound. They are thus also suitable for the preparation of delayed-release formulations, which are advantageous for the patient since administration is only necessary at relatively large time intervals.

The medicaments adapted to parenteral administration include aqueous and non-aqueous sterile injection solutions comprising antioxidants, buffers, bacteriostatics and solutes, by means of which the formulation is rendered isotonic with the blood or synovial fluid of the recipient to be treated; as well as aqueous and non-aqueous sterile suspensions, which can comprise suspension media and thickeners. The formulations can be delivered in single-dose or multi-dose containers, for example sealed ampoules and vials, and stored in the freeze-dried (lyophilised) state, so that only the addition of the sterile carrier liquid, for example water for injection purposes, immediately before use is necessary. Injection solutions and suspensions prepared in accordance with the formulation can be prepared from sterile powders, granules and tablets.

The compounds according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention can also be coupled to soluble polymers as targeted medicament excipients. Such polymers can encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds according to the invention can furthermore be coupled to a class of biodegradable polymers which are suitable for achieving slow release of a medicament, for example polylactic acid, poly-epsilon-caprolactone, polyhydroxybutyric acid, polyorthoesters, polyacetals, polydihydroxypyrans, poly-cyanoacrylates, polylactic-co-glycolic acid, polymers, such as conjugates between dextran and methacrylates, polyphosphoesters, various poly-saccharides and polyamines and poly-ε-caprolactone, albumin, chitosan, collagen or modified gelatine and crosslinked or amphipathic block copolymers of hydrogels.

Suitable for enteral administration (oral or rectal) are, in particular, tablets, dragees, capsules, syrups, juices, drops or suppositories, and suitable for topical use are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Also particularly suitable for topical uses are liposomal preparations.

In the case of formulation to give an ointment, the active compound can be employed either with a paraffinic or a water-miscible cream base. Alternatively, the active compound can be formulated to a cream with an oil-in-water cream base or a water-in-oil base.

Medicaments adapted to transdermal administration can be delivered as independent plasters for extended, close contact with the epidermis of the recipient. Thus, for example, the active compound can be supplied from the plaster by means of iontophoresis, as described in general terms in Pharmaceutical Research, 3(6), 318 (1986).

It goes without saying that, besides the constituents particularly mentioned above, the medicaments according to the invention may also comprise other agents usual in the art with respect to the particular type of pharmaceutical formulation.

The invention also relates to a set (kit) consisting of separate packs of
a) an effective amount of a compound of the formula I and/or physiologically acceptable salts, derivatives, solvates, prodrugs and stereoisomers thereof, including mixtures thereof in all ratios, and
b) an effective amount of a further medicament active compound.

The set comprises suitable containers, such as boxes or cartons, individual bottles, bags or ampoules. The set may, for example, comprise separate ampoules each containing an effective amount of a compound of the formula I and/or pharmaceutically acceptable salts, derivatives, solvates, prodrugs and stereoisomers thereof, including mixtures thereof in all ratios, and an effective amount of a further medicament active compound in dissolved or lyophilised form.

Furthermore, the medicaments according to the invention can be used in order to provide additive or synergistic effects in certain known therapies and/or can be used in order to restore the efficacy of certain existing therapies.

Besides the compounds according to the invention, the pharmaceutical preparations according to the invention may also comprise further medicament active compounds, for example for use in the treatment of arthrosis, other cathepsin D inhibitors, NSAIDS, Cox-2 inhibitors, glucocorticoids, hyaluronic acid, azathioprine, methotrexate, anti-CAM antibodies, such as, for example, anti-ICAM-1 antibody, FGF-18. For the treatment of the other diseases mentioned, the pharmaceutical preparations according to the invention may also, besides the compounds according to the invention, comprise further medicament active compounds which are known to the person skilled in the art in the treatment thereof.

The cancer treatment disclosed here can be carried out as therapy with a compound of the present invention or in combination with an operation, irradiation or chemotherapy. Chemotherapy of this type can include the use of one or more active compounds of the following categories of antitumour active compounds:

(i) antiproliferative/antineoplastic/DNA-damaging active compounds and combinations thereof, as used in medical oncology, such as alkylating active compounds (for example cis-platin, parboplatin, cyclophosphamide, nitrogen mustard, melphalan, chlorambucil, busulphan and nitrosoureas); antimetabolites (for example antifolates such as fluoropyrimidines such as 5-fluorouracil and tegafur, raltitrexed, methotrexate, cytosine arabinoside, hydroxyurea and gemcitabine); antitumour antibiotics (for example anthra-cyclines, such as adriamycin, bleomycin, doxorubicin, daunomycin, epi-rubicin, idarubicin, mitomycin-C, dactinomycin and mithramycin); antimitotic active compounds (for example vinca alkaloids, such as vincristine, vinblastine, vindesine and vinorelbine, and taxoids, such as taxol and taxotere); topoisomerase inhibitors (for example epipodophyllotoxins, such as etoposide and teniposide, amsacrine, topotecan, irinotecan and camptothecin) and cell-differentiating active compounds (for example all-trans-retinoic acid, 13-cis-retinoic acid and fenretinide);

(ii) cytostatic active compounds, such as anti-oestrogens (for example tamoxifen, toremifene, raloxifene, droloxifene and iodoxyfene), oestrogen receptor regulators (for example fulvestrant), anti-androgens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example anastrozole, letrozole, vorazole and exemestane) and inhibitors of 5α-reductase, such as finasteride;

(iii) active compounds which inhibit cancer invasion (for example metalloproteinase inhibitors, like marimastat, and inhibitors of urokinase plasminogen activator receptor function);

(iv) inhibitors of growth factor function, for example growth factor antibodies, growth factor receptor antibodies, for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033), for example inhibitors of the platelet-derived growth factor family and, for example, inhibitors of the hepatocyte growth factor family;

(v) anti-angiogenic active compounds, such as those which inhibit the effects of vascular endothelial growth factor (for example the anti-vascular endothelial cell growth factor antibody bevacizumab [Avastin™], compounds which have been published in the international patent applications WO 97/22596, WO 97/30035, WO 97/32856 and WO 98/13354) and compounds which act by another mechanism (for example linomide, inhibitors of integrin αvβ3 function and angiostatin);

(vi) vessel-destroying agents, such as combretastatin A4 and compounds which have been published in the international patent applications WO 99/02166, WO 00/40529, WO 00/41669, WO 01/92224, WO 02/04434 and WO 02/08213;

(vii) antisense therapies, for example those directed to the targets mentioned above, such as ISIS 2503, an anti-Ras antisense;

(viii) gene therapy approaches, including, for example, approaches for replacement of abnormal, modified genes, such as abnormal p53 or abnormal BRCA1 or BRCA2, GDEPT approaches (gene-directed enzyme pro-drug therapy), such as those which use cytosine deaminase, thymidine kinase or a bacterial nitroreductase enzyme, and approaches which increase the tolerance of a patient to chemotherapy or radiotherapy, such as multi-drug resistance therapy; and (ix) immunotherapy approaches, including, for example, ex-vivo and in-vivo approaches for increasing the immunogenicity of tumour cells of a patient, such as transfection with cytokines, such as interleukin 2, interleukin 4 or granulocyte macrophage colony stimulating factor, approaches for decreasing T-cell anergy, approaches using transfected immune cells, such as cytokine-transfected dendritic cells, approaches for use of cytokine-transfected tumour cells and approaches for use of anti-idiotypic antibodies.

The medicaments from Table 1 can preferably, but not exclusively, be combined with the compounds of the formula 1.

TABLE 1

| | | |
|---|---|---|
| Alkylating active compounds | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum active compounds | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson |
| | Tetraplatin | Matthey) |
| | Ormiplatin | BBR-3464 |
| | Iproplatin | (Hoffmann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |

TABLE 1-continued

| Category | | |
|---|---|---|
| | 6-Thioguanine | Decitabine (SuperGen) |
| | Cytarabine | Clofarabine (Bioenvision) |
| | 2-Fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic active compounds | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli Lilly) | Azaepothilon B (BMS) |
| | Vinflunine (Fabre) | BNP-7787 (BioNumerik) |
| | Auristatin PE (Teikoku Hormone) | CA-4-prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate Synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (isotope solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |

TABLE 1-continued

| | | |
|---|---|---|
| Histone acetyl transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) |
| Metalloproteinase inhibitors | Neovastat (Aeterna Laboratories)<br>Marimastat (British Biotech) | CMT-3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/ antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (ligand) | Alitretinoin (Ligand) |
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccines (CTL Immuno)<br>p21-RAS vaccine (GemVax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal active compounds | Oestrogens<br>Conjugated oestrogens<br>Ethynyloestradiol<br>Chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (En_treMed)<br>Arzoxifen (Eli Lilly) |
| Photodynamic active compounds | Talaporfin (Light Sciences)<br>Theralux (Theratechnologies)<br>Motexafin-Gadolinium (Pharmacyclics) | Pd bacteriopheophorbide (Yeda)<br>Lutetium texaphyrin (Pharmacyclics)<br>Hypericin |
| Tyrosine kinase inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various other active compounds | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB |

TABLE 1-continued

| | |
|---|---|
| G17DT immunogen (gastrin inhibitor, Aphton) | inhibitor, Active Biotech) |
| Efaproxiral (oxygenator, Allos Therapeutics) | Seocalcitol (vitamin D receptor agonist, Leo) |
| PI-88 (heparanase inhibitor, Progen) | 131-I-TM-601 (DNA antagonist, TransMolecular) |
| Tesmilifen (histamine antagonist, YM BioSciences) | Eflornithin (ODC inhibitor, ILEX Oncology) |
| Histamine (histamine H2 receptor agonist, Maxim) | Minodronic acid (osteoclast inhibitor, Yamanouchi) |
| Tiazofurin (IMPDH inhibitor, Ribapharm) | Indisulam (p53 stimulant, Eisai) |
| Cilengitide (integrin antagonist, Merck KGaA) | Aplidin (PPT inhibitor, PharmaMar) |
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | trans-Retinoic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

Even without further embodiments, it is assumed that a person skilled in the art will be able to use the above description in the broadest scope. The preferred embodiments should therefore merely be regarded as descriptive disclosure which is absolutely not limiting in any way.

The following examples are thus intended to explain the invention without limiting it. Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

Rf values on silica gel; mass spectrometry: EI (electron impact ionisation): $M^+$, FAB (fast atom bombardment): $(M+H)^{30}$, THF (tetrahydrofuran), NMP (N-methylpyrrolidone), DMSO (dimethyl sulfoxide), EA (ethyl acetate), MeOH (methanol), TLC (thin-layer chromatography)

The following substances have been synthesised and characterised. However, the preparation and characterisation of the substances can also be carried out by other methods for the person skilled in the art.

EXAMPLE 1: ILLUSTRATIVE COMPOUNDS OF THE FORMULA I

TABLE 2

| No. | Compound | Molecular weight | M + H | Ret [min] | Renin selectivity IC$_{50}$ see Example 6 | Stability in synovial fluid see Example 5 | CatD assay IC$_{50}$ (M) see Example 3 (mol/l) | GAG assay IC$_{50}$ (M) see Example 4 |
|---|---|---|---|---|---|---|---|---|
| 1 | Benzyl (S)-2-((2S,3S)-2-{(3S,4S)-3-hydroxy-4-[(S)-3-methyl-2-(3-phenylpropionylamino)-butyrylamino]-5-phenylpentanoyl-amino}-3-methylpentanoylamino)-3-methylbutyrate | 743.0 | 744.0 | 2.71 | >30 μM | | 7.90E−08 | |
| 2 | Benzyl (S)-2-((2S,3S)-2-{(3S,4S)-3-hydroxy-4-[(S)-3-methyl-2-(4-phenylbutyrylamino)butyrylamino]-5-phenylpentanoylamino}-3-methylpentanoylamino)-3-methylbutyrate | 757.0 | 758.0 | 2.78 | | | 7.10E−08 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 3 | Benzyl (S)-2-[(2S,3S)-2-((3S,4S)-3-hydroxy-4-((S)-3-methyl-2-[2-methyl-2-(naphthalen-2-yloxy)-propionylamino]butyryl-amino)-5-phenylpentanoylamino)-3-methylbutyrate | 823.0 | 824.0 | 3.01 | >30 μM | | 2.30E-07 | |
| 4 | (S)-2-((2S,3S)-2-((3S,4S)-3-Hydroxy-4-[(S)-3-methyl-2-(3-phenylpropionylamino)-butyrylamino]-5-phenylpentanoylamino)-3-methylpentanoylamino)-3-methylbutyric acid | 652.8 | 653.8 | 2.27 | | stable | 3.00E-08 | 6.06E-08 |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 5 | (S)-2-((2S,3S)-2-{(3S,4S)-3-Hydroxy-4-[(S)-3-methyl-2-(4-phenylbutyrylamino)butyryl-amino]-5-phenylpentanoylamino}-3-methyl-pentanoylamino)-3-methylbutyric acid | 666.9 | 667.9 | 2.36 | 20 µM | stable | 3.41E−08 | 9.89E−07 |
| 6 | (S)-2-[((2S,3S)-2-((3S,4S)-3-Hydroxy-4-{(S)-3-methyl-2-[2-methyl-2-(naphthalen-2-yloxy)-propionylamino]butyrylamino}-5-phenylpentanoylamino)-3-methyl-pentanoylamino]-3-methylbutyric acid | 732.9 | 733.9 | 2.61 | | | 2.30E−07 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 7 | 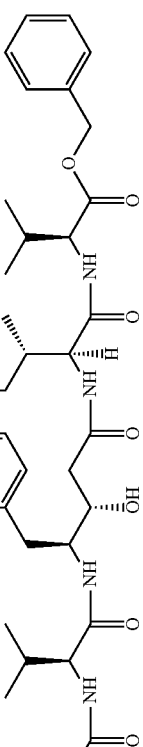 (S)-2-[(2S,3S)-2-((3S,4S)-3-Hydroxy-4-((S)-3-methyl-2-[2-(naphthalen-2-yloxy)acetyl-amino]butyrylamino)-5-phenylpentanoyl-amino)-3-methylpentanoylamino]-3-methyl-butyric acid | 795.0 | 796.0 | 2.83 | | | 3.50E−07 | |
| 8 | 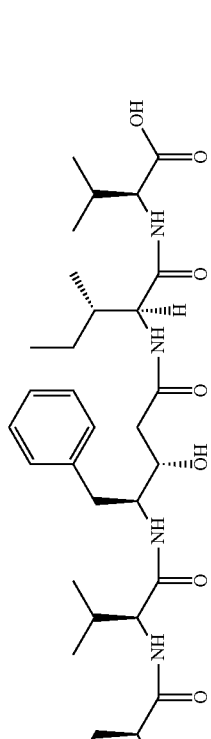 (S)-2-[(2S,3S)-2-((3S,4S)-3-Hydroxy-4-((S)-3-methyl-2-[(S)-4-methyl-2-(3-methylbutyryl-amino)pentanoylamino]butyrylamino)-5-phenylpentanoylamino)-3-methylpentanoyl-amino]-3-methylbutyric acid | 717.9 | 718.9 | 2.27 | | | 3.00E−09 | 2.76E−09 |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 9 | 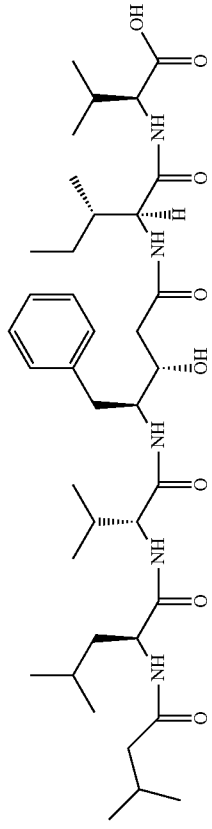 (S)-2-[(2S,3S)-2-((3S,4S)-3-Hydroxy-4-((R)-3-methyl-2-[(S)-4-methyl-2-(3-methylbutyryl-amino)pentanoylamino]-5-phenylpentanoylamino)-3-methylbutyryl-amino]-3-methylbutyric acid | 717.9 | 718.9 | 2.3 | | | 7.51E−08 | 3.12E−08 |
| 10 | 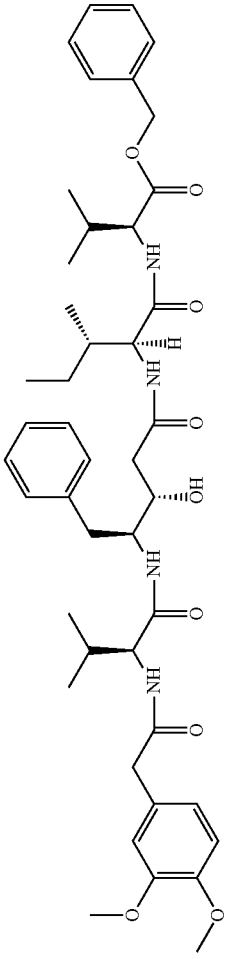 Benzyl (S)-2-[(2S,3S)-2-((3S,4S)-4-((S)-2-[2-(3,4-dimethoxyphenyl)acetylamino]-3-methyl-butyrylamino)-3-hydroxy-5-phenylpentanoyl-amino)-3-methylbutyrylamino]-3-methyl-butyrate | 789.0 | 790.0 | 2.54 | | | 2.90E−08 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 11 | Benzyl (S)-2-[(2S,3S)-2-((3S,4S)-3-hydroxy-4-{(S)-2-[2-(4-methoxyphenyl)acetylamino]-3-methylbutyrylamino}-5-phenylpentanoylamino)-3-methylpentanoylamino]-3-methylbutyrate | 759.0 | 760.0 | 2.62 | | | 9.00E−08 | |
| 12 | Benzyl (S)-2-[(2S,3S)-2-((3S,4S)-4-{(S)-2-[2-(3-ethoxyphenyl)acetylamino]-3-methylbutyrylamino}-3-hydroxy-5-phenylpentanoylamino)-3-methylpentanoylamino]-3-methylbutyrate | 773.0 | 774.0 | 2.72 | | | 2.50E−08 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 13 | Benzyl (S)-2-[(2S,3S)-2-((3S,4S)-3-hydroxy-4-{(S)-2-[2-(3-methoxyphenyl)acetylamino]-3-methylbutyrylamino}-5-phenylpentanoyl-amino)-3-methylpentanoylamino]-3-methyl-butyrate | 759.0 | 760.0 | 2.64 | | | 2.50E−08 | |
| 14 | (S)-2-[(2S,3S)-2-((3S,4S)-4-{(S)-2-[2-(3,4-Dimethoxyphenyl)acetylamino]-3-methyl-butyrylamino}-3-hydroxy-5-phenylpentanoyl-amino)-3-methylpentanoylamino]-3-methyl-butyric acid | 698.9 | 699.9 | 2.08 | | | 1.50E−07 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 15 | (S)-2-[(2S,3S)-2-((3S,4S)-3-Hydroxy-4-((S)-2-[2-(4-methoxyphenyl)acetylamino]-3-methylbutyrylamino)-5-phenylpentanoyl-amino)-3-methylpentanoylamino]-3-methyl-butyric acid | 668.8 | 669.8 | 2.18 | >30μM | | 3.90E−08 | |
| 16 | Benzyl (S)-2-((2S,3S)-2-((3S,4S)-3-hydroxy-4-[(S)-3-methyl-2-(2-naphthalen-2-yl acetylamino)-butyrylamino]-5-phenylpentanoyl-amino}-3-methylpentanoylamino)-3-methylbutyrate | 779.0 | 780.0 | 2.78 | | | 1.50E−07 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 17 | 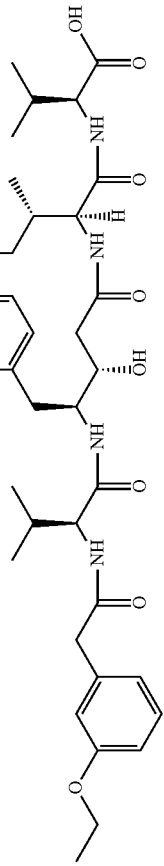<br>(S)-2-[(2S,3S)-2-((3S,4S)-4-((S)-2-[2-(3-Ethoxyphenyl)acetylamino]-3-methylbutyrylamino)-3-hydroxy-5-phenylpentanoylamino]-3-methyl-pentanoylamino]-3-methylbutyric acid | 682.9 | 683.9 | 2.28 | | | 1.55E−08 | |
| 18 | 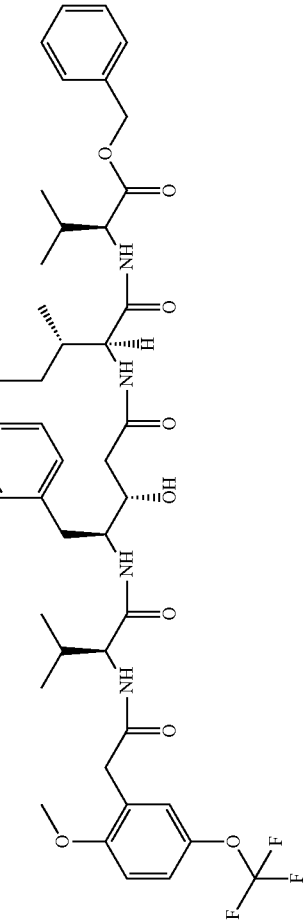<br>Benzyl (S)-2-[(2S,3S)-2-((3S,4S)-3-hydroxy-4-((S)-2-[2-(2-methoxy-5-trifluoromethoxyphenyl)acetyl-amino]-3-methylbutyrylamino)-5-phenylpentanoylamino)-3-methyl-pentanoylamino]-3-methylbutyrate | 842.9 | 843.9 | 2.82 | | | 3.40E−08 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 19 | Benzyl (S)-2-[(2S,3S)-2-((3S,4S)-3-hydroxy-4-{(S)-3-methyl-2-[2-(3-phenoxyphenyl)acetylamino]-butyrylamino}-5-phenylpentanoyl-amino)-3-methylpentanoylamino]-3-methylbutyrate | 821.0 | 822.0 | 2.86 | | | 4.00E−08 | |
| 20 | (S)-2-[(2S,3S)-2-((3S,4S)-3-Hydroxy-4-{(S)-2-[2-(3-methoxy-phenyl)acetylamino]-3-methyl-butyrylamino}-5-phenylpentanoyl-amino)-3-methylpentanoylamino]-3-methylbutyric acid | 668.8 | 669.8 | 2.19 | | stable | 1.20E−08 | 4.79E−08 |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 21 | Benzyl (S)-2-{(2S,3S)-2-{(3S,4S)-3-hydroxy-4-[(S)-3-methyl-2-(2-naphthalen-1-ylacetylamino)-butyrylamino]-5-phenylpentanoyl-amino}-3-methylpentanoylamino]-3-methylbutyrate | 779.0 | 780.0 | 2.78 | | | 1.20E−06 | |
| 22 | Benzyl (S)-2-[(2S,3S)-2-{(3S,4S)-3-hydroxy-4-{(S)-2-[2-(2-methoxy-phenyl)acetylamino]-3-methyl-butyrylamino}-5-phenylpentanoyl-amino}-3-methylpentanoylamino]-3-methylbutyrate | 759.0 | 760.0 | 2.67 | | | 2.10E−07 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 23 | 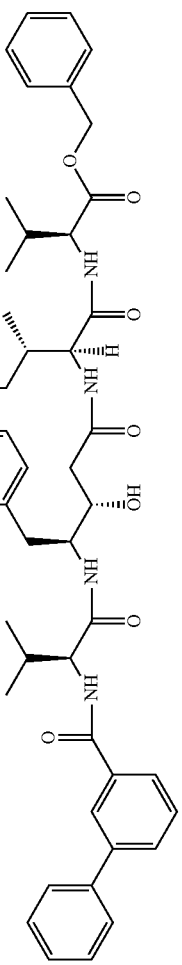<br>Benzyl (S)-2-[(2S,3S)-2-((3S,4S)-4-{(S)-2-[(biphenyl-3-carbonyl)amino]-3-methylbutyrylamino}-3-hydroxy-5-phenylpentanoylamino)-3-methyl-pentanoylamino]-3-methylbutyrate | 791.0 | 792.0 | 2.87 | | | 1.20E-05 | |
| 24 | 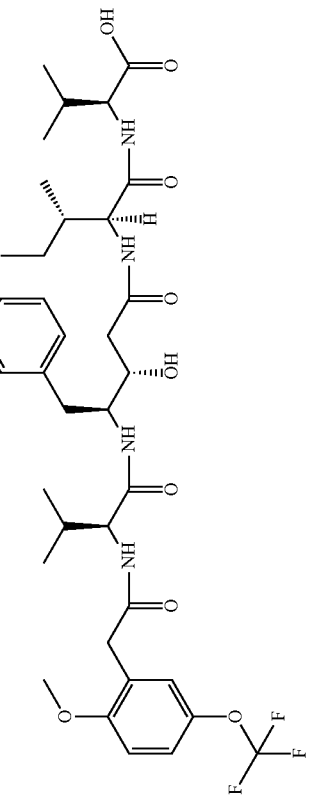<br>(S)-2-[(2S,3S)-2-((3S,4S)-3-Hydroxy-4-{(S)-2-[2-(2-methoxy-5-trifluoromethoxyphenyl)acetyl-amino]-3-methylbutyrylamino}-5-phenylpentanoylamino)-3-methyl-pentanoylamino]-3-methylbutyric acid | 752.8 | 753.8 | 2.41 | | | 1.10E-08 | |

TABLE 2-continued

| No. | Compound | | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|---|
| 25 | | (S)-2-((2S,3S)-2-((3S,4S)-3-Hydroxy-4-[(S)-3-methyl-2-(2-naphthalen-2-ylacetylamino)-butyrylamino]-5-phenylpentanoyl-amino)-3-methylpentanoylamino)-3-methylbutyric acid | 688.9 | 689.9 | 2.35 | | | 8.10E−09 | |
| 26 | | (S)-2-((2S,3S)-2-((3S,4S)-4-[(S)-2-(3-tert-Butoxybenzoylamino)-3-methylbutyrylamino]-3-hydroxy-5-phenylpentanoylamino)-3-methylpentanoylamino)-3-methylbutyric acid | 696.9 | 697.9 | 2.41 | | | 1.20E−07 | |

TABLE 2-continued

| No. | Compound | | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|---|
| 27 | | (S)-2-[(2S,3S)-2-((3S,4S)-3-Hydroxy-4-{(S)-3-methyl-2-[2-(3-phenoxyphenyl)acetylamino]-butyrylamino}-5-phenylpentanoyl-amino)-3-methylpentanoylamino]-3-methylbutyric acid | 730.9 | 731.9 | 2.46 | | | 1.20E−08 | |
| 28 | | (S)-2-[(2S,3S)-2-((3S,4S)-3-Hydroxy-4-{(S)-2-[2-(2-methoxyphenyl)acetylamino]-3-methyl-butyrylamino}-5-phenylpentanoyl-amino)-3-methylpentanoylamino]-3-methylbutyric acid | 668.8 | 669.8 | 2.21 | >30 μM | | 1.60E−07 | |

TABLE 2-continued

| No. | Compound | Molecular weight | M + H | Ret [min] | Renin selectivity IC₅₀ see Example 6 | Stability in synovial fluid see Example 5 | CatD assay IC₅₀(M) see Example 3 (mol/l) | GAG assay IC₅₀(M) see Example 4 |
|---|---|---|---|---|---|---|---|---|
| 29 | (S)-2-[(2S,3S)-2-((3S,4S)-4-{(S)-2-[2-(3,4-Dimethylphenoxy)acetylamino]-3-methylbutyrylamino}-3-hydroxy-5-phenylpentanoylamino)-3-methylpentanoylamino]-3-methylbutyric acid | 682.9 | 683.9 | 2.42 | | | 1.00E−07 | |
| 30 | (S)-2-((2S,3S)-2-{(3S,4S)-3-Hydroxy-4-[(S)-3-methyl-2-(2-naphthalen-1-ylacetylamino)butyrylamino]-5-phenylpentanoylamino}-3-methylpentanoylamino)-3-methylbutyric acid | 688.9 | 689.9 | 2.36 | | | 8.50E−08 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 31 | 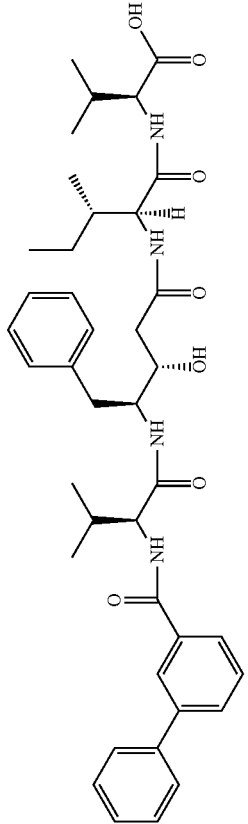 (S)-2-[(2S,3S)-2-((3S,4S)-4-((S)-2-[(Biphenyl-3-carbonyl)amino]-3-methylbutyrylamino)-3-hydroxy-5-phenylpentanoylamino)-3-methyl-pentanoylamino]-3-methylbutyric acid | 700.9 | 701.9 | 2.47 | | | 1.60E−07 | |
| 32 | 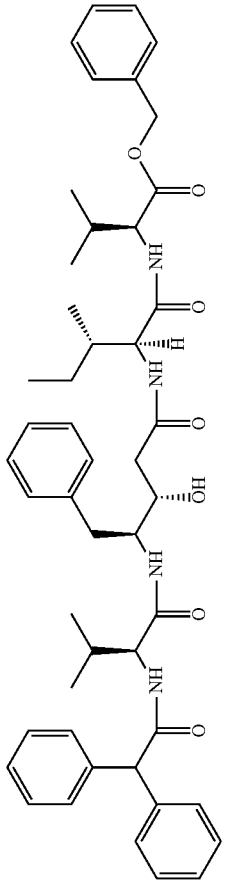 Benzyl (S)-2-[(2S,3S)-2-[(3S,4S)-4-((S)-2-diphenylacetylamino-3-methylbutyrylamino)-3-hydroxy-5-phenylpentanoylamino]-3-methyl-pentanoylamino]-3-methylbutyrate | 805.0 | 806.0 | 2.87 | | | 3.20E−07 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$ (M) see Example 3 (mol/l) | GAG assay IC$_{50}$ (M) see Example 4 |
|---|---|---|---|---|---|---|---|---|
| 33 | (S)-2-((2S,3S)-2-[(3S,4S)-4-((S)-2-Diphenylacetylamino-3-methyl-butyrylamino)-3-hydroxy-5-phenyl-pentanoylamino]-3-methylbutyric acid | 714.9 | 715.9 | 2.44 | | | 1.60E−08 | |
| 34 | Benzyl (S)-2-[(2S,3S)-2-((3S,4S)-4-{(S)-2-[2-(3-ethoxyphenyl)acetyl-amino]-3-methyl-1-(S)-oxopentylamino}-3-hydroxy-5-phenylpentanoylamino)-3-methyl-pentanoylamino]-3-methylbutyrate | 787.0 | 788.0 | 2.8 | | | 2.70E−07 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 35 | 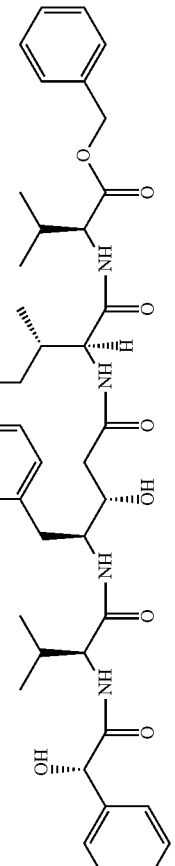<br>Benzyl (S)-2-((2S,3S)-2-((3S,4S)-3-hydroxy-4-[(S)-2-((S)-2-hydroxy-2-phenylacetylamino)-3-methylbutyryl-amino]-5-phenylpentanoylamino)-3-methylpentanoylamino)-3-methyl-butyrate | 744.9 | 745.9 | 2.56 | | | 5.80E−07 | |
| 36 | 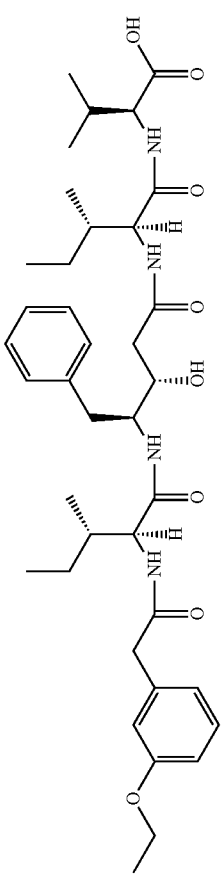<br>(S)-2-[(2S,3S)-2-((3S,4S)-3-Hydroxy-4-((S)-methyl-1-(S)-2-[2-(3-ethoxyphenyl)acetylamino]-3-oxopentylamino)-5-phenylpentanoyl-amino)-3-methylpentanoylamino]-3-methylbutyric acid | 696.9 | 697.9 | 2.35 | | | 4.30E−08 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 37 | 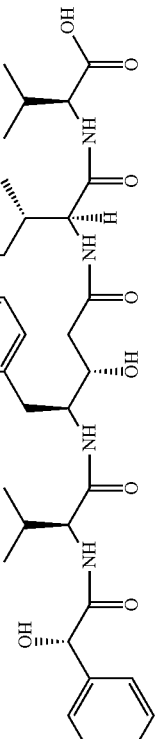<br>(S)-2-((2S,3S)-2-((3S,4S)-3-Hydroxy-4-[(S)-2-((S)-2-hydroxy-2-phenylacetylamino)-3-methylbutyryl-amino]-5-phenylpentanoylamino}-3-methylpentanoylamino)-3-methyl-butyric acid | 654.8 | 655.8 | 2.13 | | | 3.10E-07 | |
| 38 | 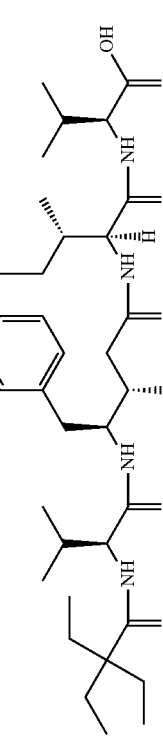<br>(S)-2-((2S,3S)-2-((3S,4S)-4-[(S)-2-(2,2-Diethylbutyrylamino)-3-methyl-butyrylamino]-3-hydroxy-5-phenyl-pentanoylamino}-3-methyl-pentanoylamino)-3-methylbutyric acid | 646.9 | 647.9 | 2.45 | | | 7.00E-06 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 39 | 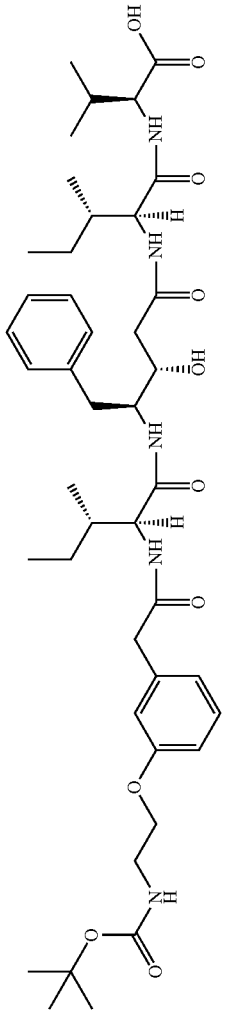 (S)-2-{(2S,3S)-2-[(3S,4S)-4-((S)-2-{2-[3-(2-tert-Butoxycarbonylamino-ethoxy)phenyl]acetylamino}-3-methyl-1-(S)-oxopentylamino)-3-hydroxy-5-phenylpentanoylamino]-3-methylpentanoylamino}-3-methylbutyric acid | 812.0 | 813.0 | 2.4 | | | 3.90E−08 | |
| 40 | 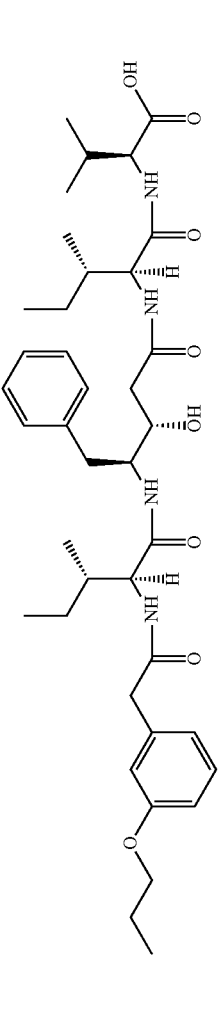 (S)-2-[(2S,3S)-2-((3S,4S)-3-Hydroxy-4-((2S,3S)-3-methyl-2-{2-(3-propoxyphenyl)acetylamino]-pentanoylamino)-5-phenyl-pentanoylamino)-3-methyl-pentanoylamino]-3-methylbutyric acid | 710.9 | 711.9 | 2.46 | | | 1.70E−08 | |

TABLE 2-continued

| No. | Compound | Molecular weight | M + H | Ret [min] | Renin selectivity IC50 see Example 6 | Stability in synovial fluid see Example 5 | CatD assay IC50(M) see Example 3 (mol/l) | GAG assay IC50(M) see Example 4 |
|---|---|---|---|---|---|---|---|---|
| 41 | 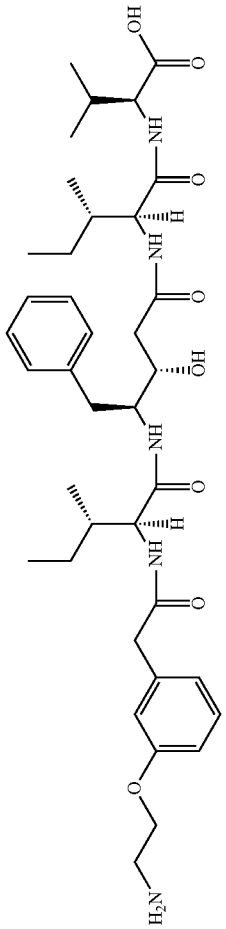<br>(S)-2-((2S,3S)-2-[(3S,4S)-4-((S)-2-{2-[3-(2-Aminoethoxy)phenyl]acetyl-amino}-3-methyl-1-(S)-oxopentylamino)-3-hydroxy-5-phenylpentanoylamino]-3-methyl-pentanoylamino)-3-methylbutyric acid | 711.9 | 712.9 | 1.7 | | | 4.80E−07 | |
| 42 | 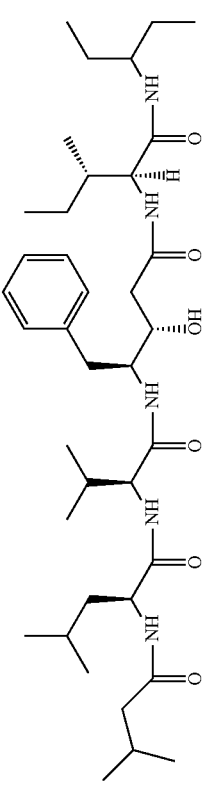<br>N-[(1S,2S)-1-(1-Ethylpropylcarbamoyl)-2-methyl-butyl]-(2S,5S)-3-hydroxy-4-((S)-3-methyl-2-[(S)-4-methyl-2-(3-methyl-butyrylamino)pentanoylamino]-butyrylamino)-5-phenylpentanamide | 687.9 | 689.0 | 2.57 | | | 1.3E−09 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 43 | N-[(1S,2S)-1-(1-Ethylpropyl)carbamoyl)-2-methyl-butyl]-(2S,5S)-3-hydroxy-4-[(S)-3-methyl-2-((S)-4-methyl-2-phenylacetylaminopentanoylamino)-1-oxobutylamino]-5-phenylpentanamide | 721.98 | 723.0 | 2.57 | | | 3.5E-09 | |
| 44 | Benzyl (S)-2-((2S,3S)-2-((3S,4S)-3-hydroxy-4-[(S)-3-methyl-2-((S)-4-methyl-2-phenylacetylamino-pentanoylamino)butyrylamino]-5-phenylpentanoylamino)-3-methyl-pentanoylamino)-3-methylbutyrate | 842.08 | 843.1 | 2.76 | | | 2.1E-09 | |

TABLE 2-continued

| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 45 | 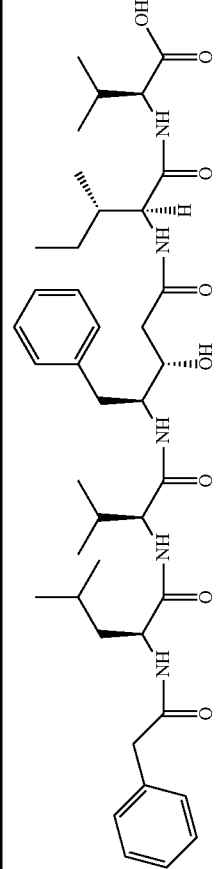 (S)-2-((2S,3S)-2-((3S,4S)-3-Hydroxy-4-[(S)-3-methyl-2-((S)-4-methyl-2-phenylacetylamino-pentanoyl]amino}butyrylamino)-5-phenylpentanoylamino)-3-methyl-pentanoylamino)-3-methylbutyric acid | 751.96 | 753.0 | 2.33 | | | 3.5E−10 | |
| 46 | 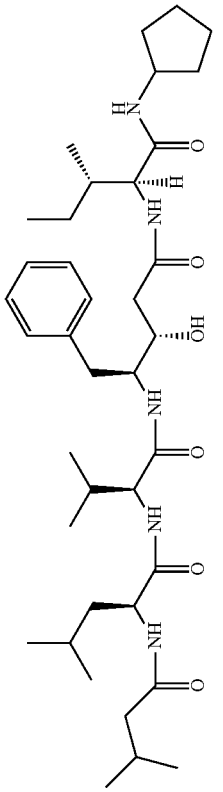 N-((1S,2S)-1-Cyclopentylcarbamoyl-2-methylbutyl)-(2S,5S)-3-hydroxy-4-{(S)-3-methyl-2-[(S)-4-methyl-2-(3-methylbutyrylamino)pentanoyl-amino]butyrylamino}-5-phenylpentanamide | 685.94 | 686.9 | 2.5 | | | 1.8E−09 | |

TABLE 2-continued

| No. | Compound | Molecular weight | M + H | Ret [min] | Renin selectivity IC₅₀ see Example 6 | Stability in synovial fluid see Example 5 | CatD assay IC₅₀(M) see Example 3 (mol/l) | GAG assay IC₅₀(M) see Example 4 |
|---|---|---|---|---|---|---|---|---|
| 47 | N-[(S)-1-(1-Ethylpropylcarbamoyl)-2-methylpropyl]-(3S,4S)-3-hydroxy-4-((S)-3-methyl-2-[(S)-4-methyl-2-(3-methylbutyrylamino)pentanoyl-amino]butyrylamino)-5-phenylpentanamide | 673.93 | 674.9 | 2.46 | | | 6.5E-10 | |
| 48 | N-[(S)-1-(1-Ethylpropylcarbamoyl)-butyl]-(3S,4S)-3-hydroxy-4-((S)-3-methyl-2-[(S)-4-methyl-2-(3-methylbutyrylamino)pentanoylamino]-butyrylamino)-5-phenylpentanamide | 673.93 | 674.9 | 2.47 | | | 2.6E-10 | |

TABLE 2-continued
| No. | Compound | Molecular weight | M + H | Ret [min] | Renin selectivity IC$_{50}$ see Example 6 | Stability in synovial fluid see Example 5 | CatD assay IC$_{50}$(M) see Example 3 (mol/l) | GAG assay IC$_{50}$(M) see Example 4 |
|---|---|---|---|---|---|---|---|---|
| 49 | 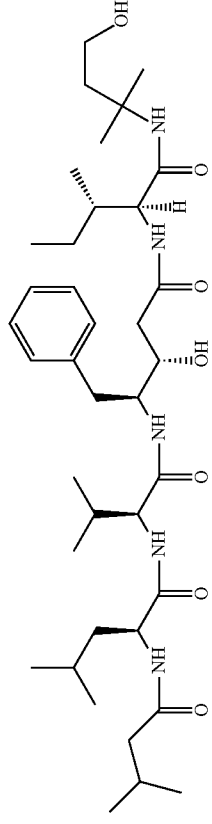<br>N-[(1S,2S)-1-(3-Hydroxy-1,1-dimethylpropylcarbamoyl)-2-methyl-butyl]-(3S,4S)-3-hydroxy-4-((S)-3-methyl-2-[(S)-4-methyl-2-(3-methyl-butyrylamino)pentanoylamino]-butyrylamino)-5-phenylpentanamide | 703.96 | 705.0 | 2.26 | | | 2.1E-10 | |

In order to avoid any doubt, in all cases where the chemical name of a compound according to the invention and the depiction of the chemical structure of a compound according to the invention mistakenly do not agree, the compound according to the invention is defined unambiguously by the depiction of the chemical structure.

The mass signals were determined on an Agilent 1200 instrument: Chromolith Speed Rod RP 18e 50-4.6 mm LCMS; polar.m, 2.4 ml/min, 220 nm, buffer A 0.05% of HCOOH/H2O, buffer B 0.04% of HCOOH/ACN, 0.0-2.8 min 4%-100% of buffer B; 2.8-3.3 min 100% of buffer B 3.3-3.4 min 100%-4% of buffer B The retention times were determined on a Merck-Hitachi LaChrom instrument:

Chromolith Speed Rod RP18e-100-4.6 HPLC; 5 min 4 ml 215 nm; 4 ml/min, 215 nm, buffer A 0.05% of TFA/H2O, buffer B 0.04% of TFA/ACN, 0.0-0.2 min 5% of buffer B; 0.2-5.0 min 5%-100% of buffer B; 5.0-5.5 min 99%-5% of buffer B NMR Data

TABLE 3

| No. | Compound | NMR data |
|---|---|---|
| 1 | Benzly (S)-2-((2S,3S)-2-{(3S,4S)-3-hydroxy-4-[(S)-3-methyl-2-(3-phenyl-propionylamino)-butyrylamino]-5-phenylpentanoyl-amino}-3-methyl-pentanoylamino)-3-methylbutyrate | 1H NMR (500 MHz, DMSO) ppm = 8.16 (d, J = 7.7, 1H), 7.77 (d, J = 8.7, 1H), 7.70 (d, J = 8.8, 1H), 7.60 (d, J = 8.8, 1H), 7.40-7.28 (m, 5H), 7.28-7.10 (m, 10H), 5.10 (s, 2H), 5.06 (d, J = 5.3, 1H), 4.32-4.25 (m, 1H), 4.21-4.14 (m, 1H), 4.12-4.04 (m, 1H), 3.98-3.89 (m, 1H), 3.89-3.81 (m, 1H), 2.89-2.73 (m, 3H), 2.64-2.56 (m, 1H), 2.49-2.35 (m, 2H), 2.30-2.21 (m, 1H), 2.17-1.99 (m, 2H), 1.92-1.81 (m, 1H), 1.72-1.62 (m, 1H), 1.47-1.38 (m, 1H), 1.11-0.98 (m, 1H), 0.90-0.82 (m, 6H), 0.81-0.70 (m, 12H). |
| 2 | Benzly (S)-2-((2S,3S)-2-{(3S,4S)-3-hydroxy-4-[(S)-3-methyl-2-(4-phenyl-butyrylamino)butyryl-amino]-5-phenyl-pentanoylamino}-3-methylpentanoyl-amino)-3-methyl-butyrate | 1H NMR (400 MHz, DMSO) ppm = 8.17 (d, J = 7.8, 1H), 7.75 (d, J = 8.8, 1H), 7.71 (d, J = 8.8, 1H), 7.60 (d, J = 8.8, 1H), 7.41-7.23 (m, 7H), 7.23-7.05 (m, 8H), 5.10 (s, 2H), 5.06 (d, J = 5.4, 1H), 4.33-4.24 (m, 1H), 4.21-4.13 (m, 1H), 4.08 (dd, J = 8.8, 7.2, 1H), 3.99-3.80 (m, 2H), 2.89-2.78 (m, 1H), 2.65-2.49 (m, 3H), 2.30-1.98 (m, 5H), 1.96-1.61 (m, 4H), 1.48-1.35 (m, 1H), 1.12-0.96 (m, 1H), 0.89-0.71 (m, 18H). |
| 3 | Benzly (S)-2-[(2S,3S)-2-((3S,4S)-3-hydroxy-4-{(S)-3-methyl-2-[2-methyl-2-(naphthalen-2-yloxy)-propionylamino]-butyrylamino}-5-phenylpentanoyl-amino)-3-methyl-pentanoylamino]-3-methylbutyrate | 1H NMR (500 MHz, DMSO) ppm = 8.15 (d, J = 7.8, 1H), 7.85-7.67 (m, 6H), 7.47-7.28 (m, 7H), 7.26 (d, J = 2.4, 1H), 7.24-7.08 (m, 6H), 5.13 (d, J = 4.7, 1H), 5.10 (s, 2H), 4.32-4.25 (m, 1H), 4.21-4.08 (m, 2H), 4.03-3.94 (m, 1H), 3.91-3.83 (m, 1H), 2.88-2.80 (m, 1H), 2.65-2.56 (m, 1H), 2.27-2.18 (m, 1H), 2.17-2.09 (m, 1H), 2.09-1.99 (m, 1H), 1.96-1.86 (m, 1H), 1.73-1.61 (m, 1H), 1.51 (s, 3H), 1.47 (s, 4H), 1.10-0.97 (m, 1H), 0.88-0.72 (m, 12H), 0.65 (d, J = 6.7, 6H). |
| 4 | (S)-2-((2S,3S)-2-{(3S,4S)-3-Hydroxy-4-[(S)-3-methyl-2-(3-phenyl-propionylamino)-butyrylamino]-5-phenylpentanoyl-amino}-3-methyl-pentanoylamino)-3-methylbutyric acid | 1H NMR (400 MHz, DMSO) ppm = 12.49 (s, 1H), 7.92 (d, J = 8.1, 1H), 7.79 (d, J = 8.8, 1H), 7.71 (d, J = 8.8, 1H), 7.64 (d, J = 8.8, 1H), 7.29-7.10 (m, 10H), 5.09 (d, J = 5.4, 1H), 4.32-4.23 (m, 1H), 4.13-4.04 (m, 2H), 3.99-3.82 (m, 2H), 2.91-2.72 (m, 3H), 2.66-2.55 (m, 1H), 2.50-2.34 (m, 2H), 2.31-2.20 (m, 1H), 2.18-1.96 (m, 2H), 1.93-1.80 (m, 1H), 1.76-1.65 (m, 1H), 1.50-1.33 (m, 1H), 1.09-1.00 (m, 1H), 0.92-0.70 (m, 18H). |
| 5 | (S)-2-((2S,3S)-2-{(3S,4S)-3-Hydroxy-4-[(S)-3-methyl-2-(4-phenylbutyrylamino)-butyrylamino]-5-phenylpentanoyl-amino}-3-methyl-pentanoylamino)-3-methylbutyric acid | 1H NMR (400 MHz, DMSO) ppm = 12.48 (s, 1H), 7.91 (d, J = 8.2, 1H), 7.79-7.67 (m, 2H), 7.62 (d, J = 8.7, 1H), 7.31-7.05 (m, 10H), 5.07 (s, 1H), 4.31-4.22 (m, 1H), 4.13-4.03 (m, 2H), 3.99-3.82 (m, 2H), 2.93-2.81 (m, 1H), 2.66-2.50 (m, 3H), 2.30-2.09 (m, 4H), 2.09-1.97 (m, 1H), 1.97-1.64 (m, 4H), 1.51-1.37 (m, 1H), 1.09-1.01 (m, 1H), 0.91-0.74 (m, 18H). |
| 6 | (S)-2-[(2S,3S)-2-((3S,4S)-3-Hydroxy-4-{(S)-3-methyl-2-[2-methyl-2-(naphthalen-2-yloxy)-propionylamino]-butyrylamino}-5-phenylpentanoyl-amino)-3-methyl- | 1H NMR (500 MHz, DMSO) ppm = 12.49 (s, 1H), 7.91-7.67 (m, 6H), 7.47-7.34 (m, 2H), 7.26 (d, J = 2.4, 1H), 7.24-7.09 (m, 7H), 5.17 (s, 1H), 4.30-4.23 (m, 1H), 4.15-4.04 (m, 2H), 4.02-3.94 (m, 1H), 3.89 (d, J = 8.3, 1H), 2.90-2.82 (m, 1H), 2.65-2.57 (m, 1H), 2.27-2.18 (m, 1H), 2.18-2.11 (m, 1H), 2.08-1.97 (m, 1H), 1.97-1.86 (m, 1H), 1.75-1.65 (m, 1H), |

TABLE 3-continued

| No. | Compound | NMR data |
|---|---|---|
| | pentanoylamino]-3-methylbutyric acid | 1.51 (s, 3H), 1.49-1.32 (m, 4H), 1.09-1.00 (m, 1H), 0.89-0.75 (m, 12H), 0.65 (d, J = 6.7, 6H). |
| 7 | (S)-2-[(2S,3S)-2-((3S,4S)-3-Hydroxy-4-{(S)-3-methyl-2-[2-(naphthalen-2-yloxy)-acetylamino]butyryl-amino}-5-phenyl-pentanoylamino)-3-methylpentanoyl-amino]-3-methyl-butyric acid | 1H NMR (500 MHz, DMSO) ppm = 8.15 (d, J = 7.7, 1H), 7.88-7.81 (m, 4H), 7.77-7.70 (m, 2H), 7.48-7.41 (m, 1H), 7.40-7.15 (m, 12H), 7.15-7.07 (m, 1H), 5.10 (s, 2H), 5.05 (d, J = 5.3, 1H), 4.73-4.61 (m, 2H), 4.33-4.21 (m, 2H), 4.21-4.14 (m, 1H), 4.02-3.93 (m, 1H), 3.87 (t, J = 6.6, 1H), 2.85 (dd, J = 13.7, 5.4, 1H), 2.64-2.56 (m, 1H), 2.31-2.22 (m, 1H), 2.18-2.11 (m, 1H), 2.10-1.92 (m, 2H), 1.71-1.62 (m, 1H), 1.46-1.38 (m, 1H), 1.09-0.97 (m, 1H), 0.88-0.81 (m, 6H), 0.81-0.72 (m, 12H). |
| 8 | (S)-2-[(2S,3S)-2-((3S,4S)-3-Hydroxy-4-{(S)-3-methyl-2-[(S)-4-methyl-2-(3-methylbutyrylamino)-pentanoylamino]-butyrylamino}-5-phenylpentanoyl-amino)-3-methylpentanoylamino]-3-methylbutyric acid | 1H NMR (500 MHz, DMSO) ppm = 12.51 (s, 1H), 8.01-7.92 (m, 2H), 7.73 (d, J = 8.8, 1H), 7.69-7.61 (m, 2H), 7.28-7.11 (m, 5H), 5.08 (d, J = 5.1, 1H), 4.36-4.25 (m, 2H), 4.11-4.02 (m, 2H), 3.99-3.88 (m, 1H), 3.88-3.81 (m, 1H), 2.90-2.83 (m, 1H), 2.60 (dd, J = 13.8, 8.8, 1H), 2.28-2.19 (m, 1H), 2.16-2.09 (m, 1H), 2.09-1.81 (m, 5H), 1.75-1.63 (m, 1H), 1.63-1.50 (m, 1H), 1.50-1.34 (m, 3H), 1.12-0.96 (m, 1H), 0.90-0.70 (m, 30H). |
| 15 | (S)-2-[(2S,3S)-2-((3S,4S)-3-Hydroxy-4-{(S)-2-[2-(4-methoxyphenyl)-acetylamino]-3-methylbutyrylamino}-5-phenylpentanoyl-amino)-3-methylpentanoylamino]-3-methylbutyric acid | 1H NMR (500 MHz, DMSO) ppm = 12.51 (s, 1H), 7.97-7.89 (m, 2H), 7.78-7.69 (m, 2H), 7.24-7.10 (m, 7H), 6.86-6.79 (m, 2H), 5.08 (d, J = 5.6, 1H), 4.33-4.24 (m, 1H), 4.15-4.04 (m, 2H), 3.98-3.82 (m, 2H), 3.71 (s, 3H), 3.49-3.41 (m, 1H), 3.35 (s, 1H), 2.91-2.81 (m, 1H), 2.62-2.52 (m, 1H), 2.29-2.18 (m, 1H), 2.13 (dd, J = 14.3, 3.4, 1H), 2.08-1.96 (m, 1H), 1.95-1.83 (m, 1H), 1.75-1.64 (m, 1H), 1.50-1.38 (m, 1H), 1.12-0.99 (m, 1H), 0.90-0.72 (m, 18H). |
| 16 | Benzly (S)-2-((2S,3S)-2-{(3S,4S)-3-hydroxy-4-[(S)-3-methyl-2-(2-naphthalen-2-ylacetylamino)butyryl-amino]-5-phenyl-pentanoylamino}-3-methylpentanoyl-amino)-3-methyl-butyrate | 1H NMR (500 MHz, DMSO) ppm = 8.19 (d, J = 7.7, 1H), 8.09 (d, J = 9.0, 1H), 7.90-7.79 (m, 3H), 7.77-7.71 (m, 3H), 7.52-7.40 (m, 3H), 7.40-7.27 (m, 5H), 7.23-7.01 (m, 5H), 5.10 (s, 3H), 4.33-4.25 (m, 2H), 4.20-4.08 (m, 2H), 3.99-3.81 (m, 2H), 3.75-3.68 (m, 1H), 3.64-3.57 (m, 1H), 2.89-2.79 (m, 1H), 2.63-2.52 (m, 1H), 2.31-2.17 (m, 1H), 2.17-1.98 (m, 2H), 1.97-1.86 (m, 1H), 1.73-1.60 (m, 1H), 1.47-1.34 (m, 1H), 1.09-0.95 (m, 1H), 0.88-0.70 (m, 18H). |
| 17 | (S)-2-[(2S,3S)-2-((3S,4S)-4-{(S)-2-[2-(3-Ethoxyphenyl)-acetylamino]-3-methylbutyrylamino}-3-hydroxy-5-phenyl-pentanoylamino)-3-methylpentanoyl-amino]-3-methyl-butyric acid | 1H NMR (500 MHz, DMSO) ppm = 12.54 (s, 1H), 8.03 (d, J = 8.8, 1H), 7.84 (s, 2H), 7.75 (d, J = 8.5, 1H), 7.24-7.10 (m, 6H), 6.86-6.70 (m, 3H), 5.16 (s, 1H), 4.28-4.21 (m, 1H), 4.15-4.08 (m, 1H), 4.03 (s, 2H), 3.99-3.92 (m, 2H), 3.92-3.83 (m, 2H), 3.54-3.46 (m, 1H), 3.42-3.35 (m, 1H), 2.91-2.81 (m, 1H), 2.63-2.54 (m, 1H), 2.29-2.19 (m, 1H), 2.13 (d, J = 13.9, 1H), 2.09-1.96 (m, 1H), 1.96-1.84 (m, 1H), 1.76-1.64 (m, 1H), 1.47-1.37 (m, 1H), 1.34-1.22 (m, 3H), 1.12-0.99 (m, 1H), 0.90-0.74 (m, 18H). |
| 19 | Benzly (S)-2-[(2S,3S)-2-((3S,4S)-3-hydroxy-4-{(S)-3-methyl-2-[2-(3-phenoxyphenyl)-acetylamino]-butyrylamino}-5-phenylpentanoyl-amino)-3-methylpentanoylamino]-3-methylbutyrate | 1H NMR (500 MHz, DMSO) ppm = 8.19 (d, J = 7.7, 1H), 8.01 (d, J = 8.9, 1H), 7.77-7.71 (m, 2H), 7.41-7.22 (m, 8H), 7.22-7.08 (m, 6H), 7.06-7.00 (m, 1H), 7.00-6.91 (m, 3H), 6.89-6.79 (m, 1H), 5.10 (s, 2H), 5.06 (d, J = 5.4, 1H), 4.33-4.25 (m, 1H), 4.21-4.07 (m, 2H), 3.97-3.81 (m, 2H), 3.54 (d, J = 13.8, 1H), 3.39 (d, J = 13.7, 1H), 2.91-2.79 (m, 1H), 2.61-2.53 (m, 1H), 2.31-2.16 (m, 1H), 2.15-1.98 (m, 2H), 1.95-1.82 (m, 1H), 1.72-1.60 (m, 1H), 1.48-1.30 (m, 1H), 1.10-0.95 (m, 1H), 0.90-0.80 (m, 6H), 0.80-0.70 (m, 12H). |

TABLE 3-continued

| No. | Compound | NMR data |
|---|---|---|
| 20 | (S)-2-[(2S,3S)-2-((3S,4S)-3-Hydroxy-4-{(S)-2-[2-(3-methoxyphenyl)-acetylamino]-3-methylbutyrylamino}-5-phenylpentanoyl-amino)-3-methyl-pentanoylamino]-3-methylbutyric acid | 1H NMR (500 MHz, DMSO) ppm = 12.50 (s, 1H), 8.02-7.93 (m, 2H), 7.76-7.70 (m, 2H), 7.25-7.09 (m, 6H), 6.87-6.72 (m, 3H), 5.06 (d, J = 5.4, 1H), 4.33-4.25 (m, 1H), 4.17-4.05 (m, 2H), 3.98-3.82 (m, 2H), 3.70 (s, 3H), 3.54-3.47 (m, 1H), 3.39 (d, J = 13.7, 1H), 2.91-2.80 (m, 1H), 2.64-2.52 (m, 1H), 2.30-2.21 (m, 1H), 2.16-2.09 (m, 1H), 2.09-1.96 (m, 1H), 1.96-1.84 (m, 1H), 1.75-1.64 (m, 1H), 1.50-1.38 (m, 1H), 1.12-0.99 (m, 1H), 0.90-0.73 (m, 18H). |
| 22 | Benzly (S)-2-[(2S,3S)-2-((3S,4S)-3-hydroxy-4-{(S)-2-[2-(2-methoxyphenyl)-acetylamino]-3-methylbutyrylamino}-5-phenylpentanoyl-amino)-3-methyl-pentanoylamino]-3-methylbutyrate | 1H NMR (500 MHz, DMSO) ppm = 8.19 (d, J = 7.7, 1H), 7.78-7.67 (m, 2H), 7.62 (d, J = 8.9, 1H), 7.40-7.28 (m, 5H), 7.27-7.10 (m, 7H), 6.96-6.91 (m, 1H), 6.89-6.82 (m, 1H), 5.12-5.04 (m, 3H), 4.32-4.25 (m, 1H), 4.20-4.08 (m, 2H), 3.99-3.82 (m, 2H), 3.71 (s, 3H), 3.53-3.46 (m, 1H), 3.42-3.34 (m, 1H), 2.89-2.80 (m, 1H), 2.63-2.55 (m, 1H), 2.29-2.20 (m, 1H), 2.15-1.98 (m, 2H), 1.97-1.84 (m, 1H), 1.72-1.60 (m, 1H), 1.47-1.32 (m, 1H), 1.09-0.96 (m, 1H), 0.88-0.81 (m, 6H), 0.81-0.72 (m, 12H). |
| 24 | (S)-2-[(2S,3S)-2-((3S,4S)-3-Hydroxy-4-{(S)-2-[2-(2-methoxy-5-trifluoro-methoxyphenyl)-acetylamino]-3-methylbutyrylamino}-5-phenylpentanoyl-amino)-3-methyl-pentanoylamino]-3-methylbutyric acid | 1H NMR (500 MHz, DMSO) ppm = 13.09-12.05 (m, 1H), 7.94-7.85 (m, 2H), 7.82-7.72 (m, 2H), 7.27-7.10 (m, 7H), 7.01 (d, J = 8.6, 1H), 5.12 (s, 1H), 4.29-4.22 (m, 1H), 4.19-4.10 (m, 1H), 4.09-4.03 (m, 1H), 3.96-3.90 (m, 1H), 3.90-3.82 (m, 1H), 3.73 (s, 3H), 3.57-3.50 (m, 1H), 3.48-3.39 (m, 1H), 2.92-2.82 (m, 1H), 2.64-2.56 (m, 1H), 2.29-2.21 (m, 1H), 2.17-2.09 (m, 1H), 2.08-1.97 (m, 1H), 1.97-1.85 (m, 1H), 1.75-1.63 (m, 1H), 1.48-1.37 (m, 1H), 1.11-0.97 (m, 1H), 0.89-0.75 (m, 18H). |
| 25 | (S)-2-((2S,3S)-2-{(3S,4S)-3-Hydroxy-4-[(S)-3-methyl-2-(2-naphthalen-2-ylacetylamino)butyryl-amino]-5-phenyl-pentanoylamino}-3-methylpentanoyl-amino)-3-methyl-butyric acid | 1H NMR (500 MHz, DMSO) ppm = 12.51 (s, 1H), 8.10 (d, J = 8.9, 1H), 7.94 (d, J = 8.1, 1H), 7.90-7.71 (m, 6H), 7.52-7.40 (m, 3H), 7.24-7.01 (m, 5H), 5.09 (d, J = 5.5, 1H), 4.32-4.24 (m, 1H), 4.18-4.04 (m, 2H), 3.99-3.83 (m, 2H), 3.75-3.68 (m, 1H), 3.64-3.55 (m, 1H), 2.91-2.82 (m, 1H), 2.63-2.54 (m, 1H), 2.30-2.21 (m, 1H), 2.18-2.10 (m, 1H), 2.09-1.85 (m, 2H), 1.75-1.63 (m, 1H), 1.49-1.37 (m, 1H), 1.11-0.97 (m, 1H), 0.90-0.74 (m, 18H). |
| 26 | (S)-2-((2S,3S)-2-{(3S,4S)-4-[(S)-2-(3-tert-Butoxy-benzoylamino)-3-methylbutyrylamino]-3-hydroxy-5-phenyl-pentanoylamino}-3-methylpentanoyl-amino)-3-methyl-butyric acid | 1H NMR (500 MHz, DMSO) ppm = 12.48 (s, 1H), 8.24 (d, J = 8.7, 1H), 7.95 (d, J = 8.0, 1H), 7.76-7.65 (m, 2H), 7.60-7.55 (m, 1H), 7.44-7.34 (m, 2H), 7.23-7.18 (m, 2H), 7.17-7.10 (m, 3H), 7.10-7.03 (m, 1H), 5.11 (d, J = 5.8, 1H), 4.30-4.24 (m, 1H), 4.18 (t, J = 8.6, 1H), 4.08 (dd, J = 8.2, 5.9, 1H), 4.00-3.92 (m, 1H), 3.91-3.85 (m, 1H), 2.88-2.81 (m, 1H), 2.65-2.59 (m, 1H), 2.29-2.21 (m, 1H), 2.19-2.12 (m, 1H), 2.08-1.99 (m, 2H), 1.75-1.66 (m, 1H), 1.48-1.40 (m, 1H), 1.32 (s, 9H), 1.11-1.03 (m, 1H), 0.90-0.75 (m, 18H). |
| 27 | (S)-2-[(2S,3S)-2-((3S,4S)-3-Hydroxy-4-{(S)-3-methyl-2-[2-(3-phenoxyphenyl)-acetylamino]-butyrylamino}-5-phenylpentanoyl-amino)-3-methyl-pentanoylamino]-3-methylbutyric acid | 1H NMR (500 MHz, DMSO) ppm = 12.46 (s, 1H), 7.98 (d, J = 8.9, 1H), 7.89 (d, J = 8.3, 1H), 7.71 (d, J = 8.7, 2H), 7.41-7.32 (m, 2H), 7.32-7.24 (m, 2H), 7.23-7.08 (m, 6H), 7.03 (d, J = 7.6, 1H), 7.00-6.92 (m, 3H), 6.88-6.80 (m, 1H), 5.06 (s, 1H), 4.31-4.24 (m, 1H), 4.15-4.04 (m, 2H), 3.97-3.89 (m, 1H), 3.89-3.81 (m, 1H), 3.54 (d, J = 13.8, 1H), 3.44-3.35 (m, 1H), 2.91-2.80 (m, 1H), 2.63-2.54 (m, 1H), 2.29-2.18 (m, 1H), 2.18-2.07 (m, 1H), 2.07-1.96 (m, 1H), 1.96-1.82 (m, 1H), 1.76-1.64 (m, 1H), 1.50-1.38 (m, 1H), 1.12-0.99 (m, 1H), 0.91-0.68 (m, 18H). |

TABLE 3-continued

| No. | Compound | NMR data |
|---|---|---|
| 28 | (S)-2-[(2S,3S)-2-((3S,4S)-3-Hydroxy-4-{(S)-2-[2-(2-methoxyphenyl)-acetylamino]-3-methylbutyrylamino}-5-phenylpentanoyl-amino)-3-methyl-pentanoylamino]-3-methylbutyric acid | 1H NMR (500 MHz, DMSO) ppm = 12.22 (m, 1H), 12.70-7.88 (d, J = 8.2, 1H), 7.77-7.66 (m, 2H), 7.59 (d, J = 8.8, 1H), 7.26-7.11 (m, 7H), 6.96-6.91 (m, 1H), 6.89-6.82 (m, 1H), 5.10 (s, 1H), 4.31-4.22 (m, 1H), 4.18-4.10 (m, 1H), 4.10-4.03 (m, 1H), 3.99-3.90 (m, 1H), 3.89-3.82 (m, 1H), 3.71 (s, 3H), 3.53-3.46 (m, 1H), 3.43-3.36 (m, 1H), 2.91-2.83 (m, 1H), 2.65-2.57 (m, 1H), 2.29-2.20 (m, 1H), 2.17-2.09 (m, 1H), 2.08-1.98 (m, 1H), 1.91 (h, J = 6.8, 1H), 1.75-1.65 (m, 1H), 1.48-1.38 (m, 1H), 1.10-0.99 (m, 1H), 0.90-0.71 (m, 18H). |
| 29 | (S)-2-[(2S,3S)-2-((3S,4S)-4-{(S)-2-[2-(3,4-Dimethyl-phenoxy)acetyl-amino]-3-methyl-butyrylamino}-3-hydroxy-5-phenyl-pentanoylamino)-3-methylpentanoyl-amino]-3-methyl-butyric acid | 1H NMR (500 MHz, DMSO) ppm = 12.47 (s, 1H), 7.94-7.81 (m, 2H), 7.72 (d, J = 8.8, 1H), 7.65 (d, J = 9.0, 1H), 7.21 (d, J = 4.4, 4H), 7.16-7.10 (m, 1H), 7.01 (d, J = 8.3, 1H), 6.74 (d, J = 2.7, 1H), 6.64 (dd, J = 8.2, 2.7, 1H), 5.07 (s, 1H), 4.52-4.40 (m, 2H), 4.31-4.18 (m, 2H), 4.11-4.05 (m, 1H), 4.01-3.92 (m, 1H), 3.90-3.83 (m, 1H), 2.91-2.81 (m, 1H), 2.65-2.57 (m, 1H), 2.29-2.21 (m, 1H), 2.14 (d, J = 19.8, 6H), 2.06-1.90 (m, 2H), 1.76-1.66 (m, 1H), 1.49-1.39 (m, 1H), 1.31-1.20 (m, 1H), 1.11-1.01 (m, 1H), 0.90-0.70 (m, 18H). |
| 30 | (S)-2-((2S,3S)-2-{(3S,4S)-3-Hydroxy-4-[(S)-3-methyl-2-(2-naphthalen-1-ylacetylamino)butyryl-amino]-5-phenyl-pentanoylamino}-3-methylpentanoyl-amino)-3-methyl-butyric acid | 1H NMR (500 MHz, DMSO) ppm = 12.47 (s, 1H), 8.14-8.04 (m, 2H), 7.94-7.84 (m, 2H), 7.82-7.77 (m, 1H), 7.77-7.67 (m, 1H), 7.51-7.46 (m, 2H), 7.45-7.39 (m, 2H), 7.21 (d, J = 4.4, 4H), 7.18-7.12 (m, 1H), 5.08 (s, 1H), 4.32-4.24 (m, 1H), 4.17-4.12 (m, 1H), 4.11-4.01 (m, 2H), 3.99-3.83 (m, 3H), 2.90-2.83 (m, 1H), 2.63-2.56 (m, 1H), 2.28-2.20 (m, 1H), 2.17-2.08 (m, 1H), 2.07-1.89 (m, 2H), 1.74-1.65 (m, 1H), 1.47-1.37 (m, 1H), 1.09-0.98 (m, 1H), 0.89-0.73 (m, 18H). |
| 33 | (S)-2-{(2S,3S)-2-[(3S,4S)-4-((S)-2-Diphenylacetylamino-3-methylbutyryl-amino)-3-hydroxy-5-phenylpentanoyl-amino]-3-methylpentanoylamino}-3-methylbutyric acid | 1H NMR (500 MHz, DMSO) ppm = 12.45 (s, 1H), 8.20 (d, J = 8.9, 1H), 7.91-7.77 (m, 2H), 7.72 (d, J = 8.9, 1H), 7.31-7.07 (m, 15H), 5.17 (s, 1H), 5.11 (s, 1H), 4.30-4.23 (m, 1H), 4.21-4.14 (m, 1H), 4.10-4.03 (m, 1H), 3.94-3.82 (m, 2H), 2.89-2.82 (m, 1H), 2.61-2.54 (m, 1H), 2.28-2.10 (m, 2H), 2.07-1.98 (m, 1H), 1.95-1.85 (m, 1H), 1.75-1.66 (m, 1H), 1.48-1.38 (m, 1H), 1.10-1.00 (m, 1H), 0.89-0.70 (m, 18H). |
| 35 | Benzly (S)-2-((2S,3S)-2-{(3S,4S)-3-hydroxy-4-[(S)-2-((S)-2-hydroxy-2-phenylacetylamino)-3-methylbutyryl-amino]-5-phenyl-pentanoylamino}-3-methylpentanoyl-amino)-3-methyl-butyrate | 1H NMR (500 MHz, DMSO) ppm = 8.16 (d, J = 7.8, 1H), 7.91 (d, J = 8.7, 1H), 7.75 (d, J = 8.8, 1H), 7.67 (d, J = 9.2, 1H), 7.41-7.29 (m, 9H), 7.28-7.12 (m, 6H), 6.36 (d, J = 4.7, 1H), 5.11 (s, 2H), 5.07 (d, J = 5.1, 1H), 4.90 (d, J = 4.7, 1H), 4.33-4.26 (m, 1H), 4.23-4.14 (m, 2H), 4.02-3.92 (m, 1H), 3.92-3.84 (m, 1H), 2.91-2.83 (m, 1H), 2.63-2.56 (m, 1H), 2.30-2.22 (m, 1H), 2.19-2.11 (m, 1H), 2.09-2.00 (m, 1H), 1.99-1.88 (m, 1H), 1.72-1.61 (m, 1H), 1.47-1.37 (m, 1H), 1.09-0.99 (m, 1H), 0.90-0.82 (m, 6H), 0.82-0.74 (m, 6H), 0.69 (dd, J = 11.0, 6.7, 6H). |
| 36 | (S)-2-[(2S,3S)-2-((3S,4S)-3-Hydroxy-4-{(S)-methyl-1-(S)-2-[2-(3-ethoxyphenyl)-acetylamino]-3-oxopentylamino}-5-phenylpentanoyl-amino)-3-methyl-pentanoylamino]-3-methylbutyric acid | 1H NMR (500 MHz, DMSO) ppm = 12.49 (s, 1H), 7.99 (d, J = 8.9, 1H), 7.88 (d, J = 8.2, 1H), 7.76-7.64 (m, 2H), 7.23-7.10 (m, 6H), 6.85-6.81 (m, 1H), 6.79 (d, J = 7.5, 1H), 6.77-6.71 (m, 1H), 5.08 (s, 1H), 4.33-4.23 (m, 1H), 4.17-4.10 (m, 1H), 4.10-4.03 (m, 1H), 4.01-3.88 (m, 3H), 3.88-3.81 (m, 1H), 3.50-3.36 (m, 2H), 2.91-2.80 (m, 1H), 2.65-2.55 (m, 1H), 2.30-2.18 (m, 1H), 2.18-2.10 (m, 1H), 2.10-1.96 (m, 1H), 1.77-1.62 (m, 2H), 1.50-1.39 (m, 1H), 1.39-1.24 (m, 4H), 1.14-0.94 (m, 2H), 0.92-0.66 (m, 18H). |

TABLE 3-continued

| No. | Compound | NMR data |
|-----|----------|----------|
| 37 | (S)-2-((2S,3S)-2-{(3S,4S)-3-Hydroxy-4-[(S)-2-((S)-2-hydroxy-2-phenylacetylamino)-3-methylbutyryl-amino]-5-phenyl-pentanoylamino}-3-methylpentanoyl-amino)-3-methyl-butyric acid | 1H NMR (500 MHz, DMSO) ppm = 12.48 (s, 1H), 7.92 (d, J = 8.4, 2H), 7.80-7.63 (m, 2H), 7.39 (d, J = 7.5, 2H), 7.36-7.10 (m, 8H), 6.37 (s, 1H), 5.08 (d, J = 5.3, 1H), 4.91 (s, 1H), 4.34-4.25 (m, 1H), 4.24-4.16 (m, 1H), 4.15-4.05 (m, 1H), 4.02-3.93 (m, 1H), 3.93-3.83 (m, 1H), 2.92-2.83 (m, 1H), 2.64-2.56 (m, 1H), 2.31-2.21 (m, 1H), 2.21-2.10 (m, 1H), 2.10-1.88 (m, 2H), 1.78-1.63 (m, 1H), 1.52-1.38 (m, 1H), 1.13-0.99 (m, 1H), 0.92-0.77 (m, 12H), 0.73-0.64 (m, 6H). |
| 38 | (S)-2-((2S,3S)-2-{(3S,4S)-4-[(S)-2-(2,2-Diethyl-butyrylamino)-3-methylbutyrylamino]-3-hydroxy-5-phenyl-pentanoylamino}-3-methylpentanoyl-amino)-3-methyl-butyric acid | 1H NMR (500 MHz, DMSO) ppm = 12.45 (s, 1H), 7.86 (s, 1H), 7.73 (d, J = 8.8, 2H), 7.21 (d, J = 4.4, 4H), 7.17-7.08 (m, 1H), 7.03 (s, 1H), 5.14 (s, 1H), 4.31-4.19 (m, 1H), 4.07 (t, J = 8.1, 2H), 3.98-3.88 (m, 1H), 3.86-3.80 (m, 1H), 2.94-2.82 (m, 1H), 2.67-2.59 (m, 1H), 2.28-2.18 (m, 1H), 2.18-2.10 (m, 1H), 2.08-1.98 (m, 1H), 1.98-1.88 (m, 1H), 1.77-1.66 (m, 1H), 1.52-1.39 (m, 7H), 1.13-1.00 (m, 1H), 0.92-0.70 (m, 18H), 0.70-0.59 (m, 9H). |
| 39 | (S)-2-{(2S,3S)-2-[(3S,4S)-4-((S)-2-{2-[3-(2-tert-Butoxy-carbonylamino-ethoxy)phenyl]acetyl-amino}-3-methyl-1-(S)-oxopentylamino)-3-hydroxy-5-phenyl-pentanoylamino]-3-methylpentanoyl-amino}-3-methyl-butyric acid | 1H NMR (500 MHz, DMSO) ppm = 12.51 (s, 1H), 7.98 (d, J = 9.0, 1H), 7.90 (d, J = 8.3, 1H), 7.76-7.64 (m, 2H), 7.27-7.09 (m, 6H), 7.00-6.90 (m, 1H), 6.86-6.70 (m, 3H), 5.08 (s, 1H), 4.28 (t, J = 8.0, 1H), 4.17-4.03 (m, 2H), 3.98-3.79 (m, 4H), 3.55-3.43 (m, 2H), 3.20-3.13 (m, 2H), 2.90-2.82 (m, 1H), 2.63-2.55 (m, 1H), 2.30-2.20 (m, 1H), 2.20-2.11 (m, 1H), 2.08-1.98 (m, 1H), 1.76-1.58 (m, 2H), 1.47-1.41 (m, 1H), 1.38 (s, 9H), 1.33-1.25 (m, 1H), 1.11-0.95 (m, 2H), 0.90-0.67 (m, 18H). |
| 40 | (S)-2-[(2S,3S)-2-((3S,4S)-3-Hydroxy-4-{(2S,3S)-3-methyl-2-[2-(3-propoxy-phenyl)acetylamino]-pentanoylamino}-5-phenylpentanoyl-amino)-3-methyl-pentanoylamino]-3-methylbutyric acid | 1H NMR (500 MHz, DMSO) ppm = 12.47 (s, 1H), 8.03-7.86 (m, 2H), 7.68 (d, J = 8.8, 2H), 7.23-7.09 (m, 6H), 6.86-6.72 (m, 3H), 5.04 (d, J = 5.5, 1H), 3.41-3.34 (m, 1H), 4.32-4.25 (m, 1H), 4.17-4.06 (m, 2H), 3.98-3.90 (m, 1H), 3.90-3.81 (m, 3H), 3.52-3.44 (m, 1H), 2.91-2.79 (m, 1H), 2.63-2.55 (m, 1H), 2.29-2.20 (m, 1H), 2.19-2.10 (m, 1H), 2.08-1.97 (m, 1H), 1.76-1.62 (m, 4H), 1.49-1.39 (m, 1H), 1.38-1.28 (m, 1H), 1.11-0.98 (m, 2H), 0.98-0.92 (m, 3H), 0.90-0.71 (m, 18H). |
| 41 | (S)-2-{(2S,3S)-2-[(3S,4S)-4-((S)-2-{2-[3-(2-Aminoethoxy)-phenyl]acetylamino}-3-methyl-1-(S)-oxopentylamino)-3-hydroxy-5-phenyl-pentanoylamino]-3-methylpentanoyl-amino}-3-methyl-butyric acid | 1H NMR (500 MHz, DMSO) ppm = 12.48 (s, 1H), 8.14-8.00 (m, 4H), 7.93 (d, J = 8.2, 1H), 7.78-7.66 (m, 2H), 7.27-7.18 (m, 4H), 7.18-7.09 (m, 1H), 6.92-6.85 (m, 2H), 6.85-6.78 (m, 1H), 5.07 (s, 1H), 4.32-4.26 (m, 1H), 4.16-4.06 (m, 4H), 3.98-3.91 (m, 1H), 3.88-3.81 (m, 1H), 3.54-3.48 (m, 1H), 3.43-3.38 (m, 1H), 3.23-3.15 (m, 2H), 2.90-2.82 (m, 1H), 2.65-2.56 (m, 1H), 2.30-2.21 (m, 1H), 2.19-2.11 (m, 1H), 2.08-1.98 (m, 1H), 1.76-1.62 (m, 2H), 1.49-1.39 (m, 1H), 1.35-1.28 (m, 1H), 1.10-0.95 (m, 2H), 0.91-0.66 (m, 18H). |
| 42 | N-[(1S,2S)-1-(1-Ethyl-propylcarbamoyl)-2-methylbutyl]-(2S,5S)-3-hydroxy-4-{(S)-3-methyl-2-[(S)-4-methyl-2-(3-methyl-butyrylamino)-pentanoylamino]-butyrylamino}-5-phenylpentanamide | 1H NMR (500 MHz, DMSO) ppm = 8.70-8.68 (m, 1H), 7.97 (d, J = 8.2, 1H), 7.66-7.55 (m, 3H), 7.27-7.09 (m, 5H), 4.37-4.28 (m, 1H), 4.16-4.09 (m, 1H), 4.09-4.01 (m, 1H), 3.98-3.89 (m, 1H), 3.89-3.82 (m, 1H), 3.56-3.46 (m, 1H), 2.91-2.82 (m, 1H), 2.66-2.58 (m, 1H), 2.29-2.19 (m, 1H), 2.18-2.10 (m, 1H), 2.03-1.84 (m, 4H), 1.74-1.64 (m, 1H), 1.64-1.52 (m, 1H), 1.49-1.36 (m, 5H), 1.36-1.23 (m, 2H), 1.13-1.00 (m, 1H), 0.94-0.65 (m, 30H). |

TABLE 3-continued

| No. | Compound | NMR data |
|---|---|---|
| 43 | N-[(1S,2S)-1-(1-Ethylpropyl-carbamoyl)-2-methyl-butyl]-(2S,5S)-3-hydroxy-4-[(S)-3-methyl-2-((S)-4-methyl-2-phenyl-acetylamino-pentanoylamino)-1-oxobutylamino]-5-phenylpentanamide | 1H NMR (500 MHz, DMSO) ppm = 8.26 (d, J = 8.2, 1H), 7.73 (d, J = 8.8, 1H), 7.67-7.54 (m, 3H), 7.29-7.09 (m, 10H), 5.30-4.83 (m, 1H), 4.37-4.29 (m, 1H), 4.18-4.09 (m, 1H), 4.08-4.01 (m, 1H), 4.01-3.90 (m, 1H), 3.90-3.82 (m, 1H), 3.57-3.36 (m, 3H), 2.90-2.82 (m, 1H), 2.66-2.57 (m, 1H), 2.31-2.19 (m, 1H), 2.18-2.11 (m, 1H), 1.94-1.80 (m, J = 6.8, 1H), 1.75-1.63 (m, 1H), 1.62-1.49 (m, 1H), 1.49-1.23 (m, 7H), 1.13-1.00 (m, 1H), 0.88-0.65 (m, 24H). |
| 44 | Benzyl (S)-2-((2S,3S)-2-{(3S,4S)-3-hydroxy-4-[(S)-3-methyl-2-((S)-4-methyl-2-phenylacetylamino-pentanoylamino)-butyrylamino]-5-phenylpentanoyl-amino}-3-methyl-pentanoylamino)-3-methylbutyrate | 1H NMR (500 MHz, DMSO) ppm = 8.24 (d, J = 8.2, 1H), 8.15 (d, J = 7.7, 1H), 7.74-7.68 (m, 2H), 7.59 (d, J = 8.8, 1H), 7.40-7.09 (m, 15H), 5.10 (s, 3H), 4.37-4.26 (m, 2H), 4.20-4.14 (m, 1H), 4.11-4.02 (m, 1H), 4.00-3.91 (m, 1H), 3.88-3.81 (m, 1H), 3.51-3.39 (m, 2H), 2.89-2.81 (m, 1H), 2.60 (dd, J = 13.8, 8.8, 1H), 2.28-2.19 (m, 1H), 2.16-1.98 (m, 2H), 1.86 (h, J = 6.8, 1H), 1.73-1.61 (m, 1H), 1.61-1.48 (m, 1H), 1.48-1.36 (m, 3H), 1.10-0.94 (m, 1H), 0.91-0.67 (m, 24H). |
| 45 | (S)-2-((2S,3S)-2-{(3S,4S)-3-Hydroxy-4-[(S)-3-methyl-2-((S)-4-methyl-2-phenylacetylamino-pentanoylamino)-butyrylamino]-5-phenylpentanoyl-amino}-3-methyl-pentanoylamino)-3-methylbutyric acid | 1H NMR (500 MHz, DMSO) ppm = 12.49 (s, 1H), 8.42 (s, 1H), 7.78-7.74 (m, 4H), 7.29-7.09 (m, 10H), 5.19 (s, 1H), 4.34-4.19 (m, 2H), 4.12-4.00 (m, 2H), 3.93-3.82 (m, 2H), 3.51-3.36 (m, 2H), 2.95-2.87 (m, 1H), 2.66-2.58 (m, 1H), 2.30-2.21 (m, 1H), 2.21-2.13 (m, 1H), 2.09-1.98 (m, 1H), 1.94-1.83 (m, 1H), 1.77-1.67 (m, 1H), 1.62-1.49 (m, 1H), 1.49-1.39 (m, 3H), 1.10-1.03 (m, 1H), 0.91-0.75 (m, 18H), 0.73 (d, J = 6.8, 6H). |
| 46 | N-((1S,2S)-1-Cyclo-pentylcarbamoyl-2-methylbutyl)-(2S,5S)-3-hydroxy-4-{(S)-3-methyl-2-[(S)-4-methyl-2-(3-methyl-butyrylamino)-pentanoylamino]-butyrylamino}-5-phenylpentanamide | 1H NMR (500 MHz, DMSO) ppm = 7.96 (d, J = 8.2, 1H), 7.85 (d, J = 7.3, 1H), 7.68-7.55 (m, 3H), 7.28-7.11 (m, 5H), 5.20-4.90 (m, 1H), 4.37-4.29 (m, 1H), 4.13-4.02 (m, 2H), 4.01-3.90 (m, 2H), 3.88-3.81 (m, 1H), 2.91-2.82 (m, 1H), 2.66-2.58 (m, 1H), 2.28-2.19 (m, 1H), 2.17-2.09 (m, 1H), 2.05-1.84 (m, 4H), 1.80-1.53 (m, 6H), 1.53-1.28 (m, 7H), 1.11-0.95 (m, 1H), 0.92-0.65 (m, 24H). |
| 47 | N-[(S)-1-(1-Ethylpropyl-carbamoyl)-2-methyl-propyl]-(3S,4S)-3-hydroxy-4-{(S)-3-methyl-2-[(S)-4-methyl-2-(3-methyl-butyrylamino)-pentanoylamino]-butyrylamino}-5-phenylpentanamide | 1H NMR (500 MHz, DMSO) ppm = 7.96 (d, J = 8.1, 1H), 7.65 (d, J = 8.7, 1H), 7.62-7.53 (m, 3H), 7.28-7.09 (m, 5H), 5.05 (d, J = 4.6, 1H), 4.38-4.29 (m, 1H), 4.13-4.01 (m, 2H), 4.01-3.83 (m, 2H), 3.58-3.46 (m, 1H), 2.91-2.82 (m, 1H), 2.62 (dd, J = 13.9, 8.8, 1H), 2.33-2.20 (m, 1H), 2.19-2.10 (m, 1H), 2.05-1.83 (m, 5H), 1.64-1.50 (m, 1H), 1.50-1.23 (m, 6H), 0.95-0.63 (m, 30H). |
| 48 | N-[(S)-1-(1-Ethylpropyl-carbamoyl)butyl]-(3S,4S)-3-hydroxy-4-{(S)-3-methyl-2-[(S)-4-methyl-2-(3-methyl-butyrylamino)-pentanoylamino]-butyrylamino}-5-phenylpentanamide | 1H NMR (500 MHz, DMSO) ppm = 7.97 (d, J = 8.2, 1H), 7.74-7.63 (m, 2H), 7.56-7.48 (m, 2H), 7.28-7.11 (m, 5H), 5.25-4.84 (m, 1H), 4.38-4.30 (m, 1H), 4.23-4.14 (m, 1H), 4.09-4.02 (m, 1H), 3.99-3.84 (m, 2H), 3.56-3.45 (m, 1H), 2.89-2.81 (m, 1H), 2.68-2.57 (m, 1H), 2.27-2.17 (m, 1H), 2.16-2.08 (m, 1H), 2.05-1.84 (m, 4H), 1.65-1.53 (m, 2H), 1.53-1.19 (m, 9H), 0.92-0.68 (m, 27H). |

TABLE 3-continued

| No. | Compound | NMR data |
|---|---|---|
| 49 | N-[(1S,2S)-1-(3-Hydroxy-1,1-dimethylpropyl-carbamoyl)-2-methyl-butyl]-(3S,4S)-3-hydroxy-4-{(S)-3-methyl-2-[(S)-4-methyl-2-(3-methyl-butyrylamino)-pentanoylamino]-butyrylamino}-5-phenylpentanamide | 1H NMR (500 MHz, DMSO) ppm = 7.95 (d, J = 8.2, 1H), 7.66-7.55 (m, 3H), 7.43 (s, 1H), 7.28-7.11 (m, 5H), 5.06 (d, J = 5.1, 1H), 4.37-4.27 (m, 2H), 4.14-4.01 (m, 2H), 3.98-3.88 (m, 1H), 3.88-3.81 (m, 1H), 3.47-3.40 (m, 2H), 2.91-2.81 (m, 1H), 2.65-2.57 (m, 1H), 2.28-2.19 (m, 1H), 2.16-2.09 (m, 1H), 2.03-1.70 (m, 6H), 1.70-1.51 (m, 2H), 1.50-1.36 (m, 3H), 1.22 (s, 6H), 1.10-0.95 (m, 1H), 0.91-0.71 (m, 24H). |

EXAMPLE 2: PREPARATION OF THE COMPOUNDS ACCORDING TO THE INVENTION

The compounds according to the invention can be prepared, for example, by methods known to the person skilled in the art by the following synthesis sequences. The examples indicated describe the synthesis, but do not restrict the latter to the examples.

Synthesis Sequence:

Starting from the protected hydroxystatin building block A, the novel peptide bond is built up with corresponding amines, amino acid derivatives, dipeptides, tripeptides or tetrapeptides (typically protected on the C terminal) with the aid of an amide coupling method known to the person skilled in the art, such as, for example, a DAPECl coupling.

In the second step, the BOC protecting group is cleaved off under suitable conditions (for example by HCl/dioxane or TFA/DCM), and the building block obtained is coupled to a corresponding acid, amino acid derivatives, dipeptides,

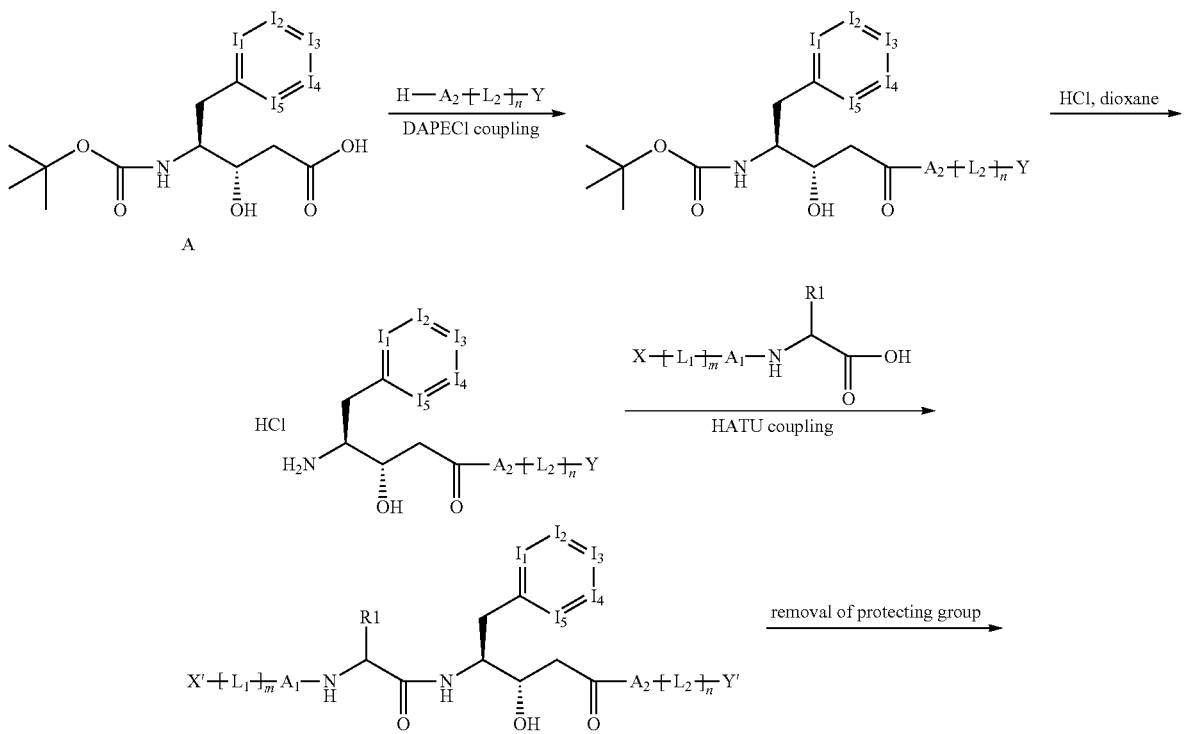

X' and Y' denote a group X or Y respectively which is protected by a protecting group

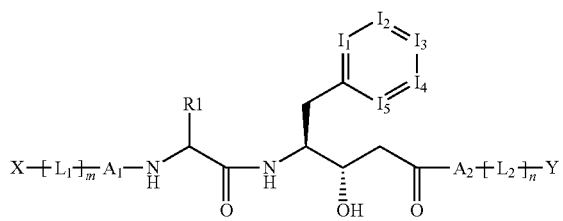

tripeptides or tetrapeptides (typically each protected on the N terminal). Particular preference is given in this step to coupling reagents which are suitable for suppressing racemisation, such as, for example, HATU or similar reagents. In further steps, further protecting groups can subsequently be removed, for example Z-protecting groups or benzyl esters can be hydrolysed to the free acid in the presence of Pd/C.

Analogously to the preparation process described above, the following compounds, for example, can be prepared without restricting the applicability to these building blocks.

EXAMPLE 3: PREPARATION OF (A8): (S)-2-[(2S,3S)-2-((3S,4S)-3-HYDROXY-4-{(S)-3-METHYL-2-[(S)-4-METHYL-2-(3-METHYLBUTYRYLAMINO)PENTANOYLAMINO]BUTYRYLAMINO}-5-PHENYLPENTANOYLAMINO)-3-METHYLPENTANOYLAMINO]-3-METHYLBUTYRIC ACID

Step 1:

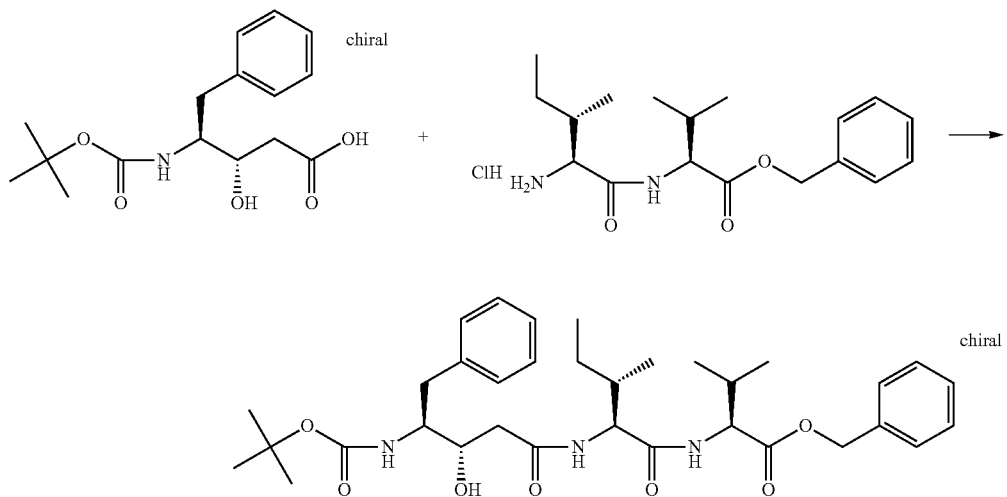 [SMILES: CC(C)(C)OC(=O)N[C@@H](Cc1ccccc1)[C@@H](O)CC(=O)O ; Cl ; CC[C@H](C)[C@H](N)C(=O)N[C@H](C(=O)OCc1ccccc1)C(C)C ; CC[C@H](C)[C@H](NC(=O)C[C@H](O)[C@H](Cc1ccccc1)NC(=O)OC(C)(C)C)C(=O)N[C@H](C(=O)OCc1ccccc1)C(C)C]

5.000 g of (3S,4S)-4-tert-butoxycarbonylamino-3-hydroxy-5-phenylpentanoic acid, 6.364 g of benzyl (S)-2-((2S,3S)-2-amino-3-methylpentanoylamino)-3-methylbutyrate (as hydrochloride), 1.092 g of 1-hydroxybenzotriazole hydrate, 3.664 ml of 4-methylmorpholine and 3.099 g of N-(3-dimethylaminopropyl)-N'-ethylcarbodiimide hydrochloride (DAPECl) were dissolved in about 50 ml of DMF in a flask with ice-cooling and stirred overnight. The reaction mixture was poured into saturated sodium hydrogencarbonate solution and stirred for 15 min. The precipitate formed was filtered off with suction, dissolved in DCM and washed repeatedly firstly with hydrogencarbonate solution, then with dilute formic acid solution and water. The solvent was removed, the residue was taken up in DMF, the solution was poured into a citric acid buffer, and the precipitate formed was filtered off with suction. Reprecipitation and drying twice gave 7.380 g of benzyl (S)-2-[(2S,3S)-2-((3S,4S)-4-tert-butoxycarbonylamino-3-hydroxy-5-phenylpentanoylamino)-3-methylpentanoylamino]-3-methylbutyrate as white solid. (Yield 74.6%, content >99%). MS-FAB (M+H$^+$—BOC)=512.7 R$_f$ (polar method): 2.66 min.

Step 2:

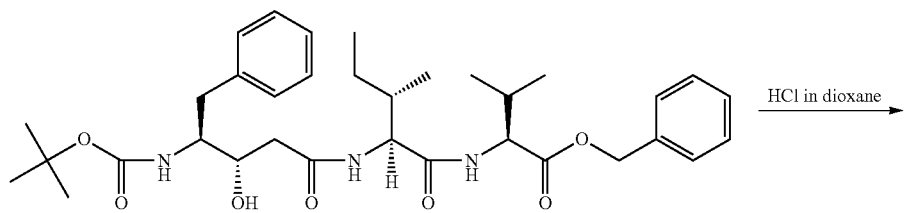

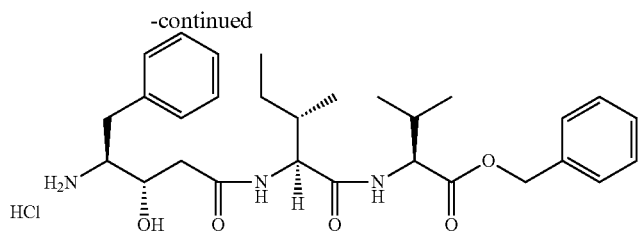

7.380 g of benzyl (S)-2-[(2S,3S)-2-((3S,4S)-4-tert-butoxycarbonylamino-3-hydroxy-5-phenylpentanoylamino)-3-methylpentanoylamino]-3-methylbutyrate were dissolved in 15 ml of HCl solution in dioxane (4 M) in a flask with ice-cooling and stirred at RT for 5 h. Excess HCl was removed in the house vacuum, the solvent was removed in vacuo, and the residue was lyophilised overnight.

In order to remove dioxane residues, the residue was repeatedly triturated with heptane, filtered off with suction and dried, giving 6.420 g of benzyl (S)-2-[(2S,3S)-2-((3S,4S)-4-amino-3-hydroxy-5-phenylpentanoylamino)-3-methylpentanoylamino]-3-methylbutyrate as white solid. (Yield 97%, content >99%). MS-FAB (M+H$^+$)=512.3 R$_f$ (polar method): 1.76 min.

Step 3:

flask with ice-cooling, 2.659 g of HATU (C10H15N6O*PF6) were added, and the mixture was stirred at RT overnight. The yellow reaction mixture was poured into saturated sodium hydrogencarbonate solution and stirred for 15 min. The precipitate formed was filtered off with suction, triturated with water and with dilute formic acid, filtered off with suction again, washed with water and dried. The residue was treated with methanol in an ultrasound bath and filtered off with suction. This operation was repeated a further twice, giving 3.400 g of benzyl (S)-2-[(2S,3S)-2-((3S,4S)-3-hydroxy-4-{(S)-3-methyl-2-[(S)-4-methyl-2-(3-methylbutyrylamino)-pentanoylamino]butyrylamino}-5-phenylpentanoylamino)-3-methylpentanoylamino]-3-methylbutyrate as white solid. (Yield 65%). MS-FAB (M+H$^+$)=809.0 R$_f$ (polar method): 2.71 min.

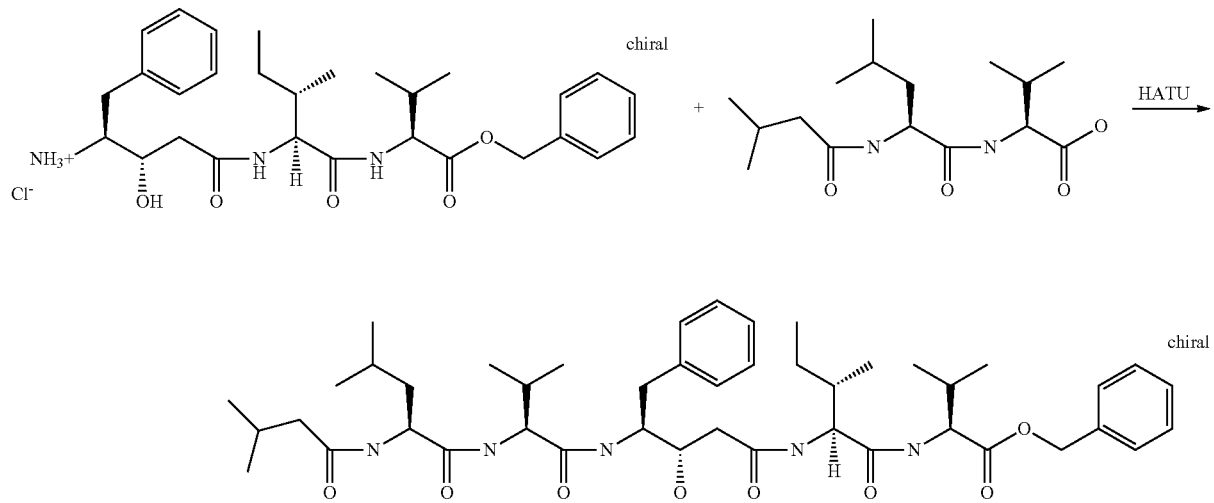

3.500 g of benzyl (S)-2-[(2S,3S)-2-((3S,4S)-4-amino-3-hydroxy-5-phenylpentanoylamino)-3-methylpentanoylamino]-3-methylbutyrate (as hydrochloride), 2.199 g of (S)-3-methyl-2-[(S)-4-methyl-2-(3-methylbutyrylamino)pentanoylamino]butyric acid and 2.162 ml of ethyl-diisopropylamine were dissolved in about 30 ml of DMF in a Compounds No. 1-3, 7, 10-13, 16, 18, 19, 21-23, 32, 34, 35 from Table 2, for example, can be prepared analogously to this step (without restricting the method to these compounds).

Step 4:

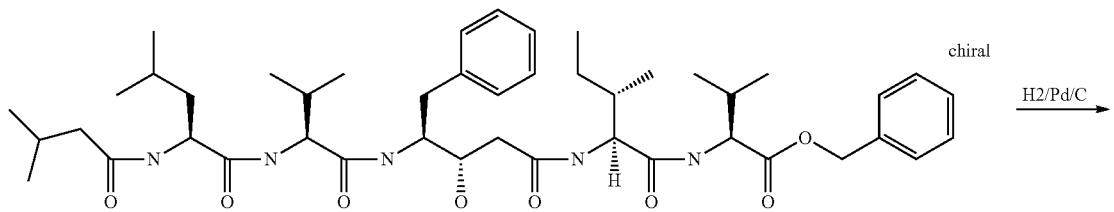

-continued

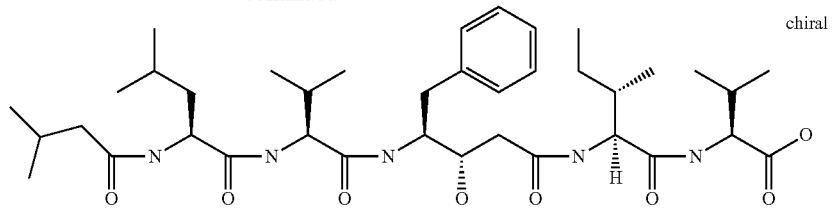

3.400 g of benzyl (S)-2-[(2S,3S)-2-((3S,4S)-3-hydroxy-4-{(S)-3-methyl-2-[(S)-4-methyl-2-(3-methylbutyrylamino)pentanoylamino]butyrylamino}-5-phenylpentanoylamino)-3-methylpentanoylamino]-3-methylbutyrate were hydrogenated in a suitable vessel in the presence of 1.300 g of Pd/C (5% of Pd, moist) in 70 ml of THF at RT at atmospheric pressure until the starting material had completely reacted (overnight). The reaction mixture was diluted with water and THF and filtered off with suction in order to remove the catalyst. The filtrate was evaporated in vacuo and lyophilised for complete removal of the water. The residue was treated with heptane in an ultrasound bath, filtered off with suction and dried. Analogous treatments were carried out with dioxane and then with MTBE, giving 2.45 g of (S)-2-[(2S,3S)-2-((3S,4S)-3-hydroxy-4-{(S)-3-methyl-2-[(S)-4-methyl-2-(3-methylbutyrylamino)pentanoylamino]butyrylamino}-5-phenylpentanoylamino)-3-methylpentanoylamino]-3-methylbutyric acid as white powder (yield 82%). MS-FAB (M+H$^+$)=718.9 R$_f$ (polar method): 2.27 min.

Compounds No. 4-6, 8, 9, 14, 15, 17, 20, 24-31, 33, 36-40 from Table 2 can be prepared analogously to this step.

EXAMPLE 4: PREPARATION OF (A41): (S)-2-[(2S,3S)-2-((3S,4S)-3-HYDROXY-4-{(S)-3-METHYL-2-[(S)-4-METHYL-2-(3-METHYLBUTYRYLAMINO)PENTANOYLAMINO]BUTYRYLAMINO}5-PHENYLPENTANOYLAMINO)-3-METHYLPENTANOYLAMINO]-3-METHYLBUTYRIC ACID

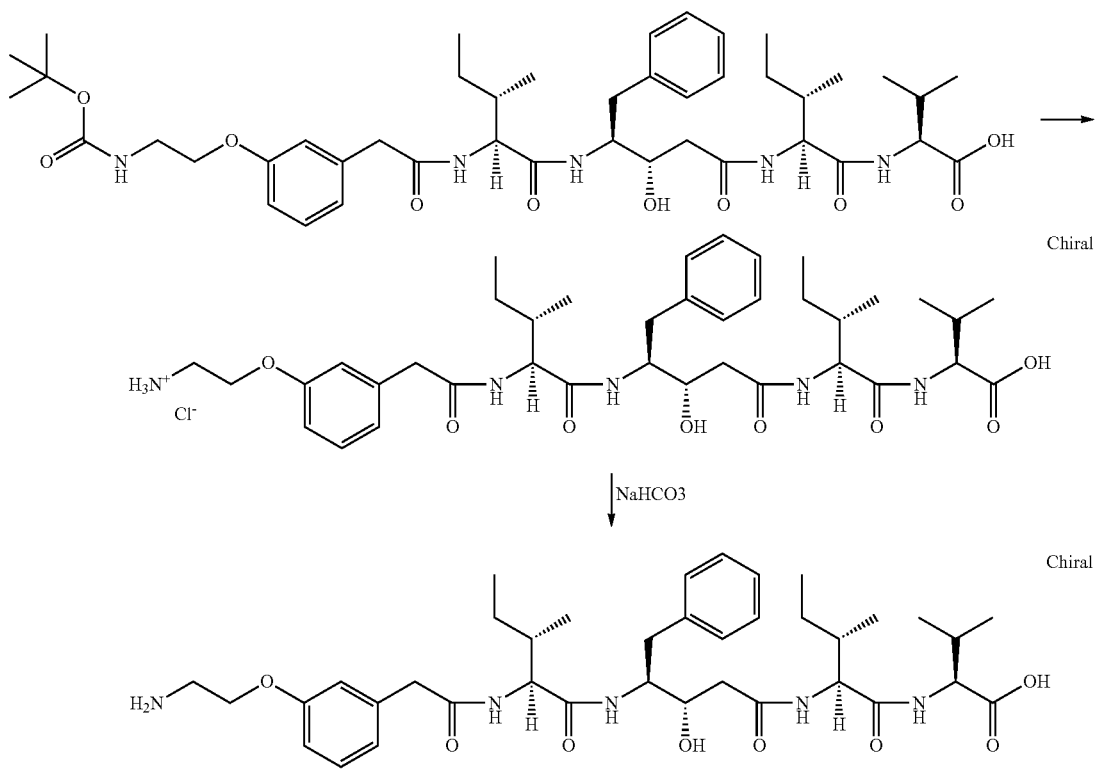

300 mg of (S)-2-{(2S,3S)-2-[(3S,4S)-4-((S)-2-{2-[3-(2-tert-butoxycarbonyl-aminoethoxy)phenyl]acetylamino}-3-methyl-1-(S)-oxopentylamino)-3-hydroxy-5-phenylpentanoylamino]-3-methylpentanoylamino}-3-methylbutyric acid were dissolved with 5 ml of HCl solution in dioxane (4 M) in a flask with ice-cooling and stirred at RT for 5 h. Excess HCl was removed in the house vacuum, the solvent was removed in vacuo, and the residue was lyophilised overnight. Yield of the hydrochloride: quantitative. In order to prepare the free base, a small part of the residue was dissolved in DMF, and this solution was added to 10% sodium hydrogencarbonate solution. The precipitate formed was filtered off with suction, washed with water and dried, giving (S)-2-{(2S,3S)-2-[(3S,4S)-4-((S)-2-{2-[3-(2-aminoethoxy)phenyl]acetylamino}-3-methyl-1-(S)-oxopentylamino)-3-hydroxy-5-phenylpentanoylamino]-3-methylpentanoylamino}-3-methylbutyric acid as white solid.

MS-FAB (M+H$^+$)=712.9 R$_f$ (polar method): 1.70 min.

If a plurality of orthogonal protecting groups are present, the sequence of the cleaving-off of the protecting groups can also be reversed.

Method (HPLC-MS):
Chromolith Speed Rod RP 18e 50-4.6 mm LCMS; polar m. 2.4 ml/min, 220 nm, buffer A 0.05% of HCOOH/H2O, buffer B 0.04% of HCOOH/ACN, 0.0-2.8 min 4%-100% of buffer B; 2.8-3.3 min 100% of buffer B 3.3-3.4 min 100%-4% of buffer B Abbreviations:
DCM=dichloromethane
DMA=dimethylacetamide
DMF=dimethylformamide
EA=ethyl acetate
MTBE=methyl tert-butyl ether
PE=petroleum ether
RT=room temperature
TFA=trifluoroacetic acid

EXAMPLE 4: IN-VITRO FLUORESCENCE ASSAY FOR IDENTIFICATION OF CATHEPSIN D INHIBITORS

In order to identify modulators of cathepsin D activity, a continuous enzymatic test was carried out with a synthetic peptide which carries a fluorescent group (MCA=(7-methoxycoumarin-4-yl)acetyl) which is quenched by energy transfer from a Dpn (2,4 dinitrophenyl) group on the same molecule, in Greiner 384-well nb microtitre plates. Cleavage of the peptidic substrate by cathepsin D causes an increase in the fluorescence intensity. In order to determine the efficacy of substances, the time-dependent increase in the fluorescence intensity in the presence of the substance was compared with the time-dependent increase in fluorescence in the absence of substances. The reference substance used was pepstatin A (Sigma-Aldrich). The substrate used was MCA-GKPILFFRLK(Dnp)d-R—NH$_2$ (Enzo Life Sciences, Lörrach). The enzyme employed was cathepsin D isolated from the human liver (Sigma-Aldrich) in a final concentration of 1.4 nM. The test was carried out in 100 mM sodium acetate buffer, 1.25% (v/v) of DMSO, 0.25% (w/v) of Chaps, pH 5.5. 2 µl of each substance solution with serially diluted substance concentration were added to in each case 4 µl of cathepsin D solution and incubated at room temperature for 10 min. The reaction was started by addition of 2 µl of substrate solution (final concentration 5 µM). After carrying out a starting-point fluorescence measurement (excitation wavelength 340 nm/emission wavelength 450 nm) using an Envision multilabel reader (Perkin Elmer), the reaction was incubated at room temperature for 60 min. The amount of peptide fragment cleaved off during the reaction time was subsequently measured by determination of the increase in the fluorescence intensity at 450 nm (excitation wavelength 340 nm).

All compounds of Table 2 from Example 1 had an IC$_{50}$ value of less than 100 nM (see Table 2, Example 1, penultimate column).

EXAMPLE 5: CARTILAGE EXPLANT ASSAY

In order to investigate the effect of potential cathepsin D inhibitors on cartilage degradation, a pH-induced model based on bovine explants is used. The pH of the medium in which the explants are cultivated is matched here to the pathophysiological pH of an arthrotic knee. This pH is pH 5.5. In this ex vivo model, potential cathepsin D inhibitors are subsequently investigated for their action with respect to stopping of the cartilage degradation process. If the cartilage is destroyed, glycosaminoglycans (GAGs) are released into the cell culture supernatant. The amount of GAGs liberated can be determined quantitatively with the aid of DMMB (dimethylmethylene blue hydrochloride). If sulfated GAGs are detected using dimethylmethylene blue hydrochloride, the decrease in the absorption at 633 nm is utilised. Since work can also be carried out at very low GAG concentrations, a dye/GAG complex does not precipitate out even after extended incubation of DMMB with GAG, which sometimes happens after only a short time in other measurement methods. In order to determine the concentration, a calibration line is also recorded using chondroitin sulfate. The GAG values can be used to calculate an IC$_{50}$ value, i.e. a concentration at which a substance exhibits 50% of its action.

Solutions:
Incubation Medium, pH 7.4:
  DMEM without FBS, addition of 1% of Pen/Strep and 30 µg/ml of ascorbic acid, the medium is not stored.
Incubation Medium, pH 5.5:
  DMEM without FBS, the pH is adjusted by addition of MES and monitored using a pH meter, addition of 1% of Pen/Strep and 30 µg/ml of ascorbic acid.
Solutions for the GAG Measurement:
DMMB Colouring Solution (V=500 ml):
  Dissolve 8 mg of DMMB (dimethylmethylene blue) in 2.5 ml of ethanol+1 g of sodium formate+1 ml of formic acid, make up to 500 ml with bidistilled water.
Incubation Medium:
  FBS (medium without FBS)
Chondroitin Sulfate Solutions (Standard Curve)
  Preparation of standard solutions with the following concentrations: 50 µg/ml; 25 µg/ml; 12.5 µg/ml; 6.25 µg/ml; 3.125 µg/ml; 1.56 µg/ml; 0.78 µg/ml and a blank control of the medium. The preparation of the standard solution is carried out in the medium with which the experiment was also carried out.

1.) Procedure: pH-Induced Cartilage Degradation of Bovine Explants

The bovine explants are firstly prepared. The induction of the cartilage degradation is carried out in 96-multiwell plates. One explant is cultivated per well. In each case, 200 µl of DMEM (incubation medium pH 5.5) without FBS+30 µg/ml of ascorbic acid are added. Thus negative control, explants (n=4) are incubated at pH 7.4 (without FBS). This control is not included in the calculation of the data, but instead ensures that the pH change has the desired effect on the liberation of GAG. At this point, the substances to be tested are added. No pre-incubation of the explants is carried out. The explants are cultivated with the corresponding substances for 3 days in the incubator at 37° C. and 7.5% CO$_2$.

2.) Incubation Procedure

In order to investigate the effect of cathepsin D inhibitors on the liberation of GAG (glycosaminoglycan), the substances are employed in the desired concentration and cultivated for 3 days. The compounds to be tested are tested in a first experiment in a concentration of 1 µM and 1% of DMSO. Substances which have an effect of >50% on the liberation of GAG (this corresponds to <50% of the control in the Assay Explorer) are tested in the next experiment at 100 nM and 1% of DMSO. Substances which have an effect of >50% on the liberation of GAG under these conditions (this corresponds to <50% of the control in the Assay Explorer) are tested in a concentration/effect relationship. The compounds here are investigated in the following concentrations: 30 µM, 10 µM, 3 µM, 1 µM, 0.3 µM, 0.1 µM, 0.03 µM, 0.01 µM.

The positive control used is pepstatin A with a concentration of 0.01 µM. The assay window is defined by the control (pH 5.5), defined as 0% effect, and the control pH 5.5+0.01 µM pepstatin A, defined as 100% effect. After incubation for 3 days, the cell culture supernatants are collected and stored at −20° C. or measured directly. The amount of liberated GAG is measured photometrically.

The effect (1 value) of the respective substance in % based on the positive control (pH 5.5+0.01 µM pepstatin A) and the negative control (pH 5.5) is reported for concentrations of 1 µM and 100 nM. The value represents the average of 4 replicants. In the determination of a concentration/effect relationship, an $IC_{50}$ value is reported to the database (Assay Explorer).

4.) Measurement

The cell culture supernatants (200 µl) are either measured directly or stored at −20° C. In order to ensure an accurate determination of the concentration (µg/ml of GAG in the supernatant) of GAG, the measurement values must be located in the linear region of the standard curve. In order to ensure this, various dilutions are routinely introduced (1/5, 1/10, 1/20, 1/40). The dilutions are prepared with medium and introduced automatically (Hamilton) into a 384-well plate (15 µl). 60 µl of DMMB solution are likewise added automatically (or using a multichannel pipette). A rapid colour reaction occurs, which is subsequently measured at 633 nm using a plate reader (for example Envision). Depending on the amount of sample present, at least one double determination is carried out.

The data are provided by the MTP reader as csv or xls files and stored as raw data based on this format (xls) or used for the calculation of the percentage effect of the particular compound.

5.) Quality Controls

As control for the induction of the pH-induced cartilage degradation, 4 explants are incubated at pH 7.4. This corresponds to the physiological pH of the cartilage, and no effect on the liberation of GAG is thus expected here. These GAG values (µg/ml of supernatant) are thus always significantly lower than the GAG values for incubation at pH 5.5. A further control, which both serves for checking of the experiment, but is also important for the definition of the assay window, is the pepstatin control (pH 5.5+0.01 µM pepstatin A). This substance non-specifically blocks the activity of most proteases and thus determines the maximum possible effect of a compound.

(1) Klompmakers, A. & Hendriks, T. (1986) Anal. Biochem. 153, 80-84, Spectrophotometric Determination of Sulfated Glycosaminoglycans.
(2) Groves, P. J. et al. (1997) Anal. Biochem. 245, 247-248 Polyvinyl alcohol-stabilised binding of sulfated GAGs to dimethylmethylene blue.

6.) Results $IC_{50}$ values were determined for some compounds from Table 2 in Example 1 using this assay and are shown in Table 2 in Example 1 in the final column.

EXAMPLE 6: INVESTIGATION OF THE ANTI-HYPERALGESIC EFFECT IN ANIMALS

In order to induce an inflammation reaction, a carrageenan solution (CAR, 1%, 50 µl), 50 µl) was injected intra-articularly on one side into a rat knee joint. The uninjected side was used for control purposes. Six animals per group were used. The threshold was determined by means of a micrometer screw (medial-lateral on the knee joint), and the thermal hyperalgesia was determined by means of a directed infrared light source by the Hargreaves method (Hargreaves et al., 1988) on the sole of the foot. Since the site of inflammation (knee joint) is different from the site of measurement (paw sole), use is made here of the term secondary thermal hyperalgesia, the mechanism of which is of importance for the discovery of effective analgesics.

Experimental description of thermal hyperalgesia (Hargreaves test): the experimental animal is placed in a plastic chamber on a quartz sheet. Before testing, the experimental animal is firstly given about 5-15 minutes time to familiarise itself with the environment. As soon as the experimental animal no longer moves so frequently after the familiarisation phase (end of the exploration phase), the infrared light source, whose focus is in the plane of the glass bottom, is positioned directly beneath the rear paw to be stimulated. An experiment run is then started by pressing the button: infrared light results in an increase in the skin temperature of the rear paw. The experiment is terminated either by the experimental animal raising the rear paw (as an expression of the pain threshold being reached) or by automatic switching-off of the infrared light source when a prespecified maximum temperature has been reached. Light reflected by the paw is recorded as long as the experimental animal sits still. Withdrawal of the paw interrupts this reflection, after which the infrared light source is switched off and the time from switching on to switching off is recorded. The instrument is calibrated in such a way that the infrared light source increases the skin temperature to about 45 degrees Celsius in 10 s (Hargreaves et al. 1988). An instrument produced by Ugo Basile for this purpose is used for the testing.

CAR was purchased from Sigma-Aldrich. Administration of the specific cathepsin D inhibitor, compound no. 23 (from Example 1, Table 2, (S)-2-[(2S,3S)-2-((3S,4S)-3-amino-4-{(S)-3-methyl-2-[(S)-4-methyl-2-(3-methyl-butyrylamino)pentanoylamino]butyrylamino}-5-phenylpentanoylamino)-3-methylpentanoylamino]-3-methylbutyric acid), was carried out intra-articularly 30 minutes before the CAR. Triamcinolone (TAC) in an amount of 10 µg/joint was used as positive control, and the solvent (vehicle) was used as negative control. The hyperalgesia is quoted as the difference in the withdrawal times between the inflamed and non-inflamed paw.

Result: TAC was capable of reducing the CAR-induced swelling, but the specific cathepsin D inhibitor was not. In contrast, the specific cathepsin D inhibitor was able to reduce the extent of thermal hyperalgesia as a function of the dose (see FIG. 2).

Assessment: it has been shown that compound no. 23 exerts an anti-hyperalgesic action. This can be postulated, since compound no. 23 exhibited no influence on inflammatory swelling and thus on the hyperalgesia trigger. It can thus be assumed that compound no. 23 develops a pain-reducing action in humans.

EXAMPLE 7: STABILITY OF THE COMPOUNDS ACCORDING TO THE INVENTION IN BOVINE SYNOVIAL FLUID

1.) Extraction of Bovine Synovial Fluid

In the preparation of bovine explants (for the diffusion chamber or other assays), either cow hoof (metacarpal joints) or cow knee is used. The synovial fluid can be obtained from both joints. To this end, the synovial fluid is carefully removed from the open joint using a 10 ml syringe and a cannula and transferred into prepared 2 ml Eppendorf vessels. The Eppendorf vessels are labelled depending on the animal (cow passport is available). It must be ensured here that blood does not enter the joint gap during preparation of the joints. If this is the case, the synovial fluid will become a reddish colour and must consequently be discarded. The synovial fluid is basically highly viscous and clear to yellowish in colour. The removal together with a macroscopic analysis of the synovial fluid is documented.

2.) Batch for Stability Testing of Substances in SF

In order to check the stability of individual compounds, a pool of four different bovine synovial fluids is mixed. To this end, about 1 ml per SF is used. The mixture is prepared directly in a 5 ml glass vessel. The SFs are mixed thoroughly, but carefully. No air bubbles or foam should form. To this end, a vortex unit is used at the lowest speed. The compounds to be tested are tested in an initial concentration (unless required otherwise) of 1 µM. After addition of the substance, the batch is again mixed thoroughly and carefully. For visual monitoring, all SF batches are photographed, and the pictures are filed in the eLabBio file for the corresponding experiment. FIG. 1 shows photodocumentation of this type by way of example. The batches are incubated in the incubator for 48 h at 37° C. and 7.5% $CO_2$.

3.) Sampling

The sampling is carried out after the pre-agreed times (unless required otherwise, see below). 200 µl of the SF are removed from the mixture per time and transferred directly into a 0.5 ml "low-binding" Eppendorf vessel. "Low-binding" Eppendorf vessels are used in order to minimise interaction of the substances with the plastic of the vessels. 200 µl of acetonitrile have already been introduced into the Eppendorf vessel, so that a 1+1 mixture of the SF forms thereafter. This simplifies the subsequent analysis, but precipitation of protein may occur immediately after addition of the SF. This should be noted on the protocol. The 0 h sample is taken immediately after addition of the substance. This corresponds to the 100% value in the stability calculation. Ideally, the concentration employed should be retrieved here. The samples can be frozen at −20° C.

0 h
6 h
24 h
48 h

The negative control used is SF without substance. The positive control used is SF with 1 µM of substance. This corresponds to the 0 h value and thus 100% stability.

The samples are stored in "low-binding" Eppendorf vessels at −20° C. The samples are subsequently measured quantitatively.

4.) Data Processing

The concentrations measured (ng/ml) are plotted against the time in a graph (GraphPad Prism®). The percentage stability of the substance is determined here. The 100% value used is the initial value in the SF at time 0 h. The data are stored in eLabBio under the respective experiment number and reported in the MSR database (as percent stability after the corresponding incubation times).

5.) Results

All compounds measured remained stable (see Table 2 in Example 1).

EXAMPLE 8: IN-VITRO FLUORESCENCE ASSAY FOR IDENTIFICATION OF RENIN-INHIBITORY ACTIVITY

In order to identify modulators of renin activity, a continuous enzymatic test was carried out with a synthetic peptide which carries a fluorescent group Edans (=(5-(aminoethyl)aminonaphthalenesulfonate) which is quenched by energy transfer from a Dabcyl (4'-dimethyl-aminoazobenzene-4-carboxylate) group on the same molecule, in Greiner 384-well microtitre plates. Cleavage of the peptidic substrate by renin causes an increase in the fluorescence intensity. In order to determine the efficacy of substances, the time-dependent increase in the fluorescence intensity in the presence of the substance was compared with the time-dependent increase in fluorescence in the absence of substances. The reference substance used was renin inhibitor 2 (Z-Arg-Arg-Pro-Phe-His-Sta-Ile-His N-Boc-Lys methyl ester Z) (Sigma-Aldrich). The substrate used was renin FRET substrate I (DABCYL-g-Abu-Ile-His-Pro-Phe-His-Leu-Val-Ile-His-Thr-EDANS) (Anaspec, Fremont Calif.). The enzyme employed was recombinant human renin (Pro-teos, Kalamazoo, Mich.) in a final concentration of 10 nM. The test was carried out in 50 mM Mops buffer, 1.5% (v/v) of DMSO, 0.1% (w/v) of Igepal®, pH 7.2, 0.5% (w/v) of BSA. 2 µl of each substance solution with serially diluted substance concentration were added to in each case 4 µl of renin solution and incubated at room temperature for 15 min. The reaction was started by addition of 4 µl of substrate solution (final concentration 5 µM). After carrying out a starting-point fluorescence measurement (excitation wavelength 340 nm/emission wavelength 495 nm) using an Envision multilabel reader (Perkin Elmer), the reaction was incubated at 37° C. for 60 min. The amount of peptide fragment cleaved off during the reaction time was subsequently measured by determination of the increase in the fluorescence intensity at 495 nm (excitation wavelength 340 nm).

Result: all compounds measured have an $IC_{50}$ of the renin selectivity of >30 µM (see Table 2 in Example 1).

EXAMPLE 9: INJECTION VIALS

A solution of 100 g of a compound of the formula I and 5 g of disodium hydrogenphosphate in 3 l of bidistilled water is adjusted to pH 6.5 using 2 N hydrochloric acid, filtered under sterile conditions, transferred into injection vials, lyophilised under sterile conditions and sealed under sterile conditions. Each injection vial contains 5 mg of a compound of the formula I.

EXAMPLE 10: SOLUTION

A solution is prepared from 1 g of a compound of the formula I, 9.38 g of $NaH_2PO_4 2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE 11: OINTMENT 500 mg of a compound of the formula I are mixed with 99.5 g of Vaseline under aseptic conditions.

EXAMPLE 12: AMPOULES

A solution of 1 kg of a compound of the formula I in 60 l of bidistilled water is filtered under sterile conditions, transferred into ampoules, lyophilised under sterile conditions and sealed under sterile conditions. Each ampoule contains 10 mg of a compound of the formula I.

The invention claimed is:

1. A method for the treatment of a physiological and/or pathophysiological state selected from the group consisting of arthrosis, arthritis, inflammation-induced pain and inflammation-induced hyperalgesia, comprising intra-articularly administering a compound of the formula I or a physiologically acceptable salt, solvate, prodrug or stereoisomer thereof, including mixtures thereof in all ratios,

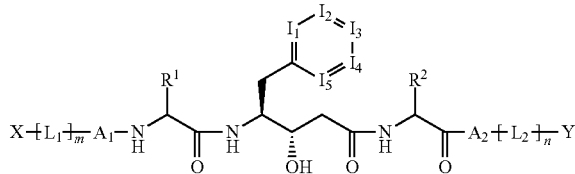

I in which $I_1$, $I_2$, $I_3$, $I_4$, $I_5$, independently of one another, are CR', T is a phenyl, biphenyl or naphthyl which is unsubstituted or mono-, di- tri- or tetrasubstituted by R, or a mono- or bicyclic saturated, unsaturated or aromatic heterocycle having 1 to 4 N, O and/or S atoms, which may be mono-, di- or trisubstituted by R, =S, =NR' and/or =O, $R^1$ is isopropyl, 2-butyl or isobutyl, $R^2$ is n-propyl, isopropyl, 2-butyl or isobutyl, $A_1$ is leucine, $A_2$ is valine, $L_1$ is —(C=O)—, $L_2$ is a single bond, X is linear or branched alkyl having 1-10 C atoms or cyclic alkyl having 3-7 C atoms which is unsubstituted or mono- or di-substituted by T, and in which one, two or three $CH_2$ groups may be replaced, independently of one another, by O, Y is OH or O-benzyl, R and R', independently of one another, are H, linear or branched alkyl having 1-10 C atoms which is unsubstituted or mono-, di- or trisubstituted by =S, =NR, =O, Hal, OH, $NH_2$, $SO_2CH_3$, $SO_2NH_2$, CN, $CONH_2$, $NHCOCH_3$, and/or $NHCONH_2$ and in which one, two or three $CH_2$ groups may be replaced, independently of one another, by O, S, SO, $SO_2$, NH, $NCH_3$, —OCO—, —NHCONH—, —NHCO—, —$NRSO_2A$-, —COO—, —CONH—, —$NCH_3CO$—, —$CONCH_3$—, —C≡C— groups and/or by —CH=CH— groups and/or, in addition, 1-20 H atoms may be replaced by F and/or Cl, or cyclic alkyl having 3-7 C atoms which is unsubstituted or mono-, di- or trisubstituted by =S, =NR, =O, OH, $NH_2$, $SO_2CH_3$, $SO_2NH_2$, CN, $CONH_2$, $NHCOCH_3$, and/or $NHCONH_2$ and in which one, two or three $CH_2$ groups may be replaced, independently of one another, by O, S, SO, $SO_2$, NH, $NCH_3$, —OCO—, —NHCONH—, —NHCO—, —$NRSO_2A$-, —COO—, —CONH—, —$NCH_3CO$—, —$CONCH_3$— and/or by —CH=CH— groups and/or, in addition, 1-11 H atoms may be replaced by F and/or Cl, A is an unbranched or branched hydrocarbon chain and has 1, 2, 3, 4, 5, 6, 7, 8, 9 or 10 C atoms, m is 0, n is 1, and Hal is F, Cl, Br or I.

2. The method of claim 1, wherein, in the compound of formula I, $R^1$ is isopropyl having an S configuration of the chiral centre to which the isopropyl group is bonded, $R^2$ is n-propyl, isopropyl or 2-butyl having an S configuration of the chiral centre to which the n-propyl, isopropyl or 2-butyl group is bonded, $A_1$ is S-leucine and $A_2$ is S-valine, or a physiologically acceptable salt, solvate, prodrug or stereoisomer thereof, including mixtures thereof in all ratios.

3. The method of claim 1, wherein the compound of formula I is one of the following compounds:

(S)-2-[(2S,3S)-2-((3S,4S)-3-hydroxy-4-{(S)-3-methyl-2-[(S)-4-methyl-2-(3-methylbutyrylamino)pentanoylamino]butyrylamino}-5-phenylpentanoylamino)-3-methylpentanoylamino]-3-methylbutyric acid, (S)-2-[(2S,3S)-2-((3S,4S)-3-hydroxy-4-{(R)-3-methyl-2-[(S)-4-methyl-2-(3-methylbutyrylamino)pentanoylamino]butyrylamino}-5-phenylpentanoylamino)-3-methylpentanoylamino]-3-methylbutyric acid, benzyl (S)-2-((2S,3S)-2-{(3S,4S)-3-hydroxy-4-[(S)-3-methyl-2-((S)-4-methyl-2-phenylacetylaminopentanoylamino)butyrylamino]-5-phenylpentanoylamino}-3-methylpentanoylamino)-3-methylbutyrate, or (S)-2-((2S,3S)-2-{(3S,4S)-3-hydroxy-4-[(S)-3-methyl-2-((S)-4-methyl-2-phenylacetylaminopentanoylamino)butyrylamino]-5-phenylpentanoylamino}-3-methylpentanoylamino)-3-methylbutyric acid, or a physiologically acceptable salt, solvate, prodrug or stereoisomer thereof, including mixtures thereof in all ratios.

4. The method of claim 1, wherein the compound of formula I physiologically acceptable salt, solvate, prodrug or stereoisomer thereof, including mixtures thereof in all ratios, upon administration, inhibits cathepsin D.

5. The method of claim 1, wherein the compound of formula I physiologically acceptable salt, solvate, prodrug or stereoisomer thereof, including mixtures thereof in all ratios, is administered in the form of a pharmaceutically stable composition comprising one or more excipients and/or adjuvants.

6. The method of claim 1, wherein the compound of formula I physiologically acceptable salt, solvate, prodrug or stereoisomer thereof, including mixtures thereof in all ratios, is administered in the form of a pharmaceutically stable composition comprising one or more other medicament active compound.

7. The method of claim 1, wherein the compound of formula I physiologically acceptable salt, solvate, prodrug or stereoisomer thereof, including mixtures thereof in all ratios, is administered in a dosage of between 0.1 and 500 mg.

8. The method of claim 1, wherein the compound of formula I physiologically acceptable salt, solvate, prodrug or stereoisomer thereof, including mixtures thereof in all ratios, is administered to a subject in a daily dose of between 0.001 and 250 mg/kg of subject body weight.

9. The method of claim 1, wherein the method is for treating arthrosis.

* * * * *